(12) United States Patent
Olden et al.

(10) Patent No.: US 10,881,276 B2
(45) Date of Patent: Jan. 5, 2021

(54) OVERTUBE DEVICE AND METHOD OF USE

(71) Applicant: Endovate LLC, Scottsdale, AZ (US)

(72) Inventors: Kevin W. Olden, Scottsdale, AZ (US); John David Washington, Scottsdale, AZ (US)

(73) Assignee: Endovate LLC, Scottsdale, AZ (US)

( * ) Notice: Subject to any disclaimer, the term of this patent is extended or adjusted under 35 U.S.C. 154(b) by 68 days.

(21) Appl. No.: 15/398,675

(22) Filed: Jan. 4, 2017

(65) Prior Publication Data
US 2017/0188796 A1 Jul. 6, 2017

Related U.S. Application Data

(60) Provisional application No. 62/274,666, filed on Jan. 4, 2016.

(51) Int. Cl.
*A61B 1/273* (2006.01)
*A61B 17/50* (2006.01)
(Continued)

(52) U.S. Cl.
CPC ...... *A61B 1/00137* (2013.01); *A61B 1/00135* (2013.01); *A61B 1/00144* (2013.01);
(Continued)

(58) Field of Classification Search
CPC ........... A61B 1/00135; A61B 1/00142–00144; A61B 2017/22079; A61M 39/106;
(Continued)

(56) References Cited

U.S. PATENT DOCUMENTS

| 4,991,564 A | * | 2/1991 | Takahashi | A61B 1/00142 600/123 |
| 5,104,379 A | * | 4/1992 | Nakamura | A61B 1/00062 604/111 |

(Continued)

FOREIGN PATENT DOCUMENTS

WO 2014065901 A1 5/2014

OTHER PUBLICATIONS

International Search Report and Written Opinion, PCT/US2016/039437, dated Sep. 8, 2016.

*Primary Examiner* — Wade Miles
(74) *Attorney, Agent, or Firm* — Entralta P.C.; Justin G. Sanders; Peter D. Weinstein

(57) ABSTRACT

An overtube device is disclosed as comprising, in at least one embodiment, a body having a proximal opening and an opposing distal opening in fluid communication with one another via a primary lumen formed within the body, the primary lumen configured for selective receipt and passage therethrough of an endoscope, and a secondary lumen formed within the body so as to intersect and be in fluid communication with the primary lumen and, thus, the distal opening. The secondary lumen is configured for selective engagement with a suction system and defines a suction port. With the distal end of the overtube device attached to the overtube and the suction system engaged with the suction port of the overtube device, suction applied via the suction system through the suction port is, in turn, capable of being applied to the overtube.

19 Claims, 14 Drawing Sheets

(51) Int. Cl.
*A61B 17/00* (2006.01)
*A61B 1/00* (2006.01)
*A61B 1/015* (2006.01)

(52) U.S. Cl.
CPC ............ *A61B 1/015* (2013.01); *A61B 1/2733* (2013.01); *A61B 17/50* (2013.01); *A61B 2017/00561* (2013.01); *A61B 2017/00818* (2013.01)

(58) Field of Classification Search
CPC ........... A61M 39/12; A61M 2039/1077–1094; A61M 39/20; A61M 2039/205; A61M 25/0097
See application file for complete search history.

(56) References Cited

U.S. PATENT DOCUMENTS

| | | | |
|---|---|---|---|
| 5,536,234 A * | 7/1996 | Newman ............ | A61B 1/00091 600/104 |
| 5,695,448 A | 12/1997 | Kimura et al. | |
| 6,572,629 B2 | 6/2003 | Kalloo et al. | |
| 7,204,804 B2 | 4/2007 | Zirps et al. | |
| 2002/0173699 A1* | 11/2002 | Becker ............... | A61B 1/00091 600/114 |
| 2003/0225312 A1* | 12/2003 | Suzuki ............. | A61B 17/00234 600/114 |
| 2006/0122559 A1* | 6/2006 | Shia ...................... | A61M 39/12 604/77 |
| 2008/0103410 A1 | 5/2008 | Karpiel et al. | |
| 2008/0119693 A1 | 5/2008 | Makower et al. | |
| 2008/0188868 A1 | 8/2008 | Weitzner et al. | |
| 2010/0010298 A1* | 1/2010 | Bakos ................ | A61B 1/00135 600/106 |
| 2010/0057045 A1* | 3/2010 | Albritton, IV ...... | A61M 1/0086 604/506 |
| 2011/0077621 A1* | 3/2011 | Graham ............ | A61M 25/0136 604/528 |
| 2014/0024896 A1* | 1/2014 | West ........................ | A61B 1/12 600/114 |
| 2017/0150993 A1* | 6/2017 | Ganz ...................... | A61B 17/50 |
| 2018/0289394 A1* | 10/2018 | Shah .................. | A61B 1/00135 |

* cited by examiner

OVERTUBE DEVICE AND METHOD OF USE

This U.S. Non-Provisional patent application claims the benefit of priority pursuant to 35 U.S.C. § 119(e) to U.S. Provisional Patent Application 62/274,666, filed on Jan. 4, 2016, which is hereby incorporated by reference in its entirety.

In gastroenterology practice and in emergency room and other such cases, it is not uncommon for a patient to present with a partial or complete blockage of the esophagus, as by a foreign object or a food impaction, causing pain, nausea or vomiting, loss of appetite, and other such symptoms. Clinical challenges related to assessment and non-surgical treatment of such esophageal conditions call for improved devices and methods particularly relating to endoscopy.

The most common form of esophageal blockage is generally understood to be a food impaction such as meat bolus. Treatment options for such food bolus impactions generally fall into two categories: removal or extraction ("pull technique"); or advancement of the bolus into the stomach ("push technique"). Visualization of the food impaction and surrounding anatomy proximal and distal of the impaction is an important aspect of diagnosis and treatment. Visualization throughout the selected treatment is preferable. As such, endoscopic techniques are widely used.

Esophageal food impaction can have a variety of causes, determination of which plays a further role in ultimately determining the recommended treatment. Sometimes the meat or other food bolus is simply too large and/or not sufficiently chewed, and being substantially solid or semi-solid, it has become lodged in the esophagus, often just above the lower esophageal sphincter. In other cases, some esophageal pathology such as lesions or tumors, scarring, Schatzki rings, predisposing peptic stricture, or other such esophageal condition or abnormality is responsible for the food impaction due to effectively obstructing or narrowing the esophagus. In any such cases, the food impaction may thus be solid or semi-solid but is most often gooey, semi-digested food, sometimes amounting to on the order of 1-2 cups.

Removal or extraction of such common food impactions presents specific clinical challenges, particularly when repeated insertions of an endoscope or other such device can increase the risk of patient trauma and post-procedure discomfort. Concerns regarding esophageal perforation and aspiration (material passing into the trachea and lungs), either of which could be life-threatening, have led to the development and use of a number of related endoscopic devices such as overtubes and protective hoods, but these devices have their own limitations and drawbacks and ultimately do not address the issue of more efficiently removing the impaction while under substantially consistent visualization. And where it has been determined that an anatomical condition or pathology has caused the food impaction, this will often rule out some treatment options, including for many practitioners any "push technique" for fear of trauma to the likely already compromised anatomy.

Other related approaches to attempting to treat a food impaction without surgery have shortcomings as well, such as the medical or pharmacological approach of relaxing the esophagus through the administration of glucagon or other agent, which carries the risk of reflux and aspiration into the trachea and lungs, or the introduction of enzyme compounds in an attempt to dissolve the blockage, which simply adds time and uncertainty to the procedure, the hope being with either of these pharma approaches that the impaction will pass on its own if given enough time under the right conditions (which assumes that the pathology can ultimately accommodate passage of the impaction). Insufflation, or attempting to effectively inflate or expand the esophagus with air so as to dilate the esophagus and allow the impaction to pass, also involves risks to what could be already compromised anatomy as well as presenting similar concerns regarding reflux and aspiration. Finally, devices employed in connection with foreign body removal from the esophagus or stomach such as Roth or Dormia baskets, nets, polypectomy snares, alligator, rat-tooth, or shark-tooth forceps or graspers, and magnetic retrievers are most often simply incapable of extracting the semi-digested, mushy food impaction typically encountered.

What the clinician is effectively left with in treating the most common type of esophageal impaction (food bolus or the like) is suction, typically through the suction port of the endoscope itself. However, the typical 2-4 mm suction channel of the average gastroscope is woefully inadequate to remove a relatively large volume food impaction of on the order of 1-2 cups and is prone to clogging. Even experienced practitioners may be required using such standard equipment to make 30-40 passes (insertions) over the course of on the order of 2 hours to completely remove the impaction, which again can lead to at least patient soreness and extended time under sedation as well as potential trauma to the esophagus, such as damage to the mucosa or actual perforation. What is needed is a device, in the form of an overtube attachment or a purpose-built overtube, that enables more effective removal of esophageal food impactions by essentially providing a much larger suction channel while still allowing for endoscope usage and visualization of the food impaction or other foreign body and the anatomy before, during, and/or after the procedure.

Furthermore, even in the case of foreign object removal, an improved overtube device and method can equip the clinician to more effectively and safely extract such an object non-surgically. For example, by employing an overtube or overtube attachment having suction capability even while allowing for passage of an endoscope allows for both visualization and suction or other endoscope operation with effectively a single intubation event (that of the overtube), with the overtube retaining and effectively shielding a foreign body along with the scope. In some contexts, the blockage may involve both a foreign object and food impaction, such that an overtube device that is better equipped to manage both kinds of blockage, or a combination thereof, can effectively enable more efficient removal by the clinician.

The present specification addresses the shortcomings of known devices and methods for non-surgical treatment or management of esophageal food impactions and foreign bodies. The present specification discloses an overtube device having a proximal end and an opposite distal end configured for selective attachment to an overtube, the overtube device comprising a body having a proximal opening formed at the proximal end and an opposite distal opening formed at the distal end, the proximal and distal openings being in fluid communication, a primary lumen formed within the body interconnecting the proximal and distal openings, the primary lumen being configured for selective receipt and passage therethrough of an endoscope, and a secondary lumen formed within the body so as to intersect and be in fluid communication with the primary lumen and thus the distal opening, the secondary lumen being configured for selective engagement with a suction system and thus defining a suction port, whereby with the distal end of the overtube device attached to the overtube and with the suction system engaged with the suction port of the overtube device, suction applied via the suction system through the suction port and thus the secondary and primary lumens formed within the body of the overtube device applies suction to the overtube.

SUMMARY

Aspects of the present invention teach certain benefits in construction and use which give rise to the exemplary advantages described below.

Aspects of the present specification provide an overtube device having a proximal end and an opposite distal end configured for selective attachment to an overtube, the overtube device comprising a body having a proximal opening formed at the proximal end and an opposite distal opening formed at the distal end, the proximal and distal openings being in fluid communication, a primary lumen formed within the body interconnecting the proximal and distal openings, the primary lumen being configured for selective receipt and passage therethrough of an endoscope, and a secondary lumen formed within the body so as to intersect and be in fluid communication with the primary lumen and thus the distal opening, the secondary lumen being configured for selective engagement with a suction system and thus defining a suction port, whereby with the distal end of the overtube device attached to the overtube and with the suction system engaged with the suction port of the overtube device, suction applied via the suction system through the suction port and thus the secondary and primary lumens formed within the body of the overtube device applies suction to the overtube.

Other aspects of the present specification provide an overtube device having a primary lumen inside diameter that is substantially equivalent to a secondary lumen inside diameter.

Other aspects of the present specification provide an overtube device having a primary lumen inside diameter that is substantially equal to or greater than an overtube inside diameter.

Other aspects of the present specification provide an overtube device having an intersection of the secondary lumen with the primary lumen at an acute angle.

Other aspects of the present specification provide an overtube device having a suction port formed having an integral barb fitting extending proximally therefrom, the barb fitting being a substantially coaxial extension of the secondary lumen.

Other aspects of the present specification provide an overtube device having a distal portion configured for engagement with a proximal end of an overtube, and more particularly having an external thread formed on the distal portion configured for engagement with an internal thread formed within a grip portion connector of the overtube.

Other aspects of the present specification provide an overtube device having a proximal portion configured for engagement with a distal end of an overtube cap, and more particularly having an internal thread formed within the primary lumen substantially at the proximal portion configured for engagement with an external thread formed on the overtube cap.

Other aspects of the present specification provide an overtube device having a separator configured for connection to the suction port as part of the suction system.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

The present specification relates generally to a device that would attach to an overtube or be formed as a "purpose-built overtube" to assist a G.I. doctor or other clinician in visualizing and removing a "foreign body" or "food impaction" or "bolus" from a patient's esophagus, as when a patient has swallowed something too hard or large to pass into their stomach that has instead become lodged in the esophagus or when the patient has some anatomical issue within the esophagus that has caused a restriction, in either case the obstruction needing to be safely and preferably non-surgically removed. According to aspects of the present invention, the overtube device enables food impaction or foreign body removal using suction in a new and improved way, basically converting an overtube into a suction-based foreign body removal device and thereby allowing for removal of all or substantially all of the foreign material in a single pass or intubation, thereby reducing the risk of patient trauma (e.g., perforation of the esophagus) or discomfort during and after the procedure, all while still allowing endoscope insertion for at least visualization of the foreign material and related anatomy before, during and/or after the procedure as well as potential endoscopic assistance in the removal, such as by deploying a tool to break up the food impaction or to retrieve or manipulate a substantially solid foreign object. While one or more exemplary embodiments of such an overtube device are shown and described, it will be appreciated by those skilled in the art that a variety of other such devices according to aspects of the present invention are possible and that features may be differently combined or substituted employing any related technologies now known or later developed without departing from the spirit and scope of the invention.

Figure 1:
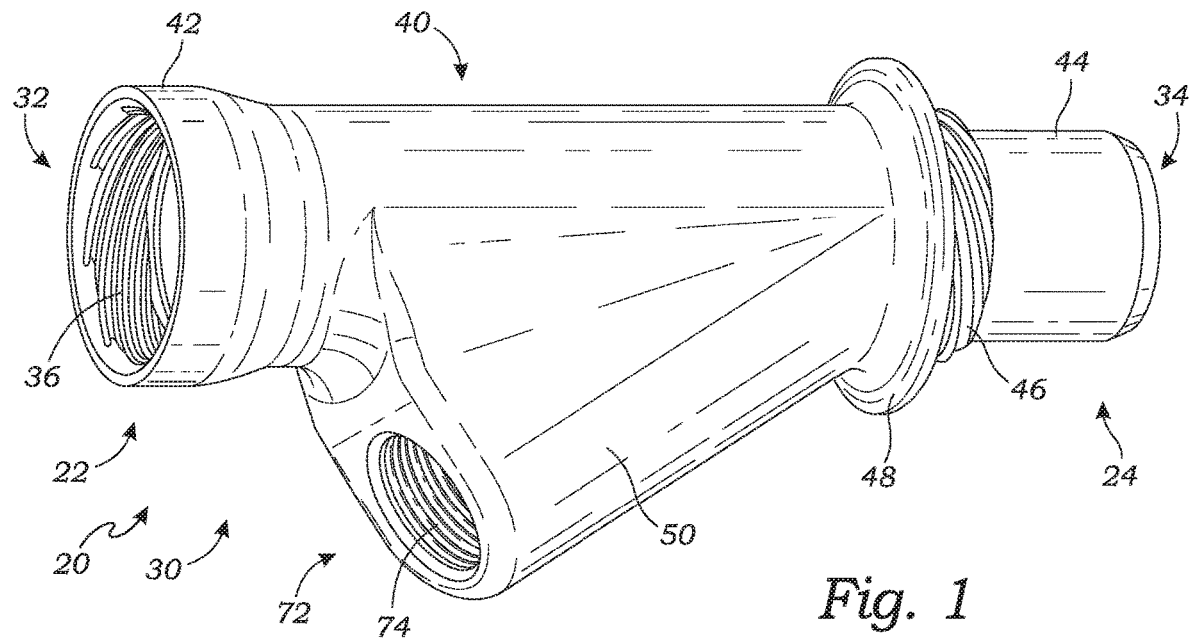
FIG. 1 illustrates a perspective view of an exemplary overtube device, in accordance with at least one embodiment.
Figure 2:
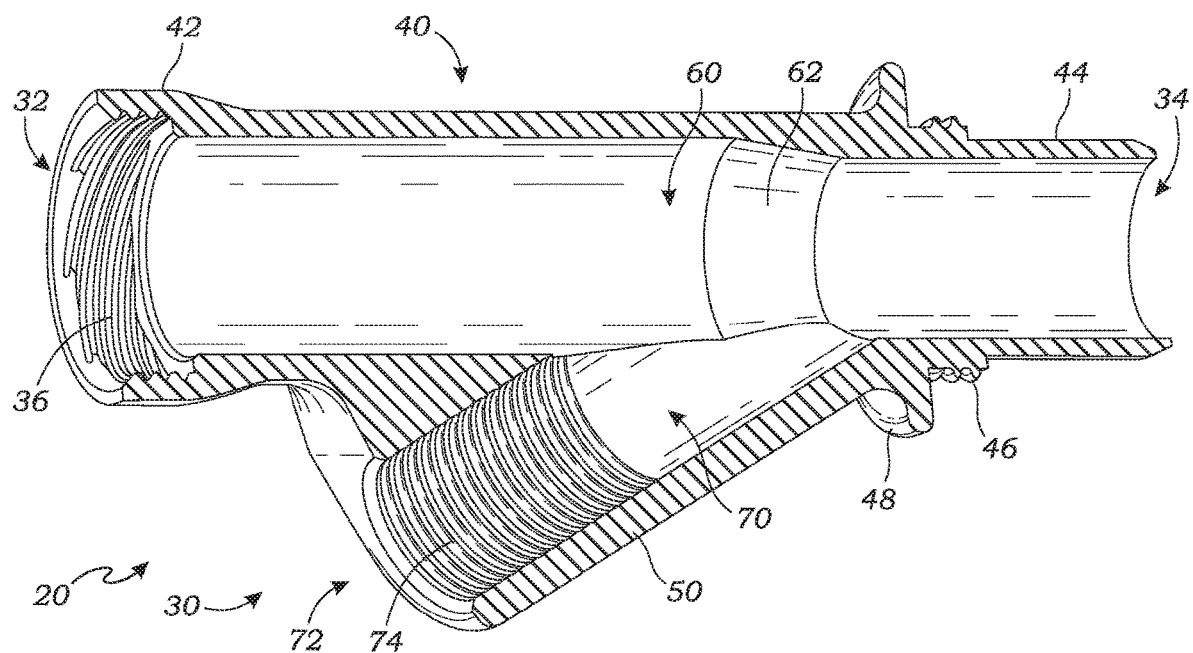
FIG. 2 illustrates a cross-sectional view thereof, in accordance with at least one embodiment.
Figure 5:
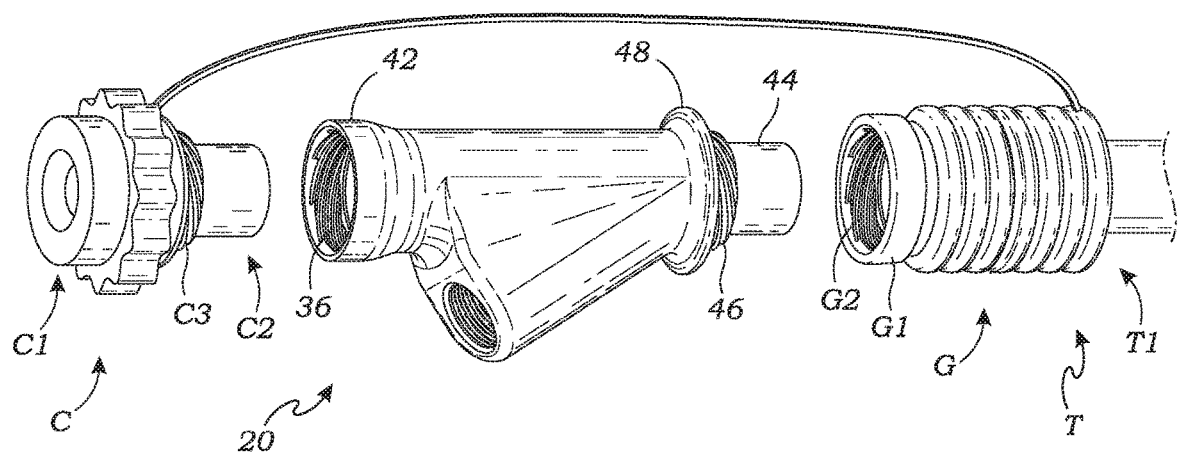
FIG. 5 illustrates a reduced scale exploded perspective view of the exemplary overtube device of FIGS. 1 and 2 as assembled in conjunction with an overtube, in accordance with at least one embodiment.
Figure 6:
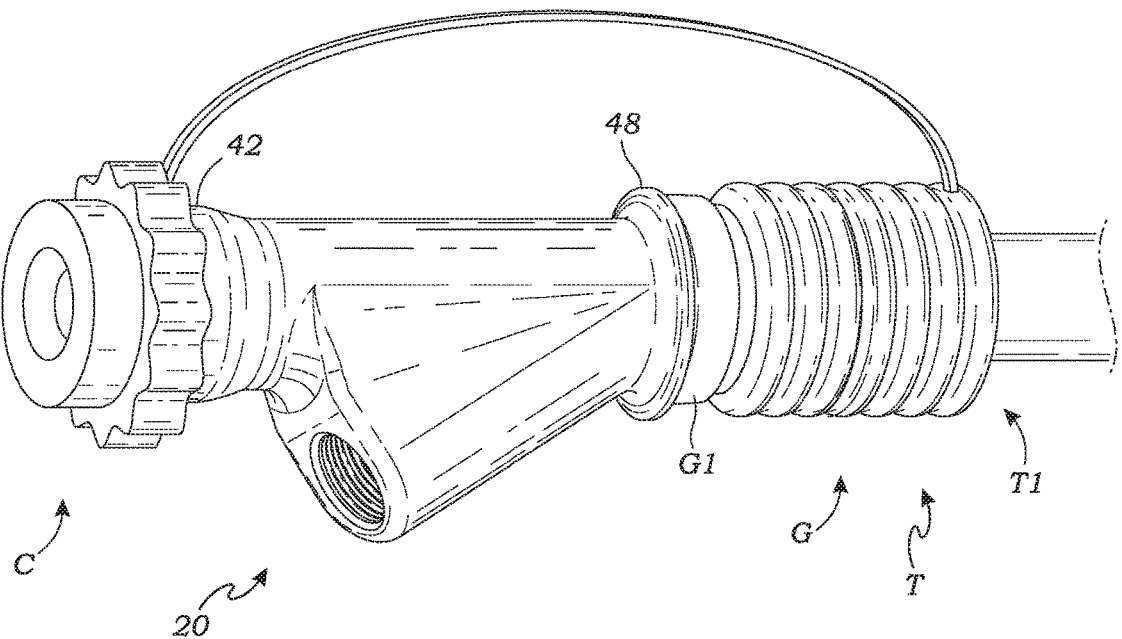
FIG. 6 illustrates an enlarged assembled perspective view thereof installed on the proximal end of the illustrated overtube, in accordance with at least one embodiment.
Figure 7:
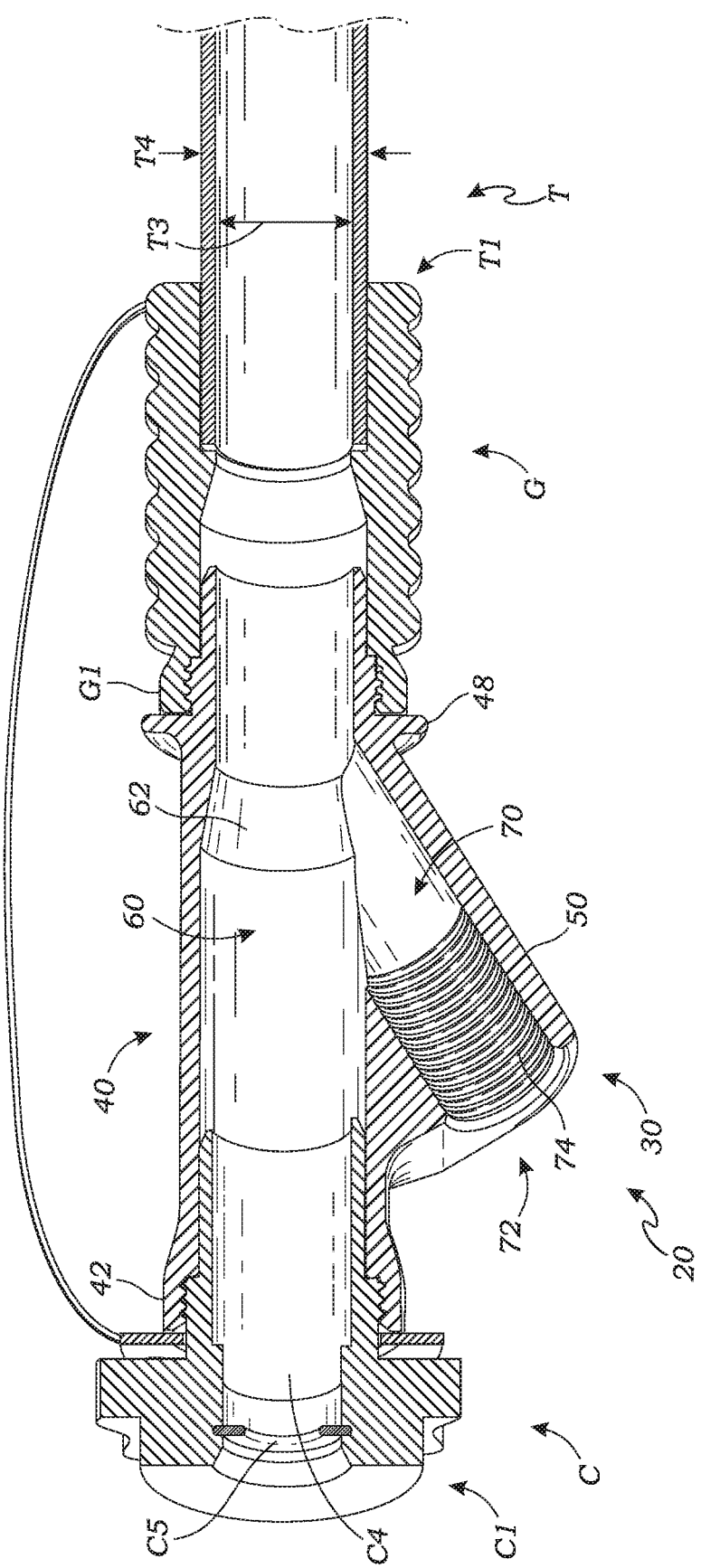
FIG. 7 illustrates an enlarged cross-sectional view thereof, in accordance with at least one embodiment.

Referring first to FIGS. 1 and 2, there are shown perspective solid and cross-sectional views of an exemplary overtube device 20, in accordance with at least one embodiment, configured for selective or removable attachment on the proximal end T1 of an overtube T (FIGS. 5-7). The overtube device 20 generally comprises a body 30 extending between a proximal end 22 and a distal end 24 of the device 20 and having a proximal opening 32 and an opposite distal opening 34, respectively. The body 30 is defined by a body wall 40 having a somewhat enlarged proximal portion 42 associated with the proximal opening 32 of the body 30, a stepped-down distal portion 44 associated with the distal opening 34 of the body 30, and an intermediate suction port 50 extending from the body wall 40, more about which is said below. Within the body 30 of the overtube device 20 there are formed a primary lumen 60 associated with passage of an endoscope N (FIG. 8A) and an interconnected secondary lumen 70 associated with suction or retrieval, more about which is said further below particularly in connection with an exemplary device 20 in use as illustrated in FIGS. 8A-8J. By way of overview, the primary lumen 60 is formed within the body 30 between the proximal and distal openings 32, 34 and configured as a substantially linear channel of sufficient size for selective receipt and passage therethrough of a standard endoscope N. The secondary lumen 70 is again formed so as to intersect and be in fluid communication with the primary lumen 60 and thus the distal opening 34 and is configured for selective engagement with a suction system 80 (FIG. 8G) so as to define the suction port 50 portion of the device body 30 configured for suction to be selectively applied therethrough, whereby with an overtube T attached to the distal end 24 of the overtube device 20 and the suction system 80 engaged with the suction port 50 of the overtube device 20, suction applied via the suction system 80 through the suction port 50 and thus the secondary and primary lumens 70, 60 formed within the body 30 of the overtube device 20 applies suction to the overtube T. Specifically, the secondary lumen 70 formed within the suction port 50 may itself be formed at its proximal opening 72 with an internal thread 74 configured for receipt of a barb fitting or any other such connector now known or later developed for facilitating the selective attachment of the suction system 80. It will be appreciated that any such removable engagement means now known or later developed may be employed, such that the internal thread 74 should be understood as merely illustrative and non-limiting. As shown, the device 20 may be generally proportioned so as to be longer than it is wide, with the suction port 50 extending from the body wall 40 at an angle of approximately thirty degrees (30°) for a smooth transition between the primary and secondary lumens 60, 70, thereby forming effectively a "Y" connector or split, though it will be appreciated that a range of angles between the suction port 50 and the axial body wall 40, and thus between the secondary lumen 70 and the primary lumen 60, are possible essentially between zero and ninety degrees (0-90°), the latter defining a "T" connector or split. Preferably, the angle between the primary and secondary lumens 60, 70 would be in the range of approximately ten to sixty degrees (10-60°), more preferably in the range of approximately twenty to forty-five degrees (20-45°), and most preferably in the range of approximately twenty-five to thirty-five degrees (25-35°). Those skilled in the art will further appreciate that a variety of other geometrical arrangements and proportions of the components or aspects of the device 20 are possible without departing from the spirit and scope of the invention, it being appreciated that certain geometrical considerations are dictated, at least in part, by prior art or now known or later developed endoscopes and overtubes and related fittings in conjunction with which the device 20 is to be configured to operate according to aspects of the present invention. In the exemplary embodiment, the overtube device 20 is substantially annular, having a somewhat constant, relatively larger diameter at its proximal end 22 stepping up slightly at the proximal portion 42 of the body wall 40 associated with the proximal opening 32 through which an endoscope N may be inserted and to accommodate an overtube cap C (FIGS. 5-7), more about which is said below, and having a somewhat constant, relatively smaller diameter at its distal end 24 associated with the distal portion 44 of the body wall 40 and the distal opening 34 of the body 30 through which a food impaction or other material may be suctioned into and through the device 20, in whole or in part. Accordingly, a tapered portion 62 of the primary lumen 60 is formed between the proximal and distal ends 22, 24 of the device 20, which it will be appreciated also provides for smooth insertion of an endoscope N during use of the overtube device 20. Those skilled in the art should understand that all figures in the present application are schematic in nature and fundamentally that none of the figures are to be taken literally or to scale, each such figure being simply illustrative of features and aspects of the present invention and non-limiting. While the exemplary overtube device 20 is shown as being annular, this is not necessarily the case, as other geometries such as elliptical may also be employed in at least portions of the device 20.

Figure 3:
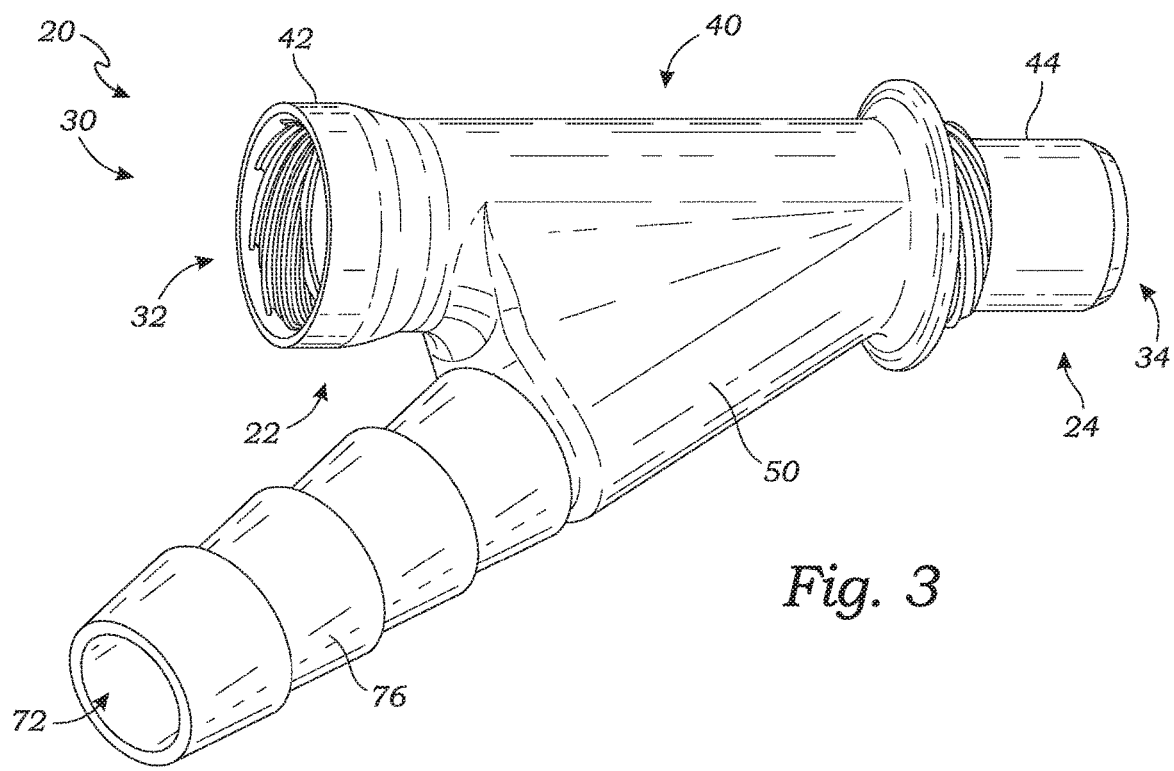
FIG. 3 illustrates an alternative reduced scale perspective view thereof, in accordance with at least one embodiment.
Figure 4:
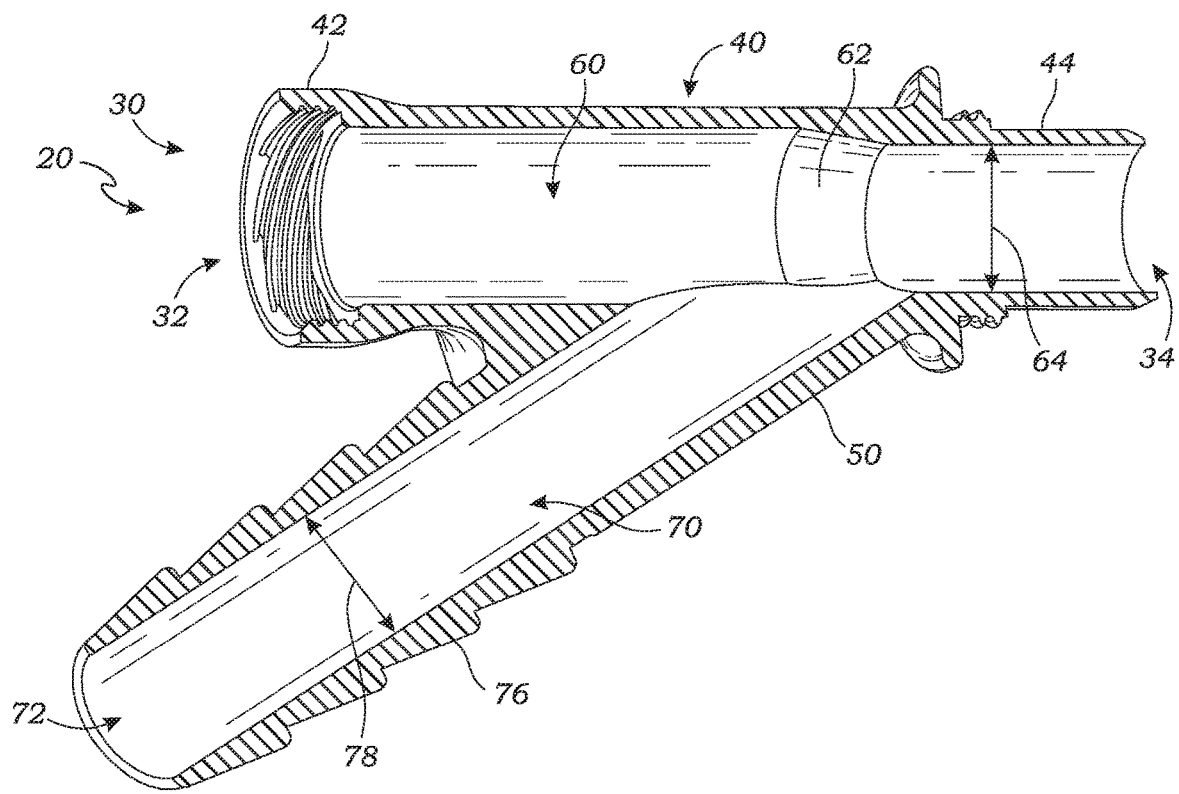
FIG. 4 illustrates a cross-sectional view thereof, in accordance with at least one embodiment.

Turning briefly to FIGS. 3 and 4, there are shown perspective solid and cross-sectional views of an alternative exemplary overtube device 20, in accordance with at least one embodiment, again configured for selective or removable attachment on the proximal end T1 of an overtube T (FIGS. 5-7). The overtube device 20 once more generally comprises a body 30 extending between a proximal end 22 and a distal end 24 of the device 20 and having a proximal opening 32 and an opposite distal opening 34, respectively. The body 30 is defined by a body wall 40 having a somewhat enlarged proximal portion 42 associated with the proximal opening 32 of the body 30, a stepped-down distal portion 44 associated with the distal opening 34 of the body 30, and an intermediate suction port 50 extending from the body wall 40. Here, instead of having an internal thread 74 formed within the proximal opening 72 of the secondary lumen 70 that defines the suction port 50, a barb fitting 76 is formed integrally with and extends proximally from the suction port 50 so as to serve as a substantially coaxial extension of the secondary lumen 70 and facilitate direct attachment of the suction system 80 (FIG. 8G), the proximal opening 72 of the secondary lumen 70 then being effectively located at the proximal end or tip of the barb fitting 76. Again, those skilled in the art will appreciate that any such connector now known or later developed may be removably engaged with or, as here, be formed integrally with the suction port 50 according to aspects of the present invention without departing from its spirit and scope. It will be appreciated that a barb fitting such as that shown may be configured geometrically in a variety of shapes and sizes and so is not limited to the particular configuration and relative size shown, which is merely illustrative and non-limiting. Relatedly, while the barb fitting 76 is shown and described as being coaxial with the secondary lumen 70 and essentially parallel with or at the same angle as the suction port 50, such is not required, and the barb fitting 76 may instead be formed at some other angle or orientation as desired. Within the body 30 of the overtube device 20 there are again formed the primary lumen 60 between the proximal and distal openings 32, 34 and configured as a substantially linear channel of sufficient size for selective receipt and passage therethrough of a standard endoscope N and the interconnected secondary lumen 70 in fluid communication with the primary lumen 60 and thus the distal opening 34 and configured for selective engagement with the suction system 80 so as to define the suction port 50 portion of the device body 30.

As shown in FIGS. 1-4, the exemplary overtube device 20 may be of a unitary construction formed of a single material, as by injection molding or any other such manufacturing technique now known or later developed. In other applications, the device 20 may be formed of two or more components, such as potentially forming the body wall 40 separate from the suction port 50 so as to together form the body 30, as by an over-molding process or otherwise forming or installing one part on the other or assembling the two parts together after they are formed employing any assembly technique now known or later developed, including but not limited to solvent boding or ultrasonic welding. Again, any such components may be formed of the same or different material depending on aspects of the invention and its intended use. In the exemplary embodiment, the device 20, and the device body 30 specifically, being of a unitary construction may be formed as through injection molding or the like of a relatively rigid plastic, polymer, rubber, elastomer, resin, or the like such as relatively hard or high durometer polyvinyl or polyvinyl chloride ("PVC"), polyethylene or high density polyethylene ("HDPE"), polypropylene, polyurethane, polycarbonate, acrylic, acrylonitrile butadiene styrene ("ABS"), nylon, polylactic acid ("PLA"), polybenzimidazole, polyether sulfone, polyether ether ketone, polyetherimide, polyphenylene oxide, polyphenylene sulfide, polystyrene, Teflon, silicone rubber, or any other such thermoplastic or like material now known or later developed. By way of illustration and not limitation, the hardness of the device body 30 may be in the range of 25-100 Shore A durometer.

An overtube device 20 disclosed herein has a material of construction for the body 30 adequate to maintain its shape and provide mechanical integrity during use, as when installed on an overtube T (FIGS. 5-7). In aspects of this embodiment, an overtube device 20 disclosed herein has a body 30 having a Shore A durometer hardness of, e.g., about 25, about 30, about 35, about 40, about 45, about 50, about 55, about 60, about 65, about 70, about 75, about 80, about 85, about 90, about 95, or about 100. In other aspects of this embodiment, an overtube device 20 disclosed herein has a body 30 having a Shore A durometer hardness of, e.g., at least 25, at least 30, at least 35, at least 40, at least 45, at least 50, at least 55, at least 60, at least 65, at least 70, at least 75, at least 80, at least 85, at least 90, at least 95, or at least 100. In other aspects of this embodiment, an overtube device 20 disclosed herein has an interior fitting 70 having a Shore A durometer hardness of, e.g., at most 25, at most 30, at most 35, at most 40, at most 45, at most 50, at most 55, at most 60, at most 65, at most 70, at most 75, at most 80, at most 85, at most 90, at most 95, or at most 100.

In still other aspects of this embodiment, an overtube device 20 disclosed herein has a body 30 having a Shore A durometer hardness of, e.g., about 25 to about 30, about 25 to about 35, about 25 to about 40, about 25 to about 45, about 25 to about 50, about 25 to about 55, about 25 to about 60, about 25 to about 65, about 25 to about 70, about 25 to about 75, about 25 to about 80, about 25 to about 85, about 25 to about 90, about 25 to about 95, about 25 to about 100, about 30 to about 35, about 30 to about 40, about 30 to about 45, about 30 to about 50, about 30 to about 55, about 30 to about 60, about 30 to about 65, about 30 to about 70, about 30 to about 75, about 30 to about 80, about 30 to about 85, about 30 to about 90, about 30 to about 95, about 30 to about 100, about 35 to about 40, about 35 to about 45, about 35 to about 50, about 35 to about 55, about 35 to about 60, about 35 to about 65, about 35 to about 70, about 35 to about 75, about 35 to about 80, about 35 to about 85, about 35 to about 90, about 35 to about 95, about 35 to about 100, about 40 to about 45, about 40 to about 50, about 40 to about 55, about 40 to about 60, about 40 to about 65, about 40 to about 70, about 40 to about 75, about 40 to about 80, about 40 to about 85, about 40 to about 90, about 40 to about 95, about 40 to about 100, about 45 to about 50, about 45 to about 55, about 45 to about 60, about 45 to about 65, about 45 to about 70, about 45 to about 75, about 45 to about 80, about 45 to about 85, about 45 to about 90, about 45 to about 95, about 45 to about 100, about 50 to about 55, about 50 to about 60, about 50 to about 65, about 50 to about 70, about 50 to about 75, about 50 to about 80, about 50 to about 85, about 50 to about 90, about 50 to about 95, about 50 to about 100, about 55 to about 60, about 55 to about 65, about 55 to about 70, about 55 to about 75, about 55 to about 80, about 55 to about 85, about 55 to about 90, about 55 to about 95, about 55 to about 100, about 60 to about 65, about 60 to about 70, about 60 to about 75, about 60 to about 80, about 60 to about 85, about 60 to about 90, about 60 to about 95, about 60 to about 100, about 65 to about 70, about 65 to about 75, about 65 to about 80, about 65 to about 85, about 65 to about 90, about 65 to about 95, about 65 to about 100, about 70 to about 75, about 70 to about 80, about 70 to about 85, about 70 to about 90, about 70 to about 95, about 70 to about 100, about 75 to about 80, about 75 to about 85, about 75 to about 90, about 75 to about 95, about 75 to about 100, about 80 to about 85, about 80 to about 90, about 80 to about 95, about 80 to about 100, about 85 to about 90, about 85 to about 95, about 85 to about 100, about 90 to about 95, about 90 to about 100, or about 95 to about 100.

Once more, the body 30 itself may be formed of multiple components or materials in order to suit particular design objectives. For example, while the exemplary connections between the device 20 and the overtube T (FIGS. 5-7) at its distal end 24 and the overtube cap C (FIGS. 5-7) at its proximal end 22 are shown as a threaded engagement, more about which is said below particularly in connection with FIGS. 5-7, it will be appreciated that in other applications one or both such connections may be a net-, press- or interference-fit (i.e., a frictional fit) or other such connection now known or later developed. Accordingly, in such an alternative embodiment, the body 30 particularly at one or both of the proximal and distal ends 22, 24 of the device 20, or at or adjacent the proximal and distal openings 32, 34, may be relatively soft and pliable and even somewhat "gummy" so as to allow a good frictional engagement between the device and the respective overtube T or cap C. At the same time, it is desirable that the ends of the device 20 also be somewhat pliable or flexible so that the proximal and distal openings 32, 34 have integrity and substantially maintain their intended or "at rest" shape during use so as to properly fit on (about or within) the respective geometry of the overtube T or cap C. Where such a difference in performance or function of the body 30, and the body wall 40 specifically, from end to end or along its length can be achieved through the incorporation of different materials having varying mechanical properties or dimensionally as by increasing or decreasing wall thickness along the body 30, or both. In the exemplary embodiment as best shown in FIGS. 2 and 4, the body 30 of the device 20 is formed of a single material with two different wall thicknesses: a relatively thinner wall at the distal end 24 and a relatively thicker wall at the proximal end 22. By way of further illustration, the body 30 may be formed, at least in part, of a relatively soft plastic, polymer, rubber, elastomer, resin or the like such as relatively soft or low durometer polyvinyl or polyvinyl chloride ("PVC"), polyethylene or high density polyethylene ("HDPE"), polypropylene, polyurethane, polycarbonate, acrylic, acrylonitrile butadiene styrene ("ABS"), nylon, polylactic acid ("PLA"), polybenzimidazole, polyether sulfone, polyether ether ketone, polyetherimide, polyphenylene oxide, polyphenylene sulfide, polystyrene, Teflon, silicone rubber, or any other such thermoplastic or like material now known or later developed. By way of illustration, the hardness of a portion of the body 30 may be in the range of 10-80 Shore A durometer.

According to further aspects of the present invention, an overtube device 20 as disclosed herein may have a material of construction for at least a portion of the body 30 adequate to maintain its shape while having sufficient pliability or flexibility as part of the overall device 20. In aspects of this embodiment, an overtube device 20 disclosed herein has a portion of the body 30 having a Shore A durometer hardness of, e.g., about 10, about 15, about 20, about 25, about 30, about 35, about 40, about 45, about 50, about 55, about 60, about 65, about 70, about 75, or about 80. In other aspects of this embodiment, an overtube device 20 disclosed herein has at least a portion of the body 30 having a Shore A durometer hardness of, e.g., at least 10, at least 15, at least 20, at least 25, at least 30, at least 35, at least 40, at least 45, at least 50, at least 55, at least 60, at least 65, at least 70, at least 75, or at least 80. In other aspects of this embodiment, an overtube device 20 disclosed herein has at least a portion of the body 30 having a Shore A durometer hardness of, e.g., at most 10, at most 15, at most 20, at most 25, at most 30, at most 35, at most 40, at most 45, at most 50, at most 55, at most 60, at most 65, at most 70, at most 75, or at most 80.

In still other aspects of this embodiment, an overtube device 20 disclosed herein has at least a portion of the body 30 having a Shore A durometer hardness of, e.g., about 10 to about 15, about 10 to about 20, about 10 to about 25, about 10 to about 30, about 10 to about 35, about 10 to about 40, about 10 to about 45, about 10 to about 50, about 10 to about 55, about 10 to about 60, about 10 to about 65, about 10 to about 70, about 10 to about 75, about 10 to about 80, about 15 to about 20, about 15 to about 25, about 15 to about 30, about 15 to about 35, about 15 to about 40, about 15 to about 45, about 15 to about 50, about 15 to about 55, about 15 to about 60, about 15 to about 65, about 15 to about 70, about 15 to about 75, about 15 to about 80, about 20 to about 25, about 20 to about 30, about 20 to about 35, about 20 to about 40, about 20 to about 45, about 20 to about 50, about 20 to about 55, about 20 to about 60, about 20 to about 65, about 20 to about 70, about 20 to about 75, about 20 to about 80, about 25 to about 30, about 25 to about 35, about 25 to about 40, about 25 to about 45, about 25 to about 50, about 25 to about 55, about 25 to about 60, about 25 to about 65, about 25 to about 70, about 25 to about 75, about 25 to about 80, about 30 to about 35, about 30 to about 40, about 30 to about 45, about 30 to about 50, about 30 to about 55, about 30 to about 60, about 30 to about 65, about 30 to about 70, about 30 to about 75, about 30 to about 80, about 35 to about 40, about 35 to about 45, about 35 to about 50, about 35 to about 55, about 35 to about 60, about 35 to about 65, about 35 to about 70, about 35 to about 75, about 35 to about 80, about 40 to about 45, about 40 to about 50, about 40 to about 55, about 40 to about 60, about 40 to about 65, about 40 to about 70, about 40 to about 75, about 40 to about 80, about 45 to about 50, about 45 to about 55, about 45 to about 60, about 45 to about 65, about 45 to about 70, about 45 to about 75, about 45 to about 80, about 50 to about 55, about 50 to about 60, about 50 to about 65, about 50 to about 70, about 50 to about 75, about 50 to about 80, about 55 to about 60, about 55 to about 65, about 55 to about 70, about 55 to about 75, about 55 to about 80, about 60 to about 65, about 60 to about 70, about 60 to about 75, about 60 to about 80, about 65 to about 70, about 65 to about 75, about 65 to about 80, about 70 to about 75, about 70 to about 80, or about 75 to about 80.

With further reference to FIG. 4, it can again be seen that in the exemplary embodiment the primary lumen 60 is formed as a substantially linear interior channel having a relatively larger diameter at the proximal end 22 of the device 20 associated with the proximal portion 42 of the body wall 40 and a relatively smaller diameter at the distal end 24 of the device 20 associated with the distal portion 44 of the body wall 40, with a tapered portion 62 of the primary lumen 60 formed and transitioning between the proximal and distal ends 22, 24 of the device 20. The secondary lumen 70 intersects the primary lumen 60 at an intermediate location, or at a point between the proximal and distal portions 42, 44 of the body wall 40. In the exemplary embodiment, once again, the angle of the secondary lumen 70 to the primary lumen 60 is approximately thirty degrees (30°), with the suction port 50, and here the integral barb fitting 76, extending generally proximally, or in the direction of the proximal end 22 of the device 20, and with the secondary lumen 70 intersecting the primary lumen 60 approximately midway along the length of the primary lumen 60, or in the vicinity of the tapered portion 62. Again, all such geometrical configurations are merely illustrative of features and aspects of the present invention and non-limiting. Notably, the inside diameter 64 of the primary lumen 60 at the distal portion 44 of the body wall 40 is in the exemplary embodiment substantially equivalent to the inside diameter 78 of the secondary lumen 70 that defines the suction port 50. As a result, and as will be further appreciated from the below discussion in conjunction both with FIGS. 5-7 illustrating the assembly of the device 20 with an overtube T and cap C and with FIGS. 8A-8J illustrating the device 20 in use, the substantially constant-diameter flow path through the device 20 from its distal end 24 that is connected to the overtube T to the outlet or proximal opening 72 of the suction port 50 that is connected to the suction system 80 yields an effective suction path having no restrictions and thus not inhibiting any foreign materials being suctioned or removed from passing through the device 20 and into the suction system 80 (FIG. 8G), again, more about which is said below. Relatedly, the relatively gentle bend from the primary lumen 60 to the secondary lumen 70 also cooperates in passing foreign materials through the device. Once more, the substantially continuous and linear primary lumen 60 into which the endoscope N (FIG. 8A) selectively passes from the proximal end 22 to the distal end 24 of the device 20 facilitates insertion and removal of the scope N during use, with the optional tapered portion 62 further facilitating particularly insertion of the scope N, versus there being any abrupt steps or shoulders within the primary lumen 60. And by positioning the secondary lumen 70 so as to intersect the primary lumen 60 at an intermediate location, there is room within the device 20 for retraction of the scope N to a point proximal of the secondary lumen 70 for visualization of the suction event without interfering with the suction event. These and other optional configurations and uses are contemplated as being within the spirit and scope of the present invention, as will be further appreciated from the further discussion regarding the device 20 in use.

Turning now to FIGS. 5-7, there are shown exploded, assembled, and cross-sectional perspective views of the exemplary overtube device 20 of FIGS. 1 and 2 now in conjunction with an illustrative overtube T and related overtube cap C. As shown, the overtube T is configured at its proximal end T1 with a grip portion G that includes a proximal connector G1 having an internal thread G2. Tethered to the grip portion G is an overtube cap C having a proximal end C1 and an opposite distal end C2 formed with an external thread C3 configured to engage the internal thread G2 of the grip portion G. In the exemplary embodiment, then, the overtube device 20 is formed having an external thread 46 on its distal portion 44 configured for selective engagement with the internal thread G2 of the grip portion G and further having an internal thread 36 within the primary lumen 60 at the proximal portion 42 of the device 20 for selective engagement with the external thread C3 of the tethered overtube cap C. As such, it will be appreciated that, as illustrated, the overtube device 20 according to aspects of the present invention is configured to be inserted or installed between the grip portion G of the exemplary overtube T and the overtube cap C thereof, thereby converting such a conventional overtube into a suction or foreign material retrieval device, as further appreciated with reference to FIGS. 8A-8J, discussed below. An intermediate radial flange 48 may be formed on the device 20 just proximal of the distal portion 44 and the external threads 46 to serve as a stop or shoulder against which the grip portion connector G1 may seat when the device 20 is installed thereon. It will again be appreciated that all such structure is exemplary and not limiting. By way of illustration and not limitation, the overtube T and related cap C may be manufactured and sold by US Endoscopy in Mentor, Ohio under the trademark GUARDUS®. The GUARDUS® overtubes currently generally come in two versions: (1) "esophageal" measuring a nominal 25 cm in length and having an outside diameter of 19.5 mm and an inside diameter of 16.7 mm; and (2) "gastric" measuring a nominal 50 cm in length and having an outside diameter of 19.5 mm and an inside diameter of 16.7 mm. In either case (esophageal or gastric GUARDUS® overtube), the cap C may be formed at its proximal end C1 with a wiper gasket C5 positioned within the cap lumen C4 so as to accommodate and seal about endoscopes within a certain size range, namely, in the range of 8.6 to 10.0 mm or in the range of 10.0 to 11.7 mm; similar sizing may be associated with the inner tube V (FIGS. 8A and 8B) that is employed with the main overtube T when initially inserted. In the exemplary GUARDUS® overtube T, the grip portion G is permanently installed on the proximal end T1 of the main or outer overtube T, again with the overtube cap T (sometimes referred to as an "insufflation cap") tethered to the grip portion G so as to effectively be inseparable from the overtube T. The internal thread G2 formed in the grip portion connector G1 and the mating external thread C3 formed on the distal end C2 of the cap C are both sets of four offset thread forms designed for complete engagement in approximately a one-quarter turn. As with all aspects of the exemplary GUARDUS® overtube T, such geometrical and structural configurations are merely illustrative and provide context for disclosure of aspects and features of the present overtube device invention and so are again non-limiting. Staying with the illustrative GUARDUS® overtube T and the above-described thread forms, it would follow that one exemplary embodiment of the overtube device 20 according to aspects of the present invention would entail similar four offset thread forms for the internal and external threads 36, 46 of the device 20 for engagement with the mating structure of the GUARDUS® overtube T. It follows that the related diameters on which the threads 36, 46 are formed would coincide also. Though not shown, an o-ring, washer, or other sealing means now known or later developed may be provided at or in conjunction with any of the component connections, including but not limited to the interface between the device 20 and the grip portion G of the overtube T and the between the device 20 and the overtube cap C. As best shown in FIG. 4 relating to the alternative embodiment, though true of the first exemplary embodiment of FIGS. 1 and 2 as well, once more, the inside diameter 64 of the primary lumen 60 at the distal portion 44 of the body wall 40 is substantially equivalent to the inside diameter 78 of the secondary lumen 70 that defines the suction port 50. Furthermore, in one exemplary embodiment it is preferred that such inside diameters 64, 78 of the device 20 substantially correspond to the inside diameter T3 of the overtube T resulting in a substantially constant-diameter flow path from the overtube T through the device 20. By way of illustration and not limitation, the respective inside diameters 64, 78, T3 may be approximately 16.7 mm, though it will be appreciated by those skilled in the art that a variety of other sizes and size ratios or proportional or relative sizes of the various features are possible without departing from the spirit and scope of the invention. Where the device 20 or any feature thereof is annular or round, it will be appreciated that any reference to "width" is to be understood as the feature's diameter.

Dimensionally, then, in the exemplary embodiment, the width of the primary lumen 60 is, e.g., about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, or about 40 mm. In still further aspects of this embodiment, the width of the primary lumen 60 is, e.g., at least 9 mm, at least 10 mm, at least 11 mm, at least 12 mm, at least 13 mm, at least 14 mm, at least 15 mm, at least 16 mm, at least 17 mm, at least 18 mm, at least 19 mm, at least 20 mm, at least 21 mm, at least 22 mm, at least 23 mm, at least 24 mm, at least 25 mm, at least 26 mm, at least 27 mm, at least 28 mm, at least 29 mm, at least 30 mm, at least 31 mm, at least 32 mm, at least 33 mm, at least 34 mm, at least 35 mm, at least 36 mm, at least 37 mm, at least 38 mm, at least 39 mm, or at least 40 mm. In still further aspects of this embodiment, the width of the primary lumen 60 is, e.g., at most 9 mm, at most 10 mm, at most 11 mm, at most 12 mm, at most 13 mm, at most 14 mm, at most 15 mm, at most 16 mm, at most 17 mm, at most 18 mm, at most 19 mm, at most 20 mm, at most 21 mm, at most 22 mm, at most 23 mm, at most 24 mm, at most 25 mm, at most 26 mm, at most 27 mm, at most 28 mm, at most 29 mm, at most 30 mm, at most 31 mm, at most 32 mm, at most 33 mm, at most 34 mm, at most 35 mm, at most 36 mm, at most 37 mm, at most 38 mm, at most 39 mm, or at most 40 mm.

In other aspects of this embodiment, in an overtube device 20 disclosed herein the width of the primary lumen 60 is, e.g., about 9 mm to about 10 mm, about 9 mm to about 11 mm, about 9 mm to about 12 mm, about 9 mm to about 13 mm, about 9 mm to about 14 mm, about 9 mm to about 15 mm, about 9 mm to about 16 mm, about 9 mm to about 17 mm, about 9 mm to about 18 mm, about 9 mm to about 19 mm, about 9 mm to about 20 mm, about 9 mm to about 21 mm, about 9 mm to about 22 mm, about 9 mm to about 23 mm, about 9 mm to about 24 mm, about 9 mm to about 25 mm, about 9 mm to about 26 mm, about 9 mm to about 27 mm, about 9 mm to about 28 mm, about 9 mm to about 29 mm, about 9 mm to about 30 mm, about 9 mm to about 31 mm, about 9 mm to about 32 mm, about 9 mm to about 33 mm, about 9 mm to about 34 mm, about 9 mm to about 35 mm, about 9 mm to about 36 mm, about 9 mm to about 37 mm, about 9 mm to about 38 mm, about 9 mm to about 39 mm, about 9 mm to about 40 mm, about 10 mm to about 11 mm, about 10 mm to about 12 mm, about 10 mm to about 13 mm, about 10 mm to about 14 mm, about 10 mm to about 15 mm, about 10 mm to about 16 mm, about 10 mm to about 17 mm, about 10 mm to about 18 mm, about 10 mm to about 19 mm, about 10 mm to about 20 mm, about 10 mm to about 21 mm, about 10 mm to about 22 mm, about 10 mm to about 23 mm, about 10 mm to about 24 mm, about 10 mm to about 25 mm, about 10 mm to about 26 mm, about 10 mm to about 27 mm, about 10 mm to about 28 mm, about 10 mm to about 29 mm, about 10 mm to about 30 mm, about 10 mm to about 31 mm, about 10 mm to about 32 mm, about 10 mm to about 33 mm, about 10 mm to about 34 mm, about 10 mm to about 35 mm, about 10 mm to about 36 mm, about 10 mm to about 37 mm, about 10 mm to about 38 mm, about 10 mm to about 39 mm, about 10 mm to about 40 mm, about 11 mm to about 12 mm, about 11 mm to about 13 mm, about 11 mm to about 14 mm, about 11 mm to about 15 mm, about 11 mm to about 16 mm, about 11 mm to about 17 mm, about 11 mm to about 18 mm, about 11 mm to about 19 mm, about 11 mm to about 20 mm, about 11 mm to about 21 mm, about 11 mm to about 22 mm, about 11 mm to about 23 mm, about 11 mm to about 24 mm, about 11 mm to about 25 mm, about 11 mm to about 26 mm, about 11 mm to about 27 mm, about 11 mm to about 28 mm, about 11 mm to about 29 mm, about 11 mm to about 30 mm, about 11 mm to about 31 mm, about 11 mm to about 32 mm, about 11 mm to about 33 mm, about 11 mm to about 34 mm, about 11 mm to about 35 mm, about 11 mm to about 36 mm, about 11 mm to about 37 mm, about 11 mm to about 38 mm, about 11 mm to about 39 mm, about 11 mm to about 40 mm, about 12 mm to about 13 mm, about 12 mm to about 14 mm, about 12 mm to about 15 mm, about 12 mm to about 16 mm, about 12 mm to about 17 mm, about 12 mm to about 18 mm, about 12 mm to about 19 mm, about 12 mm to about 20 mm, about 12 mm to about 21 mm, about 12 mm to about 22 mm, about 12 mm to about 23 mm, about 12 mm to about 24 mm, about 12 mm to about 25 mm, about 12 mm to about 26 mm, about 12 mm to about 27 mm, about 12 mm to about 28 mm, about 12 mm to about 29 mm, about 12 mm to about 30 mm, about 12 mm to about 31 mm, about 12 mm to about 32 mm, about 12 mm to about 33 mm, about 12 mm to about 34 mm, about 12 mm to about 35 mm, about 12 mm to about 36 mm, about 12 mm to about 37 mm, about 12 mm to about 38 mm, about 12 mm to about 39 mm, about 12 mm to about 40 mm, about 13 mm to about 14 mm, about 13 mm to about 15 mm, about 13 mm to about 16 mm, about 13 mm to about 17 mm, about 13 mm to about 18 mm, about 13 mm to about 19 mm, about 13 mm to about 20 mm, about 13 mm to about 21 mm, about 13 mm to about 22 mm, about 13 mm to about 23 mm, about 13 mm to about 24 mm, about 13 mm to about 25 mm, about 13 mm to about 26 mm, about 13 mm to about 27 mm, about 13 mm to about 28 mm, about 13 mm to about 29 mm, about 13 mm to about 30 mm, about 13 mm to about 31 mm, about 13 mm to about 32 mm, about 13 mm to about 33 mm, about 13 mm to about 34 mm, about 13 mm to about 35 mm, about 13 mm to about 36 mm, about 13 mm to about 37 mm, about 13 mm to about 38 mm, about 13 mm to about 39 mm, about 13 mm to about 40 mm, about 14 mm to about 15 mm, about 14 mm to about 16 mm, about 14 mm to about 17 mm, about 14 mm to about 18 mm, about 14 mm to about 19 mm, about 14 mm to about 20 mm, about 14 mm to about 21 mm, about 14 mm to about 22 mm, about 14 mm to about 23 mm, about 14 mm to about 24 mm, about 14 mm to about 25 mm, about 14 mm to about 26 mm, about 14 mm to about 27 mm, about 14 mm to about 28 mm, about 14 mm to about 29 mm, about 14 mm to about 30 mm, about 14 mm to about 31 mm, about 14 mm to about 32 mm, about 14 mm to about 33 mm, about 14 mm to about 34 mm, about 14 mm to about 35 mm, about 14 mm to about 36 mm, about 14 mm to about 37 mm, about 14 mm to about 38 mm, about 14 mm to about 39 mm, about 14 mm to about 40 mm, about 15 mm to about 16 mm, about 15 mm to about 17 mm, about 15 mm to about 18 mm, about 15 mm to about 19 mm, about 15 mm to about 20 mm, about 15 mm to about 21 mm, about 15 mm to about 22 mm, about 15 mm to about 23 mm, about 15 mm to about 24 mm, about 15 mm to about 25 mm, about 15 mm to about 26 mm, about 15 mm to about 27 mm, about 15 mm to about 28 mm, about 15 mm to about 29 mm, about 15 mm to about 30 mm, about 15 mm to about 31 mm, about 15 mm to about 32 mm, about 15 mm to about 33 mm, about 15 mm to about 34 mm, about 15 mm to about 35 mm, about 15 mm to about 36 mm, about 15 mm to about 37 mm, about 15 mm to about 38 mm, about 15 mm to about 39 mm, about 15 mm to about 40 mm, about 16 mm to about 17 mm, about 16 mm to about 18 mm, about 16 mm to about 19 mm, about 16 mm to about 20 mm, about 16 mm to about 21 mm, about 16 mm to about 22 mm, about 16 mm to about 23 mm, about 16 mm to about 24 mm, about 16 mm to about 25 mm, about 16 mm to about 26 mm, about 16 mm to about 27 mm, about 16 mm to about 28 mm, about 16 mm to about 29 mm, about 16 mm to about 30 mm, about 16 mm to about 31 mm, about 16 mm to about 32 mm, about 16 mm to about 33 mm, about 16 mm to about 34 mm, about 16 mm to about 35 mm, about 16 mm to about 36 mm, about 16 mm to about 37 mm, about 16 mm to about 38 mm, about 16 mm to about 39 mm, about 16 mm to about 40 mm, about 17 mm to about 18 mm, about 17 mm to about 19 mm, about 17 mm to about 20 mm, about 17 mm to about 21 mm, about 17 mm to about 22 mm, about 17 mm to about 23 mm, about 17 mm to about 24 mm, about 17 mm to about 25 mm, about 17 mm to about 26 mm, about 17 mm to about 27 mm, about 17 mm to about 28 mm, about 17 mm to about 29 mm, about 17 mm to about 30 mm, about 17 mm to about 31 mm, about 17 mm to about 32 mm, about 17 mm to about 33 mm, about 17 mm to about 34 mm, about 17 mm to about 35 mm, about 17 mm to about 36 mm, about 17 mm to about 37 mm, about 17 mm to about 38 mm, about 17 mm to about 39 mm, about 17 mm to about 40 mm, about 18 mm to about 19 mm, about 18 mm to about 20 mm, about 18 mm to about 21 mm, about 18 mm to about 22 mm, about 18 mm to about 23 mm, about 18 mm to about 24 mm, about 18 mm to about 25 mm, about 18 mm to about 26 mm, about 18 mm to about 27 mm, about 18 mm to about 28 mm, about 18 mm to about 29 mm, about 18 mm to about 30 mm, about 18 mm to about 31 mm, about 18 mm to about 32 mm, about 18 mm to about 33 mm, about 18 mm to about 34 mm, about 18 mm to about 35 mm, about 18 mm to about 36 mm, about 18 mm to about 37 mm, about 18 mm to about 38 mm, about 18 mm to about 39 mm, about 18 mm to about 40 mm, about 19 mm to about 20 mm, about 19 mm to about 21 mm, about 19 mm to about 22 mm, about 19 mm to about 23 mm, about 19 mm to about 24 mm, about 19 mm to about 25 mm, about 19 mm to about 26 mm, about 19 mm to about 27 mm, about 19 mm to about 28 mm, about 19 mm to about 29 mm, about 19 mm to about 30 mm, about 19 mm to about 31 mm, about 19 mm to about 32 mm, about 19 mm to about 33 mm, about 19 mm to about 34 mm, about 19 mm to about 35 mm, about 19 mm to about 36 mm, about 19 mm to about 37 mm, about 19 mm to about 38 mm, about 19 mm to about 39 mm, about 19 mm to about 40 mm, about 20 mm to about 21 mm, about 20 mm to about 22 mm, about 20 mm to about 23 mm, about 20 mm to about 24 mm, about 20 mm to about 25 mm, about 20 mm to about 26 mm, about 20 mm to about 27 mm, about 20 mm to about 28 mm, about 20 mm to about 29 mm, about 20 mm to about 30 mm, about 20 mm to about 31 mm, about 20 mm to about 32 mm, about 20 mm to about 33 mm, about 20 mm to about 34 mm, about 20 mm to about 35 mm, about 20 mm to about 36 mm, about 20 mm to about 37 mm, about 20 mm to about 38 mm, about 20 mm to about 39 mm, about 20 mm to about 40 mm, about 21 mm to about 22 mm, about 21 mm to about 23 mm, about 21 mm to about 24 mm, about 21 mm to about 25 mm, about 21 mm to about 26 mm, about 21 mm to about 27 mm, about 21 mm to about 28 mm, about 21 mm to about 29 mm, about 21 mm to about 30 mm, about 21 mm to about 31 mm, about 21 mm to about 32 mm, about 21 mm to about 33 mm, about 21 mm to about 34 mm, about 21 mm to about 35 mm, about 21 mm to about 36 mm, about 21 mm to about 37 mm, about 21 mm to about 38 mm, about 21 mm to about 39 mm, about 21 mm to about 40 mm, about 22 mm to about 23 mm, about 22 mm to about 24 mm, about 22 mm to about 25 mm, about 22 mm to about 26 mm, about 22 mm to about 27 mm, about 22 mm to about 28 mm, about 22 mm to about 29 mm, about 22 mm to about 30 mm, about 22 mm to about 31 mm, about 22 mm to about 32 mm, about 22 mm to about 33 mm, about 22 mm to about 34 mm, about 22 mm to about 35 mm, about 22 mm to about 36 mm, about 22 mm to about 37 mm, about 22 mm to about 38 mm, about 22 mm to about 39 mm, about 22 mm to about 40 mm, about 23 mm to about 24 mm, about 23 mm to about 25 mm, about 23 mm to about 26 mm, about 23 mm to about 27 mm, about 23 mm to about 28 mm, about 23 mm to about 29 mm, about 23 mm to about 30 mm, about 23 mm to about 31 mm, about 23 mm to about 32 mm, about 23 mm to about 33 mm, about 23 mm to about 34 mm, about 23 mm to about 35 mm, about 23 mm to about 36 mm, about 23 mm to about 37 mm, about 23 mm to about 38 mm, about 23 mm to about 39 mm, about 23 mm to about 40 mm, about 24 mm to about 25 mm, about 24 mm to about 26 mm, about 24 mm to about 27 mm, about 24 mm to about 28 mm, about 24 mm to about 29 mm, about 24 mm to about 30 mm, about 24 mm to about 31 mm, about 24 mm to about 32 mm, about 24 mm to about 33 mm, about 24 mm to about 34 mm, about 24 mm to about 35 mm, about 24 mm to about 36 mm, about 24 mm to about 37 mm, about 24 mm to about 38 mm, about 24 mm to about 39 mm, about 24 mm to about 40 mm, about 25 mm to about 26 mm, about 25 mm to about 27 mm, about 25 mm to about 28 mm, about 25 mm to about 29 mm, about 25 mm to about 30 mm, about 25 mm to about 31 mm, about 25 mm to about 32 mm, about 25 mm to about 33 mm, about 25 mm to about 34 mm, about 25 mm to about 35 mm, about 25 mm to about 36 mm, about 25 mm to about 37 mm, about 25 mm to about 38 mm, about 25 mm to about 39 mm, about 25 mm to about 40 mm, about 26 mm to about 27 mm, about 26 mm to about 28 mm, about 26 mm to about 29 mm, about 26 mm to about 30 mm, about 26 mm to about 31 mm, about 26 mm to about 32 mm, about 26 mm to about 33 mm, about 26 mm to about 34 mm, about 26 mm to about 35 mm, about 26 mm to about 36 mm, about 26 mm to about 37 mm, about 26 mm to about 38 mm, about 26 mm to about 39 mm, about 26 mm to about 40 mm, about 27 mm to about 28 mm, about 27 mm to about 29 mm, about 27 mm to about 30 mm, about 27 mm to about 31 mm, about 27 mm to about 32 mm, about 27 mm to about 33 mm, about 27 mm to about 34 mm, about 27 mm to about 35 mm, about 27 mm to about 36 mm, about 27 mm to about 37 mm, about 27 mm to about 38 mm, about 27 mm to about 39 mm, about 27 mm to about 40 mm, about 28 mm to about 29 mm, about 28 mm to about 30 mm, about 28 mm to about 31 mm, about 28 mm to about 32 mm, about 28 mm to about 33 mm, about 28 mm to about 34 mm, about 28 mm to about 35 mm, about 28 mm to about 36 mm, about 28 mm to about 37 mm, about 28 mm to about 38 mm, about 28 mm to about 39 mm, about 28 mm to about 40 mm, about 29 mm to about 30 mm, about 29 mm to about 31 mm, about 29 mm to about 32 mm, about 29 mm to about 33 mm, about 29 mm to about 34 mm, about 29 mm to about 35 mm, about 29 mm to about 36 mm, about 29 mm to about 37 mm, about 29 mm to about 38 mm, about 29 mm to about 39 mm, about 29 mm to about 40 mm, about 30 mm to about 31 mm, about 30 mm to about 32 mm, about 30 mm to about 33 mm, about 30 mm to about 34 mm, about 30 mm to about 35 mm, about 30 mm to about 36 mm, about 30 mm to about 37 mm, about 30 mm to about 38 mm, about 30 mm to about 39 mm, about 30 mm to about 40 mm, about 31 mm to about 32 mm, about 31 mm to about 33 mm, about 31 mm to about 34 mm, about 31 mm to about 35 mm, about 31 mm to about 36 mm, about 31 mm to about 37 mm, about 31 mm to about 38 mm, about 31 mm to about 39 mm, about 31 mm to about 40 mm, about 32 mm to about 33 mm, about 32 mm to about 34 mm, about 32 mm to about 35 mm, about 32 mm to about 36 mm, about 32 mm to about 37 mm, about 32 mm to about 38 mm, about 32 mm to about 39 mm, about 32 mm to about 40 mm, about 33 mm to about 34 mm, about 33 mm to about 35 mm, about 33 mm to about 36 mm, about 33 mm to about 37 mm, about 33 mm to about 38 mm, about 33 mm to about 39 mm, about 33 mm to about 40 mm, about 34 mm to about 35 mm, about 34 mm to about 36 mm, about 34 mm to about 37 mm, about 34 mm to about 38 mm, about 34 mm to about 39 mm, about 34 mm to about 40 mm, about 35 mm to about 36 mm, about 35 mm to about 37 mm, about 35 mm to about 38 mm, about 35 mm to about 39 mm, about 35 mm to about 40 mm, about 36 mm to about 37 mm, about 36 mm to about 38 mm, about 36 mm to about 39 mm, about 36 mm to about 40 mm, about 37 mm to about 38 mm, about 37 mm to about 39 mm, about 37 mm to about 40 mm, about 38 mm to about 39 mm, about 38 mm to about 40 mm, or about 39 mm to about 40 mm.

In other aspects of this embodiment, in an overtube device 20 disclosed herein the width of the secondary lumen 70 is, e.g., about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, or about 40 mm. In still further aspects of this embodiment, the width of the secondary lumen 70 is, e.g., at least 5 mm, at least 6 mm, at least 7 mm, at least 8 mm, at least 9 mm, at least 10 mm, at least 11 mm, at least 12 mm, at least 13 mm, at least 14 mm, at least 15 mm, at least 16 mm, at least 17 mm, at least 18 mm, at least 19 mm, at least 20 mm, at least 21 mm, at least 22 mm, at least 23 mm, at least 24 mm, at least 25 mm, at least 26 mm, at least 27 mm, at least 28 mm, at least 29 mm, at least 30 mm, at least 31 mm, at least 32 mm, at least 33 mm, at least 34 mm, at least 35 mm, at least 36 mm, at least 37 mm, at least 38 mm, at least 39 mm, or at least 40 mm. In still further aspects of this embodiment, the width of the primary lumen 60 is, e.g., at most 5 mm, at most 6 mm, at most 7 mm, at most 8 mm, at most 9 mm, at most 10 mm, at most 11 mm, at most 12 mm, at most 13 mm, at most 14 mm, at most 15 mm, at most 16 mm, at most 17 mm, at most 18 mm, at most 19 mm, at most 20 mm, at most 21 mm, at most 22 mm, at most 23 mm, at most 24 mm, at most 25 mm, at most 26 mm, at most 27 mm, at most 28 mm, at most 29 mm, at most 30 mm, at most 31 mm, at most 32 mm, at most 33 mm, at most 34 mm, at most 35 mm, at most 36 mm, at most 37 mm, at most 38 mm, at most 39 mm, or at most 40 mm.

In still other aspects of this embodiment, in an overtube device 20 disclosed herein the width of the secondary lumen 70 is, e.g., about 5 mm to about 6 mm, about 5 mm to about 7 mm, about 5 mm to about 8 mm, about 5 mm to about 9 mm, about 5 mm to about 10 mm, about 5 mm to about 11 mm, about 5 mm to about 12 mm, about 5 mm to about 13 mm, about 5 mm to about 14 mm, about 5 mm to about 15 mm, about 5 mm to about 16 mm, about 5 mm to about 17 mm, about 5 mm to about 18 mm, about 5 mm to about 19 mm, about 5 mm to about 20 mm, about 5 mm to about 21 mm, about 5 mm to about 22 mm, about 5 mm to about 23 mm, about 5 mm to about 24 mm, about 5 mm to about 25 mm, about 5 mm to about 26 mm, about 5 mm to about 27 mm, about 5 mm to about 28 mm, about 5 mm to about 29 mm, about 5 mm to about 30 mm, about 5 mm to about 31 mm, about 5 mm to about 32 mm, about 5 mm to about 33 mm, about 5 mm to about 34 mm, about 5 mm to about 35 mm, about 5 mm to about 36 mm, about 5 mm to about 37 mm, about 5 mm to about 38 mm, about 5 mm to about 39 mm, about 5 mm to about 40 mm, about 6 mm to about 7 mm, about 6 mm to about 8 mm, about 6 mm to about 9 mm, about 6 mm to about 10 mm, about 6 mm to about 11 mm, about 6 mm to about 12 mm, about 6 mm to about 13 mm, about 6 mm to about 14 mm, about 6 mm to about 15 mm, about 6 mm to about 16 mm, about 6 mm to about 17 mm, about 6 mm to about 18 mm, about 6 mm to about 19 mm, about 6 mm to about 20 mm, about 6 mm to about 21 mm, about 6 mm to about 22 mm, about 6 mm to about 23 mm, about 6 mm to about 24 mm, about 6 mm to about 25 mm, about 6 mm to about 26 mm, about 6 mm to about 27 mm, about 6 mm to about 28 mm, about 6 mm to about 29 mm, about 6 mm to about 30 mm, about 6 mm to about 31 mm, about 6 mm to about 32 mm, about 6 mm to about 33 mm, about 6 mm to about 34 mm, about 6 mm to about 35 mm, about 6 mm to about 36 mm, about 6 mm to about 37 mm, about 6 mm to about 38 mm, about 6 mm to about 39 mm, about 6 mm to about 40 mm, about 7 mm to about 8 mm, about 7 mm to about 9 mm, about 7 mm to about 10 mm, about 7 mm to about 11 mm, about 7 mm to about 12 mm, about 7 mm to about 13 mm, about 7 mm to about 14 mm, about 7 mm to about 15 mm, about 7 mm to about 16 mm, about 7 mm to about 17 mm, about 7 mm to about 18 mm, about 7 mm to about 19 mm, about 7 mm to about 20 mm, about 7 mm to about 21 mm, about 7 mm to about 22 mm, about 7 mm to about 23 mm, about 7 mm to about 24 mm, about 7 mm to about 25 mm, about 7 mm to about 26 mm, about 7 mm to about 27 mm, about 7 mm to about 28 mm, about 7 mm to about 29 mm, about 7 mm to about 30 mm, about 7 mm to about 31 mm, about 7 mm to about 32 mm, about 7 mm to about 33 mm, about 7 mm to about 34 mm, about 7 mm to about 35 mm, about 7 mm to about 36 mm, about 7 mm to about 37 mm, about 7 mm to about 38 mm, about 7 mm to about 39 mm, about 7 mm to about 40 mm, about 8 mm to about 9 mm, about 8 mm to about 10 mm, about 8 mm to about 11 mm, about 8 mm to about 12 mm, about 8 mm to about 13 mm, about 8 mm to about 14 mm, about 8 mm to about 15 mm, about 8 mm to about 16 mm, about 8 mm to about 17 mm, about 8 mm to about 18 mm, about 8 mm to about 19 mm, about 8 mm to about 20 mm, about 8 mm to about 21 mm, about 8 mm to about 22 mm, about 8 mm to about 23 mm, about 8 mm to about 24 mm, about 8 mm to about 25 mm, about 8 mm to about 26 mm, about 8 mm to about 27 mm, about 8 mm to about 28 mm, about 8 mm to about 29 mm, about 8 mm to about 30 mm, about 8 mm to about 31 mm, about 8 mm to about 32 mm, about 8 mm to about 33 mm, about 8 mm to about 34 mm, about 8 mm to about 35 mm, about 8 mm to about 36 mm, about 8 mm to about 37 mm, about 8 mm to about 38 mm, about 8 mm to about 39 mm, about 8 mm to about 40 mm, about 9 mm to about 10 mm, about 9 mm to about 11 mm, about 9 mm to about 12 mm, about 9 mm to about 13 mm, about 9 mm to about 14 mm, about 9 mm to about 15 mm, about 9 mm to about 16 mm, about 9 mm to about 17 mm, about 9 mm to about 18 mm, about 9 mm to about 19 mm, about 9 mm to about 20 mm, about 9 mm to about 21 mm, about 9 mm to about 22 mm, about 9 mm to about 23 mm, about 9 mm to about 24 mm, about 9 mm to about 25 mm, about 9 mm to about 26 mm, about 9 mm to about 27 mm, about 9 mm to about 28 mm, about 9 mm to about 29 mm, about 9 mm to about 30 mm, about 9 mm to about 31 mm, about 9 mm to about 32 mm, about 9 mm to about 33 mm, about 9 mm to about 34 mm, about 9 mm to about 35 mm, about 9 mm to about 36 mm, about 9 mm to about 37 mm, about 9 mm to about 38 mm, about 9 mm to about 39 mm, about 9 mm to about 40 mm, about 10 mm to about 11 mm, about 10 mm to about 12 mm, about 10 mm to about 13 mm, about 10 mm to about 14 mm, about 10 mm to about 15 mm, about 10 mm to about 16 mm, about 10 mm to about 17 mm, about 10 mm to about 18 mm, about 10 mm to about 19 mm, about 10 mm to about 20 mm, about 10 mm to about 21 mm, about 10 mm to about 22 mm, about 10 mm to about 23 mm, about 10 mm to about 24 mm, about 10 mm to about 25 mm, about 10 mm to about 26 mm, about 10 mm to about 27 mm, about 10 mm to about 28 mm, about 10 mm to about 29 mm, about 10 mm to about 30 mm, about 10 mm to about 31 mm, about 10 mm to about 32 mm, about 10 mm to about 33 mm, about 10 mm to about 34 mm, about 10 mm to about 35 mm, about 10 mm to about 36 mm, about 10 mm to about 37 mm, about 10 mm to about 38 mm, about 10 mm to about 39 mm, about 10 mm to about 40 mm, about 11 mm to about 12 mm, about 11 mm to about 13 mm, about 11 mm to about 14 mm, about 11 mm to about 15 mm, about 11 mm to about 16 mm, about 11 mm to about 17 mm, about 11 mm to about 18 mm, about 11 mm to about 19 mm, about 11 mm to about 20 mm, about 11 mm to about 21 mm, about 11 mm to about 22 mm, about 11 mm to about 23 mm, about 11 mm to about 24 mm, about 11 mm to about 25 mm, about 11 mm to about 26 mm, about 11 mm to about 27 mm, about 11 mm to about 28 mm, about 11 mm to about 29 mm, about 11 mm to about 30 mm, about 11 mm to about 31 mm, about 11 mm to about 32 mm, about 11 mm to about 33 mm, about 11 mm to about 34 mm, about 11 mm to about 35 mm, about 11 mm to about 36 mm, about 11 mm to about 37 mm, about 11 mm to about 38 mm, about 11 mm to about 39 mm, about 11 mm to about 40 mm, about 12 mm to about 13 mm, about 12 mm to about 14 mm, about 12 mm to about 15 mm, about 12 mm to about 16 mm, about 12 mm to about 17 mm, about 12 mm to about 18 mm, about 12 mm to about 19 mm, about 12 mm to about 20 mm, about 12 mm to about 21 mm, about 12 mm to about 22 mm, about 12 mm to about 23 mm, about 12 mm to about 24 mm, about 12 mm to about 25 mm, about 12 mm to about 26 mm, about 12 mm to about 27 mm, about 12 mm to about 28 mm, about 12 mm to about 29 mm, about 12 mm to about 30 mm, about 12 mm to about 31 mm, about 12 mm to about 32 mm, about 12 mm to about 33 mm, about 12 mm to about 34 mm, about 12 mm to about 35 mm, about 12 mm to about 36 mm, about 12 mm to about 37 mm, about 12 mm to about 38 mm, about 12 mm to about 39 mm, about 12 mm to about 40 mm, about 13 mm to about 14 mm, about 13 mm to about 15 mm, about 13 mm to about 16 mm, about 13 mm to about 17 mm, about 13 mm to about 18 mm, about 13 mm to about 19 mm, about 13 mm to about 20 mm, about 13 mm to about 21 mm, about 13 mm to about 22 mm, about 13 mm to about 23 mm, about 13 mm to about 24 mm, about 13 mm to about 25 mm, about 13 mm to about 26 mm, about 13 mm to about 27 mm, about 13 mm to about 28 mm, about 13 mm to about 29 mm, about 13 mm to about 30 mm, about 13 mm to about 31 mm, about 13 mm to about 32 mm, about 13 mm to about 33 mm, about 13 mm to about 34 mm, about 13 mm to about 35 mm, about 13 mm to about 36 mm, about 13 mm to about 37 mm, about 13 mm to about 38 mm, about 13 mm to about 39 mm, about 13 mm to about 40 mm, about 14 mm to about 15 mm, about 14 mm to about 16 mm, about 14 mm to about 17 mm, about 14 mm to about 18 mm, about 14 mm to about 19 mm, about 14 mm to about 20 mm, about 14 mm to about 21 mm, about 14 mm to about 22 mm, about 14 mm to about 23 mm, about 14 mm to about 24 mm, about 14 mm to about 25 mm, about 14 mm to about 26 mm, about 14 mm to about 27 mm, about 14 mm to about 28 mm, about 14 mm to about 29 mm, about 14 mm to about 30 mm, about 14 mm to about 31 mm, about 14 mm to about 32 mm, about 14 mm to about 33 mm, about 14 mm to about 34 mm, about 14 mm to about 35 mm, about 14 mm to about 36 mm, about 14 mm to about 37 mm, about 14 mm to about 38 mm, about 14 mm to about 39 mm, about 14 mm to about 40 mm, about 15 mm to about 16 mm, about 15 mm to about 17 mm, about 15 mm to about 18 mm, about 15 mm to about 19 mm, about 15 mm to about 20 mm, about 15 mm to about 21 mm, about 15 mm to about 22 mm, about 15 mm to about 23 mm, about 15 mm to about 24 mm, about 15 mm to about 25 mm, about 15 mm to about 26 mm, about 15 mm to about 27 mm, about 15 mm to about 28 mm, about 15 mm to about 29 mm, about 15 mm to about 30 mm, about 15 mm to about 31 mm, about 15 mm to about 32 mm, about 15 mm to about 33 mm, about 15 mm to about 34 mm, about 15 mm to about 35 mm, about 15 mm to about 36 mm, about 15 mm to about 37 mm, about 15 mm to about 38 mm, about 15 mm to about 39 mm, about 15 mm to about 40 mm, about 16 mm to about 17 mm, about 16 mm to about 18 mm, about 16 mm to about 19 mm, about 16 mm to about 20 mm, about 16 mm to about 21 mm, about 16 mm to about 22 mm, about 16 mm to about 23 mm, about 16 mm to about 24 mm, about 16 mm to about 25 mm, about 16 mm to about 26 mm, about 16 mm to about 27 mm, about 16 mm to about 28 mm, about 16 mm to about 29 mm, about 16 mm to about 30 mm, about 16 mm to about 31 mm, about 16 mm to about 32 mm, about 16 mm to about 33 mm, about 16 mm to about 34 mm, about 16 mm to about 35 mm, about 16 mm to about 36 mm, about 16 mm to about 37 mm, about 16 mm to about 38 mm, about 16 mm to about 39 mm, about 16 mm to about 40 mm, about 17 mm to about 18 mm, about 17 mm to about 19 mm, about 17 mm to about 20 mm, about 17 mm to about 21 mm, about 17 mm to about 22 mm, about 17 mm to about 23 mm, about 17 mm to about 24 mm, about 17 mm to about 25 mm, about 17 mm to about 26 mm, about 17 mm to about 27 mm, about 17 mm to about 28 mm, about 17 mm to about 29 mm, about 17 mm to about 30 mm, about 17 mm to about 31 mm, about 17 mm to about 32 mm, about 17 mm to about 33 mm, about 17 mm to about 34 mm, about 17 mm to about 35 mm, about 17 mm to about 36 mm, about 17 mm to about 37 mm, about 17 mm to about 38 mm, about 17 mm to about 39 mm, about 17 mm to about 40 mm, about 18 mm to about 19 mm, about 18 mm to about 20 mm, about 18 mm to about 21 mm, about 18 mm to about 22 mm, about 18 mm to about 23 mm, about 18 mm to about 24 mm, about 18 mm to about 25 mm, about 18 mm to about 26 mm, about 18 mm to about 27 mm, about 18 mm to about 28 mm, about 18 mm to about 29 mm, about 18 mm to about 30 mm, about 18 mm to about 31 mm, about 18 mm to about 32 mm, about 18 mm to about 33 mm, about 18 mm to about 34 mm, about 18 mm to about 35 mm, about 18 mm to about 36 mm, about 18 mm to about 37 mm, about 18 mm to about 38 mm, about 18 mm to about 39 mm, about 18 mm to about 40 mm, about 19 mm to about 20 mm, about 19 mm to about 21 mm, about 19 mm to about 22 mm, about 19 mm to about 23 mm, about 19 mm to about 24 mm, about 19 mm to about 25 mm, about 19 mm to about 26 mm, about 19 mm to about 27 mm, about 19 mm to about 28 mm, about 19 mm to about 29 mm, about 19 mm to about 30 mm, about 19 mm to about 31 mm, about 19 mm to about 32 mm, about 19 mm to about 33 mm, about 19 mm to about 34 mm, about 19 mm to about 35 mm, about 19 mm to about 36 mm, about 19 mm to about 37 mm, about 19 mm to about 38 mm, about 19 mm to about 39 mm, about 19 mm to about 40 mm, about 20 mm to about 21 mm, about 20 mm to about 22 mm, about 20 mm to about 23 mm, about 20 mm to about 24 mm, about 20 mm to about 25 mm, about 20 mm to about 26 mm, about 20 mm to about 27 mm, about 20 mm to about 28 mm, about 20 mm to about 29 mm, about 20 mm to about 30 mm, about 20 mm to about 31 mm, about 20 mm to about 32 mm, about 20 mm to about 33 mm, about 20 mm to about 34 mm, about 20 mm to about 35 mm, about 20 mm to about 36 mm, about 20 mm to about 37 mm, about 20 mm to about 38 mm, about 20 mm to about 39 mm, about 20 mm to about 40 mm, about 21 mm to about 22 mm, about 21 mm to about 23 mm, about 21 mm to about 24 mm, about 21 mm to about 25 mm, about 21 mm to about 26 mm, about 21 mm to about 27 mm, about 21 mm to about 28 mm, about 21 mm to about 29 mm, about 21 mm to about 30 mm, about 21 mm to about 31 mm, about 21 mm to about 32 mm, about 21 mm to about 33 mm, about 21 mm to about 34 mm, about 21 mm to about 35 mm, about 21 mm to about 36 mm, about 21 mm to about 37 mm, about 21 mm to about 38 mm, about 21 mm to about 39 mm, about 21 mm to about 40 mm, about 22 mm to about 23 mm, about 22 mm to about 24 mm, about 22 mm to about 25 mm, about 22 mm to about 26 mm, about 22 mm to about 27 mm, about 22 mm to about 28 mm, about 22 mm to about 29 mm, about 22 mm to about 30 mm, about 22 mm to about 31 mm, about 22 mm to about 32 mm, about 22 mm to about 33 mm, about 22 mm to about 34 mm, about 22 mm to about 35 mm, about 22 mm to about 36 mm, about 22 mm to about 37 mm, about 22 mm to about 38 mm, about 22 mm to about 39 mm, about 22 mm to about 40 mm, about 23 mm to about 24 mm, about 23 mm to about 25 mm, about 23 mm to about 26 mm, about 23 mm to about 27 mm, about 23 mm to about 28 mm, about 23 mm to about 29 mm, about 23 mm to about 30 mm, about 23 mm to about 31 mm, about 23 mm to about 32 mm, about 23 mm to about 33 mm, about 23 mm to about 34 mm, about 23 mm to about 35 mm, about 23 mm to about 36 mm, about 23 mm to about 37 mm, about 23 mm to about 38 mm, about 23 mm to about 39 mm, about 23 mm to about 40 mm, about 24 mm to about 25 mm, about 24 mm to about 26 mm, about 24 mm to about 27 mm, about 24 mm to about 28 mm, about 24 mm to about 29 mm, about 24 mm to about 30 mm, about 24 mm to about 31 mm, about 24 mm to about 32 mm, about 24 mm to about 33 mm, about 24 mm to about 34 mm, about 24 mm to about 35 mm, about 24 mm to about 36 mm, about 24 mm to about 37 mm, about 24 mm to about 38 mm, about 24 mm to about 39 mm, about 24 mm to about 40 mm, about 25 mm to about 26 mm, about 25 mm to about 27 mm, about 25 mm to about 28 mm, about 25 mm to about 29 mm, about 25 mm to about 30 mm, about 25 mm to about 31 mm, about 25 mm to about 32 mm, about 25 mm to about 33 mm, about 25 mm to about 34 mm, about 25 mm to about 35 mm, about 25 mm to about 36 mm, about 25 mm to about 37 mm, about 25 mm to about 38 mm, about 25 mm to about 39 mm, about 25 mm to about 40 mm, about 26 mm to about 27 mm, about 26 mm to about 28 mm, about 26 mm to about 29 mm, about 26 mm to about 30 mm, about 26 mm to about 31 mm, about 26 mm to about 32 mm, about 26 mm to about 33 mm, about 26 mm to about 34 mm, about 26 mm to about 35 mm, about 26 mm to about 36 mm, about 26 mm to about 37 mm, about 26 mm to about 38 mm, about 26 mm to about 39 mm, about 26 mm to about 40 mm, about 27 mm to about 28 mm, about 27 mm to about 29 mm, about 27 mm to about 30 mm, about 27 mm to about 31 mm, about 27 mm to about 32 mm, about 27 mm to about 33 mm, about 27 mm to about 34 mm, about 27 mm to about 35 mm, about 27 mm to about 36 mm, about 27 mm to about 37 mm, about 27 mm to about 38 mm, about 27 mm to about 39 mm, about 27 mm to about 40 mm, about 28 mm to about 29 mm, about 28 mm to about 30 mm, about 28 mm to about 31 mm, about 28 mm to about 32 mm, about 28 mm to about 33 mm, about 28 mm to about 34 mm, about 28 mm to about 35 mm, about 28 mm to about 36 mm, about 28 mm to about 37 mm, about 28 mm to about 38 mm, about 28 mm to about 39 mm, about 28 mm to about 40 mm, about 29 mm to about 30 mm, about 29 mm to about 31 mm, about 29 mm to about 32 mm, about 29 mm to about 33 mm, about 29 mm to about 34 mm, about 29 mm to about 35 mm, about 29 mm to about 36 mm, about 29 mm to about 37 mm, about 29 mm to about 38 mm, about 29 mm to about 39 mm, about 29 mm to about 40 mm, about 30 mm to about 31 mm, about 30 mm to about 32 mm, about 30 mm to about 33 mm, about 30 mm to about 34 mm, about 30 mm to about 35 mm, about 30 mm to about 36 mm, about 30 mm to about 37 mm, about 30 mm to about 38 mm, about 30 mm to about 39 mm, about 30 mm to about 40 mm, about 31 mm to about 32 mm, about 31 mm to about 33 mm, about 31 mm to about 34 mm, about 31 mm to about 35 mm, about 31 mm to about 36 mm, about 31 mm to about 37 mm, about 31 mm to about 38 mm, about 31 mm to about 39 mm, about 31 mm to about 40 mm, about 32 mm to about 33 mm, about 32 mm to about 34 mm, about 32 mm to about 35 mm, about 32 mm to about 36 mm, about 32 mm to about 37 mm, about 32 mm to about 38 mm, about 32 mm to about 39 mm, about 32 mm to about 40 mm, about 33 mm to about 34 mm, about 33 mm to about 35 mm, about 33 mm to about 36 mm, about 33 mm to about 37 mm, about 33 mm to about 38 mm, about 33 mm to about 39 mm, about 33 mm to about 40 mm, about 34 mm to about 35 mm, about 34 mm to about 36 mm, about 34 mm to about 37 mm, about 34 mm to about 38 mm, about 34 mm to about 39 mm, about 34 mm to about 40 mm, about 35 mm to about 36 mm, about 35 mm to about 37 mm, about 35 mm to about 38 mm, about 35 mm to about 39 mm, about 35 mm to about 40 mm, about 36 mm to about 37 mm, about 36 mm to about 38 mm, about 36 mm to about 39 mm, about 36 mm to about 40 mm, about 37 mm to about 38 mm, about 37 mm to about 39 mm, about 37 mm to about 40 mm, about 38 mm to about 39 mm, about 38 mm to about 40 mm, or about 39 mm to about 40 mm.

Once more, in the exemplary embodiment of the overtube device 20, the primary lumen 60 is formed contiguous with or in fluid communication between the proximal and distal openings 32, 34 of the body 30, such that the length of the primary lumen 60 is substantially the same as the length of the body 30. In aspects of this embodiment, the length of the primary lumen 60 is, e.g., about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, about 110 mm, about 120 mm, about 130 mm, about 140 mm, about 150 mm, about 160 mm, about 170 mm, about 180 mm, about 190 mm, or about 200 mm. In other aspects of this embodiment, in an overtube device 20 disclosed herein the length of the primary lumen 60 is, e.g., at least 15 mm, at least 20 mm, at least 25 mm, at least 30 mm, at least 35 mm, at least 40 mm, at least 45 mm, at least 50 mm, at least 55 mm, at least 60 mm, at least 65 mm, at least 70 mm, at least 75 mm, at least 80 mm, at least 85 mm, at least 90 mm, at least 95 mm, at least 100 mm, at least 110 mm, at least 120 mm, at least 130 mm, at least 140 mm, at least 150 mm, at least 160 mm, at least 170 mm, at least 180 mm, at least 190 mm, or at least 200 mm. In other aspects of this embodiment, in an overtube device 20 disclosed herein the length of the primary lumen 60 is, e.g., at most 15 mm, at most 20 mm, at most 25 mm, at most 30 mm, at most 35 mm, at most 40 mm, at most 45 mm, at most 50 mm, at most 55 mm, at most 60 mm, at most 65 mm, at most 70 mm, at most 75 mm, at most 80 mm, at most 85 mm, at most 90 mm, at most 95 mm, at most 100 mm, at most 110 mm, at most 120 mm, at most 130 mm, at most 140 mm, at most 150 mm, at most 160 mm, at most 170 mm, at most 180 mm, at most 190 mm, or at most 200 mm.

In other aspects of this embodiment, in an overtube device 20 disclosed herein the length of the primary lumen 60 is, e.g., about 15 mm to about 20 mm, about 15 mm to about 25 mm, about 15 mm to about 30 mm, about 15 mm to about 35 mm, about 15 mm to about 40 mm, about 15 mm to about 45 mm, about 15 mm to about 50 mm, about 15 mm to about 55 mm, about 15 mm to about 60 mm, about 15 mm to about 65 mm, about 15 mm to about 70 mm, about 15 mm to about 75 mm, about 15 mm to about 80 mm, about 15 mm to about 85 mm, about 15 mm to about 90 mm, about 15 mm to about 95 mm, about 15 mm to about 100 mm, about 15 mm to about 110 mm, about 15 mm to about 120 mm, about 15 mm to about 130 mm, about 15 mm to about 140 mm, about 15 mm to about 150 mm, about 15 mm to about 160 mm, about 15 mm to about 170 mm, about 15 mm to about 180 mm, about 15 mm to about 190 mm, about 15 mm to about 200 mm, about 20 mm to about 25 mm, about 20 mm to about 30 mm, about 20 mm to about 35 mm, about 20 mm to about 40 mm, about 20 mm to about 45 mm, about 20 mm to about 50 mm, about 20 mm to about 55 mm, about 20 mm to about 60 mm, about 20 mm to about 65 mm, about 20 mm to about 70 mm, about 20 mm to about 75 mm, about 20 mm to about 80 mm, about 20 mm to about 85 mm, about 20 mm to about 90 mm, about 20 mm to about 95 mm, about 20 mm to about 100 mm, about 20 mm to about 110 mm, about 20 mm to about 120 mm, about 20 mm to about 130 mm, about 20 mm to about 140 mm, about 20 mm to about 150 mm, about 20 mm to about 160 mm, about 20 mm to about 170 mm, about 20 mm to about 180 mm, about 20 mm to about 190 mm, about 20 mm to about 200 mm, about 25 mm to about 30 mm, about 25 mm to about 35 mm, about 25 mm to about 40 mm, about 25 mm to about 45 mm, about 25 mm to about 50 mm, about 25 mm to about 55 mm, about 25 mm to about 60 mm, about 25 mm to about 65 mm, about 25 mm to about 70 mm, about 25 mm to about 75 mm, about 25 mm to about 80 mm, about 25 mm to about 85 mm, about 25 mm to about 90 mm, about 25 mm to about 95 mm, about 25 mm to about 100 mm, about 25 mm to about 110 mm, about 25 mm to about 120 mm, about 25 mm to about 130 mm, about 25 mm to about 140 mm, about 25 mm to about 150 mm, about 25 mm to about 160 mm, about 25 mm to about 170 mm, about 25 mm to about 180 mm, about 25 mm to about 190 mm, about 25 mm to about 200 mm, about 30 mm to about 35 mm, about 30 mm to about 40 mm, about 30 mm to about 45 mm, about 30 mm to about 50 mm, about 30 mm to about 55 mm, about 30 mm to about 60 mm, about 30 mm to about 65 mm, about 30 mm to about 70 mm, about 30 mm to about 75 mm, about 30 mm to about 80 mm, about 30 mm to about 85 mm, about 30 mm to about 90 mm, about 30 mm to about 95 mm, about 30 mm to about 100 mm, about 30 mm to about 110 mm, about 30 mm to about 120 mm, about 30 mm to about 130 mm, about 30 mm to about 140 mm, about 30 mm to about 150 mm, about 30 mm to about 160 mm, about 30 mm to about 170 mm, about 30 mm to about 180 mm, about 30 mm to about 190 mm, about 30 mm to about 200 mm, about 35 mm to about 40 mm, about 35 mm to about 45 mm, about 35 mm to about 50 mm, about 35 mm to about 55 mm, about 35 mm to about 60 mm, about 35 mm to about 65 mm, about 35 mm to about 70 mm, about 35 mm to about 75 mm, about 35 mm to about 80 mm, about 35 mm to about 85 mm, about 35 mm to about 90 mm, about 35 mm to about 95 mm, about 35 mm to about 100 mm, about 35 mm to about 110 mm, about 35 mm to about 120 mm, about 35 mm to about 130 mm, about 35 mm to about 140 mm, about 35 mm to about 150 mm, about 35 mm to about 160 mm, about 35 mm to about 170 mm, about 35 mm to about 180 mm, about 35 mm to about 190 mm, about 35 mm to about 200 mm, about 40 mm to about 45 mm, about 40 mm to about 50 mm, about 40 mm to about 55 mm, about 40 mm to about 60 mm, about 40 mm to about 65 mm, about 40 mm to about 70 mm, about 40 mm to about 75 mm, about 40 mm to about 80 mm, about 40 mm to about 85 mm, about 40 mm to about 90 mm, about 40 mm to about 95 mm, about 40 mm to about 100 mm, about 40 mm to about 110 mm, about 40 mm to about 120 mm, about 40 mm to about 130 mm, about 40 mm to about 140 mm, about 40 mm to about 150 mm, about 40 mm to about 160 mm, about 40 mm to about 170 mm, about 40 mm to about 180 mm, about 40 mm to about 190 mm, about 40 mm to about 200 mm, about 45 mm to about 50 mm, about 45 mm to about 55 mm, about 45 mm to about 60 mm, about 45 mm to about 65 mm, about 45 mm to about 70 mm, about 45 mm to about 75 mm, about 45 mm to about 80 mm, about 45 mm to about 85 mm, about 45 mm to about 90 mm, about 45 mm to about 95 mm, about 45 mm to about 100 mm, about 45 mm to about 110 mm, about 45 mm to about 120 mm, about 45 mm to about 130 mm, about 45 mm to about 140 mm, about 45 mm to about 150 mm, about 45 mm to about 160 mm, about 45 mm to about 170 mm, about 45 mm to about 180 mm, about 45 mm to about 190 mm, about 45 mm to about 200 mm, about 50 mm to about 55 mm, about 50 mm to about 60 mm, about 50 mm to about 65 mm, about 50 mm to about 70 mm, about 50 mm to about 75 mm, about 50 mm to about 80 mm, about 50 mm to about 85 mm, about 50 mm to about 90 mm, about 50 mm to about 95 mm, about 50 mm to about 100 mm, about 50 mm to about 110 mm, about 50 mm to about 120 mm, about 50 mm to about 130 mm, about 50 mm to about 140 mm, about 50 mm to about 150 mm, about 50 mm to about 160 mm, about 50 mm to about 170 mm, about 50 mm to about 180 mm, about 50 mm to about 190 mm, about 50 mm to about 200 mm, about 55 mm to about 60 mm, about 55 mm to about 65 mm, about 55 mm to about 70 mm, about 55 mm to about 75 mm, about 55 mm to about 80 mm, about 55 mm to about 85 mm, about 55 mm to about 90 mm, about 55 mm to about 95 mm, about 55 mm to about 100 mm, about 55 mm to about 110 mm, about 55 mm to about 120 mm, about 55 mm to about 130 mm, about 55 mm to about 140 mm, about 55 mm to about 150 mm, about 55 mm to about 160 mm, about 55 mm to about 170 mm, about 55 mm to about 180 mm, about 55 mm to about 190 mm, about 55 mm to about 200 mm, about 60 mm to about 65 mm, about 60 mm to about 70 mm, about 60 mm to about 75 mm, about 60 mm to about 80 mm, about 60 mm to about 85 mm, about 60 mm to about 90 mm, about 60 mm to about 95 mm, about 60 mm to about 100 mm, about 60 mm to about 110 mm, about 60 mm to about 120 mm, about 60 mm to about 130 mm, about 60 mm to about 140 mm, about 60 mm to about 150 mm, about 60 mm to about 160 mm, about 60 mm to about 170 mm, about 60 mm to about 180 mm, about 60 mm to about 190 mm, about 60 mm to about 200 mm, about 65 mm to about 70 mm, about 65 mm to about 75 mm, about 65 mm to about 80 mm, about 65 mm to about 85 mm, about 65 mm to about 90 mm, about 65 mm to about 95 mm, about 65 mm to about 100 mm, about 65 mm to about 110 mm, about 65 mm to about 120 mm, about 65 mm to about 130 mm, about 65 mm to about 140 mm, about 65 mm to about 150 mm, about 65 mm to about 160 mm, about 65 mm to about 170 mm, about 65 mm to about 180 mm, about 65 mm to about 190 mm, about 65 mm to about 200 mm, about 70 mm to about 75 mm, about 70 mm to about 80 mm, about 70 mm to about 85 mm, about 70 mm to about 90 mm, about 70 mm to about 95 mm, about 70 mm to about 100 mm, about 70 mm to about 110 mm, about 70 mm to about 120 mm, about 70 mm to about 130 mm, about 70 mm to about 140 mm, about 70 mm to about 150 mm, about 70 mm to about 160 mm, about 70 mm to about 170 mm, about 70 mm to about 180 mm, about 70 mm to about 190 mm, about 70 mm to about 200 mm, about 75 mm to about 80 mm about 75 mm to about 85 mm, about 75 mm to about 90 mm, about 75 mm to about 95 mm, about 75 mm to about 100 mm, about 75 mm to about 110 mm, about 75 mm to about 120 mm, about 75 mm to about 130 mm, about 75 mm to about 140 mm, about 75 mm to about 150 mm, about 75 mm to about 160 mm, about 75 mm to about 170 mm, about 75 mm to about 180 mm, about 75 mm to about 190 mm, about 75 mm to about 200 mm, about 80 mm to about 85 mm, about 80 mm to about 90 mm, about 80 mm to about 95 mm, about 80 mm to about 100 mm, about 80 mm to about 110 mm, about 80 mm to about 120 mm, about 80 mm to about 130 mm, about 80 mm to about 140 mm, about 80 mm to about 150 mm, about 80 mm to about 160 mm, about 80 mm to about 170 mm, about 80 mm to about 180 mm, about 80 mm to about 190 mm, about 80 mm to about 200 mm, about 85 mm to about 90 mm, about 85 mm to about 95 mm, about 85 mm to about 100 mm, about 85 mm to about 110 mm, about 85 mm to about 120 mm, about 85 mm to about 130 mm, about 85 mm to about 140 mm, about 85 mm to about 150 mm, about 85 mm to about 160 mm, about 85 mm to about 170 mm, about 85 mm to about 180 mm, about 85 mm to about 190 mm, about 85 mm to about 200 mm, about 90 mm to about 95 mm, about 90 mm to about 100 mm, about 90 mm to about 110 mm, about 90 mm to about 120 mm, about 90 mm to about 130 mm, about 90 mm to about 140 mm, about 90 mm to about 150 mm, about 90 mm to about 160 mm, about 90 mm to about 170 mm, about 90 mm to about 180 mm, about 90 mm to about 190 mm, about 90 mm to about 200 mm, about 95 mm to about 100 mm, about 95 mm to about 110 mm, about 95 mm to about 120 mm, about 95 mm to about 130 mm, about 95 mm to about 140 mm, about 95 mm to about 150 mm, about 95 mm to about 160 mm, about 95 mm to about 170 mm, about 95 mm to about 180 mm, about 95 mm to about 190 mm, about 95 mm to about 200 mm, about 100 mm to about 110 mm, about 100 mm to about 120 mm, about 100 mm to about 130 mm, about 100 mm to about 140 mm, about 100 mm to about 150 mm, about 100 mm to about 160 mm, about 100 mm to about 170 mm, about 100 mm to about 180 mm, about 100 mm to about 190 mm, about 100 mm to about 200 mm, about 110 mm to about 120 mm, about 110 mm to about 130 mm, about 110 mm to about 140 mm, about 110 mm to about 150 mm, about 110 mm to about 160 mm, about 110 mm to about 170 mm, about 110 mm to about 180 mm, about 110 mm to about 190 mm, about 110 mm to about 200 mm, about 120 mm to about 130 mm, about 120 mm to about 140 mm, about 120 mm to about 150 mm, about 120 mm to about 160 mm, about 120 mm to about 170 mm, about 120 mm to about 180 mm, about 120 mm to about 190 mm, about 120 mm to about 200 mm, about 130 mm to about 140 mm, about 130 mm to about 150 mm, about 130 mm to about 160 mm, about 130 mm to about 170 mm, about 130 mm to about 180 mm, about 130 mm to about 190 mm, about 130 mm to about 200 mm, about 140 mm to about 150 mm, about 140 mm to about 160 mm, about 140 mm to about 170 mm, about 140 mm to about 180 mm, about 140 mm to about 190 mm, about 140 mm to about 200 mm, about 150 mm to about 160 mm, about 150 mm to about 170 mm, about 150 mm to about 180 mm, about 150 mm to about 190 mm, about 150 mm to about 200 mm, about 160 mm to about 170 mm, about 160 mm to about 180 mm, about 160 mm to about 190 mm, about 160 mm to about 200 mm, about 170 mm to about 180 mm, about 170 mm to about 190 mm, about 170 mm to about 200 mm, about 180 mm to about 190 mm, about 180 mm to about 200 mm, or about 190 mm to about 200 mm.

Regarding the secondary lumen 70 that intersects the primary lumen 60, once more, the secondary lumen 70 defines the suction port 50 in one exemplary embodiment and the suction port 50 plus an integral barb fitting 76 in another embodiment, such that the length of the primary lumen 60 is substantially the same as the length of the suction port 50 alone or in combination with the barb fitting 76. In aspects of this embodiment, the length of the secondary lumen 70 is, e.g., about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, about 110 mm, about 120 mm, about 130 mm, about 140 mm, about 150 mm, about 160 mm, about 170 mm, about 180 mm, about 190 mm, or about 200 mm. In other aspects of this embodiment, in an overtube device 20 disclosed herein the length of the primary lumen 60 is, e.g., at least 15 mm, at least 20 mm, at least 25 mm, at least 30 mm, at least 35 mm, at least 40 mm, at least 45 mm, at least 50 mm, at least 55 mm, at least 60 mm, at least 65 mm, at least 70 mm, at least 75 mm, at least 80 mm, at least 85 mm, at least 90 mm, at least 95 mm, at least 100 mm, at least 110 mm, at least 120 mm, at least 130 mm, at least 140 mm, at least 150 mm, at least 160 mm, at least 170 mm, at least 180 mm, at least 190 mm, or at least 200 mm. In other aspects of this embodiment, in an overtube device 20 disclosed herein the length of the primary lumen 60 is, e.g., at most 15 mm, at most 20 mm, at most 25 mm, at most 30 mm, at most 35 mm, at most 40 mm, at most 45 mm, at most 50 mm, at most 55 mm, at most 60 mm, at most 65 mm, at most 70 mm, at most 75 mm, at most 80 mm, at most 85 mm, at most 90 mm, at most 95 mm, at most 100 mm, at most 110 mm, at most 120 mm, at most 130 mm, at most 140 mm, at most 150 mm, at most 160 mm, at most 170 mm, at most 180 mm, at most 190 mm, or at most 200 mm.

In other aspects of this embodiment, in an overtube device 20 disclosed herein the length of the secondary lumen 70 is, e.g., about 15 mm to about 20 mm, about 15 mm to about 25 mm, about 15 mm to about 30 mm, about 15 mm to about 35 mm, about 15 mm to about 40 mm, about 15 mm to about 45 mm, about 15 mm to about 50 mm, about 15 mm to about 55 mm, about 15 mm to about 60 mm, about 15 mm to about 65 mm, about 15 mm to about 70 mm, about 15 mm to about 75 mm, about 15 mm to about 80 mm, about 15 mm to about 85 mm, about 15 mm to about 90 mm, about 15 mm to about 95 mm, about 15 mm to about 100 mm, about 15 mm to about 110 mm, about 15 mm to about 120 mm, about 15 mm to about 130 mm, about 15 mm to about 140 mm, about 15 mm to about 150 mm, about 15 mm to about 160 mm, about 15 mm to about 170 mm, about 15 mm to about 180 mm, about 15 mm to about 190 mm, about 15 mm to about 200 mm, about 20 mm to about 25 mm, about 20 mm to about 30 mm, about 20 mm to about 35 mm, about 20 mm to about 40 mm, about 20 mm to about 45 mm, about 20 mm to about 50 mm, about 20 mm to about 55 mm, about 20 mm to about 60 mm, about 20 mm to about 65 mm, about 20 mm to about 70 mm, about 20 mm to about 75 mm, about 20 mm to about 80 mm, about 20 mm to about 85 mm, about 20 mm to about 90 mm, about 20 mm to about 95 mm, about 20 mm to about 100 mm, about 20 mm to about 110 mm, about 20 mm to about 120 mm, about 20 mm to about 130 mm, about 20 mm to about 140 mm, about 20 mm to about 150 mm, about 20 mm to about 160 mm, about 20 mm to about 170 mm, about 20 mm to about 180 mm, about 20 mm to about 190 mm, about 20 mm to about 200 mm, about 25 mm to about 30 mm, about 25 mm to about 35 mm, about 25 mm to about 40 mm, about 25 mm to about 45 mm, about 25 mm to about 50 mm, about 25 mm to about 55 mm, about 25 mm to about 60 mm, about 25 mm to about 65 mm, about 25 mm to about 70 mm, about 25 mm to about 75 mm, about 25 mm to about 80 mm, about 25 mm to about 85 mm, about 25 mm to about 90 mm, about 25 mm to about 95 mm, about 25 mm to about 100 mm, about 25 mm to about 110 mm, about 25 mm to about 120 mm, about 25 mm to about 130 mm, about 25 mm to about 140 mm, about 25 mm to about 150 mm, about 25 mm to about 160 mm, about 25 mm to about 170 mm, about 25 mm to about 180 mm, about 25 mm to about 190 mm, about 25 mm to about 200 mm, about 30 mm to about 35 mm, about 30 mm to about 40 mm, about 30 mm to about 45 mm, about 30 mm to about 50 mm, about 30 mm to about 55 mm, about 30 mm to about 60 mm, about 30 mm to about 65 mm, about 30 mm to about 70 mm, about 30 mm to about 75 mm, about 30 mm to about 80 mm, about 30 mm to about 85 mm, about 30 mm to about 90 mm, about 30 mm to about 95 mm, about 30 mm to about 100 mm, about 30 mm to about 110 mm, about 30 mm to about 120 mm, about 30 mm to about 130 mm, about 30 mm to about 140 mm, about 30 mm to about 150 mm, about 30 mm to about 160 mm, about 30 mm to about 170 mm, about 30 mm to about 180 mm, about 30 mm to about 190 mm, about 30 mm to about 200 mm, about 35 mm to about 40 mm, about 35 mm to about 45 mm, about 35 mm to about 50 mm, about 35 mm to about 55 mm, about 35 mm to about 60 mm, about 35 mm to about 65 mm, about 35 mm to about 70 mm, about 35 mm to about 75 mm, about 35 mm to about 80 mm, about 35 mm to about 85 mm, about 35 mm to about 90 mm, about 35 mm to about 95 mm, about 35 mm to about 100 mm, about 35 mm to about 110 mm, about 35 mm to about 120 mm, about 35 mm to about 130 mm, about 35 mm to about 140 mm, about 35 mm to about 150 mm, about 35 mm to about 160 mm, about 35 mm to about 170 mm, about 35 mm to about 180 mm, about 35 mm to about 190 mm, about 35 mm to about 200 mm, about 40 mm to about 45 mm, about 40 mm to about 50 mm, about 40 mm to about 55 mm, about 40 mm to about 60 mm, about 40 mm to about 65 mm, about 40 mm to about 70 mm, about 40 mm to about 75 mm, about 40 mm to about 80 mm, about 40 mm to about 85 mm, about 40 mm to about 90 mm, about 40 mm to about 95 mm, about 40 mm to about 100 mm, about 40 mm to about 110 mm, about 40 mm to about 120 mm, about 40 mm to about 130 mm, about 40 mm to about 140 mm, about 40 mm to about 150 mm, about 40 mm to about 160 mm, about 40 mm to about 170 mm, about 40 mm to about 180 mm, about 40 mm to about 190 mm, about 40 mm to about 200 mm, about 45 mm to about 50 mm, about 45 mm to about 55 mm, about 45 mm to about 60 mm, about 45 mm to about 65 mm, about 45 mm to about 70 mm, about 45 mm to about 75 mm, about 45 mm to about 80 mm, about 45 mm to about 85 mm, about 45 mm to about 90 mm, about 45 mm to about 95 mm, about 45 mm to about 100 mm, about 45 mm to about 110 mm, about 45 mm to about 120 mm, about 45 mm to about 130 mm, about 45 mm to about 140 mm, about 45 mm to about 150 mm, about 45 mm to about 160 mm, about 45 mm to about 170 mm, about 45 mm to about 180 mm, about 45 mm to about 190 mm, about 45 mm to about 200 mm, about 50 mm to about 55 mm, about 50 mm to about 60 mm, about 50 mm to about 65 mm, about 50 mm to about 70 mm, about 50 mm to about 75 mm, about 50 mm to about 80 mm, about 50 mm to about 85 mm, about 50 mm to about 90 mm, about 50 mm to about 95 mm, about 50 mm to about 100 mm, about 50 mm to about 110 mm, about 50 mm to about 120 mm, about 50 mm to about 130 mm, about 50 mm to about 140 mm, about 50 mm to about 150 mm, about 50 mm to about 160 mm, about 50 mm to about 170 mm, about 50 mm to about 180 mm, about 50 mm to about 190 mm, about 50 mm to about 200 mm, about 55 mm to about 60 mm, about 55 mm to about 65 mm, about 55 mm to about 70 mm, about 55 mm to about 75 mm, about 55 mm to about 80 mm, about 55 mm to about 85 mm, about 55 mm to about 90 mm, about 55 mm to about 95 mm, about 55 mm to about 100 mm, about 55 mm to about 110 mm, about 55 mm to about 120 mm, about 55 mm to about 130 mm, about 55 mm to about 140 mm, about 55 mm to about 150 mm, about 55 mm to about 160 mm, about 55 mm to about 170 mm, about 55 mm to about 180 mm, about 55 mm to about 190 mm, about 55 mm to about 200 mm, about 60 mm to about 65 mm, about 60 mm to about 70 mm, about 60 mm to about 75 mm, about 60 mm to about 80 mm, about 60 mm to about 85 mm, about 60 mm to about 90 mm, about 60 mm to about 95 mm, about 60 mm to about 100 mm, about 60 mm to about 110 mm, about 60 mm to about 120 mm, about 60 mm to about 130 mm, about 60 mm to about 140 mm, about 60 mm to about 150 mm, about 60 mm to about 160 mm, about 60 mm to about 170 mm, about 60 mm to about 180 mm, about 60 mm to about 190 mm, about 60 mm to about 200 mm, about 65 mm to about 70 mm, about 65 mm to about 75 mm, about 65 mm to about 80 mm, about 65 mm to about 85 mm, about 65 mm to about 90 mm, about 65 mm to about 95 mm, about 65 mm to about 100 mm, about 65 mm to about 110 mm, about 65 mm to about 120 mm, about 65 mm to about 130 mm, about 65 mm to about 140 mm, about 65 mm to about 150 mm, about 65 mm to about 160 mm, about 65 mm to about 170 mm, about 65 mm to about 180 mm, about 65 mm to about 190 mm, about 65 mm to about 200 mm, about 70 mm to about 75 mm, about 70 mm to about 80 mm, about 70 mm to about 85 mm, about 70 mm to about 90 mm, about 70 mm to about 95 mm, about 70 mm to about 100 mm, about 70 mm to about 110 mm, about 70 mm to about 120 mm, about 70 mm to about 130 mm, about 70 mm to about 140 mm, about 70 mm to about 150 mm, about 70 mm to about 160 mm, about 70 mm to about 170 mm, about 70 mm to about 180 mm, about 70 mm to about 190 mm, about 70 mm to about 200 mm, about 75 mm to about 80 mm about 75 mm to about 85 mm, about 75 mm to about 90 mm, about 75 mm to about 95 mm, about 75 mm to about 100 mm, about 75 mm to about 110 mm, about 75 mm to about 120 mm, about 75 mm to about 130 mm, about 75 mm to about 140 mm, about 75 mm to about 150 mm, about 75 mm to about 160 mm, about 75 mm to about 170 mm, about 75 mm to about 180 mm, about 75 mm to about 190 mm, about 75 mm to about 200 mm, about 80 mm to about 85 mm, about 80 mm to about 90 mm, about 80 mm to about 95 mm, about 80 mm to about 100 mm, about 80 mm to about 110 mm, about 80 mm to about 120 mm, about 80 mm to about 130 mm, about 80 mm to about 140 mm, about 80 mm to about 150 mm, about 80 mm to about 160 mm, about 80 mm to about 170 mm, about 80 mm to about 180 mm, about 80 mm to about 190 mm, about 80 mm to about 200 mm, about 85 mm to about 90 mm, about 85 mm to about 95 mm, about 85 mm to about 100 mm, about 85 mm to about 110 mm, about 85 mm to about 120 mm, about 85 mm to about 130 mm, about 85 mm to about 140 mm, about 85 mm to about 150 mm, about 85 mm to about 160 mm, about 85 mm to about 170 mm, about 85 mm to about 180 mm, about 85 mm to about 190 mm, about 85 mm to about 200 mm, about 90 mm to about 95 mm, about 90 mm to about 100 mm, about 90 mm to about 110 mm, about 90 mm to about 120 mm, about 90 mm to about 130 mm, about 90 mm to about 140 mm, about 90 mm to about 150 mm, about 90 mm to about 160 mm, about 90 mm to about 170 mm, about 90 mm to about 180 mm, about 90 mm to about 190 mm, about 90 mm to about 200 mm, about 95 mm to about 100 mm, about 95 mm to about 110 mm, about 95 mm to about 120 mm, about 95 mm to about 130 mm, about 95 mm to about 140 mm, about 95 mm to about 150 mm, about 95 mm to about 160 mm, about 95 mm to about 170 mm, about 95 mm to about 180 mm, about 95 mm to about 190 mm, about 95 mm to about 200 mm, about 100 mm to about 110 mm, about 100 mm to about 120 mm, about 100 mm to about 130 mm, about 100 mm to about 140 mm, about 100 mm to about 150 mm, about 100 mm to about 160 mm, about 100 mm to about 170 mm, about 100 mm to about 180 mm, about 100 mm to about 190 mm, about 100 mm to about 200 mm, about 110 mm to about 120 mm, about 110 mm to about 130 mm, about 110 mm to about 140 mm, about 110 mm to about 150 mm, about 110 mm to about 160 mm, about 110 mm to about 170 mm, about 110 mm to about 180 mm, about 110 mm to about 190 mm, about 110 mm to about 200 mm, about 120 mm to about 130 mm, about 120 mm to about 140 mm, about 120 mm to about 150 mm, about 120 mm to about 160 mm, about 120 mm to about 170 mm, about 120 mm to about 180 mm, about 120 mm to about 190 mm, about 120 mm to about 200 mm, about 130 mm to about 140 mm, about 130 mm to about 150 mm, about 130 mm to about 160 mm, about 130 mm to about 170 mm, about 130 mm to about 180 mm, about 130 mm to about 190 mm, about 130 mm to about 200 mm, about 140 mm to about 150 mm, about 140 mm to about 160 mm, about 140 mm to about 170 mm, about 140 mm to about 180 mm, about 140 mm to about 190 mm, about 140 mm to about 200 mm, about 150 mm to about 160 mm, about 150 mm to about 170 mm, about 150 mm to about 180 mm, about 150 mm to about 190 mm, about 150 mm to about 200 mm, about 160 mm to about 170 mm, about 160 mm to about 180 mm, about 160 mm to about 190 mm, about 160 mm to about 200 mm, about 170 mm to about 180 mm, about 170 mm to about 190 mm, about 170 mm to about 200 mm, about 180 mm to about 190 mm, about 180 mm to about 200 mm, or about 190 mm to about 200 mm.

Finally, in other aspects of this embodiment, in an overtube device 20 wherein the effective wall thickness of the body wall 40 of the body 30 is defined by the distance at any location between the outer and inner diameters or widths, the wall thickness is, e.g., about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, or about 5.0 mm. In still further aspects of this embodiment, the wall thickness of the body wall 40 is, e.g., at least 0.1 mm, at least 0.2 mm, at least 0.3 mm, at least 0.4 mm, at least 0.5 mm, at least 0.6 mm, at least 0.7 mm, at least 0.8 mm, at least 0.9 mm, at least 1.0 mm, at least 1.1 mm, at least 1.2 mm, at least 1.3 mm, at least 1.4 mm, at least 1.5 mm, at least 1.6 mm, at least 1.7 mm, at least 1.8 mm, at least 1.9 mm, at least 2.0 mm, at least 2.1 mm, at least 2.2 mm, at least 2.3 mm, at least 2.4 mm, at least 2.5 mm, at least 2.6 mm, at least 2.7 mm, at least 2.8 mm, at least 2.9 mm, at least 3.0 mm, at least 3.2 mm, at least 3.4 mm, at least 3.6 mm, at least 3.8 mm, at least 4.0 mm, at least 4.2 mm, at least 4.4 mm, at least 4.6 mm, at least 4.8 mm, or at least 5.0 mm. In still further aspects of this embodiment, the wall thickness of the body wall 40 is, e.g., at most 0.1 mm, at most 0.2 mm, at most 0.3 mm, at most 0.4 mm, at most 0.5 mm, at most 0.6 mm, at most 0.7 mm, at most 0.8 mm, at most 0.9 mm, at most 1.0 mm, at most 1.1 mm, at most 1.2 mm, at most 1.3 mm, at most 1.4 mm, at most 1.5 mm, at most 1.6 mm, at most 1.7 mm, at most 1.8 mm, at most 1.9 mm, at most 2.0 mm, at most 2.1 mm, at most 2.2 mm, at most 2.3 mm, at most 2.4 mm, at most 2.5 mm, at most 2.6 mm, at most 2.7 mm, at most 2.8 mm, at most 2.9 mm, at most 3.0 mm, at most 3.2 mm, at most 3.4 mm, at most 3.6 mm, at most 3.8 mm, at most 4.0 mm, at most 4.2 mm, at most 4.4 mm, at most 4.6 mm, at most 4.8 mm, or at most 5.0 mm.

In other aspects of this embodiment, in an overtube device 20 disclosed herein the wall thickness of the body wall 40 is, e.g., about 0.1 mm to about 0.2 mm, about 0.1 mm to about 0.3 mm, about 0.1 mm to about 0.4 mm, about 0.1 mm to about 0.5 mm, about 0.1 mm to about 0.6 mm, about 0.1 mm to about 0.7 mm, about 0.1 mm to about 0.8 mm, about 0.1 mm to about 0.9 mm, about 0.1 mm to about 1.0 mm, about 0.1 mm to about 1.1 mm, about 0.1 mm to about 1.2 mm, about 0.1 mm to about 1.3 mm, about 0.1 mm to about 1.4 mm, about 0.1 mm to about 1.5 mm, about 0.1 mm to about 1.6 mm, about 0.1 mm to about 1.7 mm, about 0.1 mm to about 1.8 mm, about 0.1 mm to about 1.9 mm, about 0.1 mm to about 2.0 mm, about 0.1 mm to about 2.1 mm, about 0.1 mm to about 2.2 mm, about 0.1 mm to about 2.3 mm, about 0.1 mm to about 2.4 mm, about 0.1 mm to about 2.5 mm, about 0.1 mm to about 2.6 mm, about 0.1 mm to about 2.7 mm, about 0.1 mm to about 2.8 mm, about 0.1 mm to about 2.9 mm, about 0.1 mm to about 3.0 mm, about 0.1 mm to about 3.2 mm, about 0.1 mm to about 3.4 mm, about 0.1 mm to about 3.6 mm, about 0.1 mm to about 3.8 mm, about 0.1 mm to about 4.0 mm, about 0.1 mm to about 4.2 mm, about 0.1 mm to about 4.4 mm, about 0.1 mm to about 4.6 mm, about 0.1 mm to about 4.8 mm, about 0.1 mm to about 5.0 mm, about 0.2 mm to about 0.3 mm, about 0.2 mm to about 0.4 mm, about 0.2 mm to about 0.5 mm, about 0.2 mm to about 0.6 mm, about 0.2 mm to about 0.7 mm, about 0.2 mm to about 0.8 mm, about 0.2 mm to about 0.9 mm, about 0.2 mm to about 1.0 mm, about 0.2 mm to about 1.1 mm, about 0.2 mm to about 1.2 mm, about 0.2 mm to about 1.3 mm, about 0.2 mm to about 1.4 mm, about 0.2 mm to about 1.5 mm, about 0.2 mm to about 1.6 mm, about 0.2 mm to about 1.7 mm, about 0.2 mm to about 1.8 mm, about 0.2 mm to about 1.9 mm, about 0.2 mm to about 2.0 mm, about 0.2 mm to about 2.1 mm, about 0.2 mm to about 2.2 mm, about 0.2 mm to about 2.3 mm, about 0.2 mm to about 2.4 mm, about 0.2 mm to about 2.5 mm, about 0.2 mm to about 2.6 mm, about 0.2 mm to about 2.7 mm, about 0.2 mm to about 2.8 mm, about 0.2 mm to about 2.9 mm, about 0.2 mm to about 3.0 mm, about 0.2 mm to about 3.2 mm, about 0.2 mm to about 3.4 mm, about 0.2 mm to about 3.6 mm, about 0.2 mm to about 3.8 mm, about 0.2 mm to about 4.0 mm, about 0.2 mm to about 4.2 mm, about 0.2 mm to about 4.4 mm, about 0.2 mm to about 4.6 mm, about 0.2 mm to about 4.8 mm, about 0.2 mm to about 5.0 mm, about 0.3 mm to about 0.4 mm, about 0.3 mm to about 0.5 mm, about 0.3 mm to about 0.6 mm, about 0.3 mm to about 0.7 mm, about 0.3 mm to about 0.8 mm, about 0.3 mm to about 0.9 mm, about 0.3 mm to about 1.0 mm, about 0.3 mm to about 1.1 mm, about 0.3 mm to about 1.2 mm, about 0.3 mm to about 1.3 mm, about 0.3 mm to about 1.4 mm, about 0.3 mm to about 1.5 mm, about 0.3 mm to about 1.6 mm, about 0.3 mm to about 1.7 mm, about 0.3 mm to about 1.8 mm, about 0.3 mm to about 1.9 mm, about 0.3 mm to about 2.0 mm, about 0.3 mm to about 2.1 mm, about 0.3 mm to about 2.2 mm, about 0.3 mm to about 2.3 mm, about 0.3 mm to about 2.4 mm, about 0.3 mm to about 2.5 mm, about 0.3 mm to about 2.6 mm, about 0.3 mm to about 2.7 mm, about 0.3 mm to about 2.8 mm, about 0.3 mm to about 2.9 mm, about 0.3 mm to about 3.0 mm, about 0.3 mm to about 3.2 mm, about 0.3 mm to about 3.4 mm, about 0.3 mm to about 3.6 mm, about 0.3 mm to about 3.8 mm, about 0.3 mm to about 4.0 mm, about 0.3 mm to about 4.2 mm, about 0.3 mm to about 4.4 mm, about 0.3 mm to about 4.6 mm, about 0.3 mm to about 4.8 mm, about 0.3 mm to about 5.0 mm, about 0.4 mm to about 0.5 mm, about 0.4 mm to about 0.6 mm, about 0.4 mm to about 0.7 mm, about 0.4 mm to about 0.8 mm, about 0.4 mm to about 0.9 mm, about 0.4 mm to about 1.0 mm, about 0.4 mm to about 1.1 mm, about 0.4 mm to about 1.2 mm, about 0.4 mm to about 1.3 mm, about 0.4 mm to about 1.4 mm, about 0.4 mm to about 1.5 mm, about 0.4 mm to about 1.6 mm, about 0.4 mm to about 1.7 mm, about 0.4 mm to about 1.8 mm, about 0.4 mm to about 1.9 mm, about 0.4 mm to about 2.0 mm, about 0.4 mm to about 2.1 mm, about 0.4 mm to about 2.2 mm, about 0.4 mm to about 2.3 mm, about 0.4 mm to about 2.4 mm, about 0.4 mm to about 2.5 mm, about 0.4 mm to about 2.6 mm, about 0.4 mm to about 2.7 mm, about 0.4 mm to about 2.8 mm, about 0.4 mm to about 2.9 mm, about 0.4 mm to about 3.0 mm, about 0.4 mm to about 3.2 mm, about 0.4 mm to about 3.4 mm, about 0.4 mm to about 3.6 mm, about 0.4 mm to about 3.8 mm, about 0.4 mm to about 4.0 mm, about 0.4 mm to about 4.2 mm, about 0.4 mm to about 4.4 mm, about 0.4 mm to about 4.6 mm, about 0.4 mm to about 4.8 mm, about 0.4 mm to about 5.0 mm, about 0.5 mm to about 0.6 mm, about 0.5 mm to about 0.7 mm, about 0.5 mm to about 0.8 mm, about 0.5 mm to about 0.9 mm, about 0.5 mm to about 1.0 mm, about 0.5 mm to about 1.1 mm, about 0.5 mm to about 1.2 mm, about 0.5 mm to about 1.3 mm, about 0.5 mm to about 1.4 mm, about 0.5 mm to about 1.5 mm, about 0.5 mm to about 1.6 mm, about 0.5 mm to about 1.7 mm, about 0.5 mm to about 1.8 mm, about 0.5 mm to about 1.9 mm, about 0.5 mm to about 2.0 mm, about 0.5 mm to about 2.1 mm, about 0.5 mm to about 2.2 mm, about 0.5 mm to about 2.3 mm, about 0.5 mm to about 2.4 mm, about 0.5 mm to about 2.5 mm, about 0.5 mm to about 2.6 mm, about 0.5 mm to about 2.7 mm, about 0.5 mm to about 2.8 mm, about 0.5 mm to about 2.9 mm, about 0.5 mm to about 3.0 mm, about 0.5 mm to about 3.2 mm, about 0.5 mm to about 3.4 mm, about 0.5 mm to about 3.6 mm, about 0.5 mm to about 3.8 mm, about 0.5 mm to about 4.0 mm, about 0.5 mm to about 4.2 mm, about 0.5 mm to about 4.4 mm, about 0.5 mm to about 4.6 mm, about 0.5 mm to about 4.8 mm, about 0.5 mm to about 5.0 mm, about 0.6 mm to about 0.7 mm, about 0.6 mm to about 0.8 mm, about 0.6 mm to about 0.9 mm, about 0.6 mm to about 1.0 mm, about 0.6 mm to about 1.1 mm, about 0.6 mm to about 1.2 mm, about 0.6 mm to about 1.3 mm, about 0.6 mm to about 1.4 mm, about 0.6 mm to about 1.5 mm, about 0.6 mm to about 1.6 mm, about 0.6 mm to about 1.7 mm, about 0.6 mm to about 1.8 mm, about 0.6 mm to about 1.9 mm, about 0.6 mm to about 2.0 mm, about 0.6 mm to about 2.1 mm, about 0.6 mm to about 2.2 mm, about 0.6 mm to about 2.3 mm, about 0.6 mm to about 2.4 mm, about 0.6 mm to about 2.5 mm, about 0.6 mm to about 2.6 mm, about 0.6 mm to about 2.7 mm, about 0.6 mm to about 2.8 mm, about 0.6 mm to about 2.9 mm, about 0.6 mm to about 3.0 mm, about 0.6 mm to about 3.2 mm, about 0.6 mm to about 3.4 mm, about 0.6 mm to about 3.6 mm, about 0.6 mm to about 3.8 mm, about 0.6 mm to about 4.0 mm, about 0.6 mm to about 4.2 mm, about 0.6 mm to about 4.4 mm, about 0.6 mm to about 4.6 mm, about 0.6 mm to about 4.8 mm, about 0.6 mm to about 5.0 mm, about 0.7 mm to about 0.8 mm, about 0.7 mm to about 0.9 mm, about 0.7 mm to about 1.0 mm, about 0.7 mm to about 1.1 mm, about 0.7 mm to about 1.2 mm, about 0.7 mm to about 1.3 mm, about 0.7 mm to about 1.4 mm, about 0.7 mm to about 1.5 mm, about 0.7 mm to about 1.6 mm, about 0.7 mm to about 1.7 mm, about 0.7 mm to about 1.8 mm, about 0.7 mm to about 1.9 mm, about 0.7 mm to about 2.0 mm, about 0.7 mm to about 2.1 mm, about 0.7 mm to about 2.2 mm, about 0.7 mm to about 2.3 mm, about 0.7 mm to about 2.4 mm, about 0.7 mm to about 2.5 mm, about 0.7 mm to about 2.6 mm, about 0.7 mm to about 2.7 mm, about 0.7 mm to about 2.8 mm, about 0.7 mm to about 2.9 mm, about 0.7 mm to about 3.0 mm, about 0.7 mm to about 3.2 mm, about 0.7 mm to about 3.4 mm, about 0.7 mm to about 3.6 mm, about 0.7 mm to about 3.8 mm, about 0.7 mm to about 4.0 mm, about 0.7 mm to about 4.2 mm, about 0.7 mm to about 4.4 mm, about 0.7 mm to about 4.6 mm, about 0.7 mm to about 4.8 mm, about 0.7 mm to about 5.0 mm, about 0.8 mm to about 0.9 mm, about 0.8 mm to about 1.0 mm, about 0.8 mm to about 1.1 mm, about 0.8 mm to about 1.2 mm, about 0.8 mm to about 1.3 mm, about 0.8 mm to about 1.4 mm, about 0.8 mm to about 1.5 mm, about 0.8 mm to about 1.6 mm, about 0.8 mm to about 1.7 mm, about 0.8 mm to about 1.8 mm, about 0.8 mm to about 1.9 mm, about 0.8 mm to about 2.0 mm, about 0.8 mm to about 2.1 mm, about 0.8 mm to about 2.2 mm, about 0.8 mm to about 2.3 mm, about 0.8 mm to about 2.4 mm, about 0.8 mm to about 2.5 mm, about 0.8 mm to about 2.6 mm, about 0.8 mm to about 2.7 mm, about 0.8 mm to about 2.8 mm, about 0.8 mm to about 2.9 mm, about 0.8 mm to about 3.0 mm, about 0.8 mm to about 3.2 mm, about 0.8 mm to about 3.4 mm, about 0.8 mm to about 3.6 mm, about 0.8 mm to about 3.8 mm, about 0.8 mm to about 4.0 mm, about 0.8 mm to about 4.2 mm, about 0.8 mm to about 4.4 mm, about 0.8 mm to about 4.6 mm, about 0.8 mm to about 4.8 mm, about 0.8 mm to about 5.0 mm, about 0.9 mm to about 1.0 mm, about 0.9 mm to about 1.1 mm, about 0.9 mm to about 1.2 mm, about 0.9 mm to about 1.3 mm, about 0.9 mm to about 1.4 mm, about 0.9 mm to about 1.5 mm, about 0.9 mm to about 1.6 mm, about 0.9 mm to about 1.7 mm, about 0.9 mm to about 1.8 mm, about 0.9 mm to about 1.9 mm, about 0.9 mm to about 2.0 mm, about 0.9 mm to about 2.1 mm, about 0.9 mm to about 2.2 mm, about 0.9 mm to about 2.3 mm, about 0.9 mm to about 2.4 mm, about 0.9 mm to about 2.5 mm, about 0.9 mm to about 2.6 mm, about 0.9 mm to about 2.7 mm, about 0.9 mm to about 2.8 mm, about 0.9 mm to about 2.9 mm, about 0.9 mm to about 3.0 mm, about 0.9 mm to about 3.2 mm, about 0.9 mm to about 3.4 mm, about 0.9 mm to about 3.6 mm, about 0.9 mm to about 3.8 mm, about 0.9 mm to about 4.0 mm, about 0.9 mm to about 4.2 mm, about 0.9 mm to about 4.4 mm, about 0.9 mm to about 4.6 mm, about 0.9 mm to about 4.8 mm, about 0.9 mm to about 5.0 mm, about 1.0 mm to about 1.1 mm, about 1.0 mm to about 1.2 mm, about 1.0 mm to about 1.3 mm, about 1.0 mm to about 1.4 mm, about 1.0 mm to about 1.5 mm, about 1.0 mm to about 1.6 mm, about 1.0 mm to about 1.7 mm, about 1.0 mm to about 1.8 mm, about 1.0 mm to about 1.9 mm, about 1.0 mm to about 2.0 mm, about 1.0 mm to about 2.1 mm, about 1.0 mm to about 2.2 mm, about 1.0 mm to about 2.3 mm, about 1.0 mm to about 2.4 mm, about 1.0 mm to about 2.5 mm, about 1.0 mm to about 2.6 mm, about 1.0 mm to about 2.7 mm, about 1.0 mm to about 2.8 mm, about 1.0 mm to about 2.9 mm, about 1.0 mm to about 3.0 mm, about 1.0 mm to about 3.2 mm, about 1.0 mm to about 3.4 mm, about 1.0 mm to about 3.6 mm, about 1.0 mm to about 3.8 mm, about 1.0 mm to about 4.0 mm, about 1.0 mm to about 4.2 mm, about 1.0 mm to about 4.4 mm, about 1.0 mm to about 4.6 mm, about 1.0 mm to about 4.8 mm, about 1.0 mm to about 5.0 mm, about 1.1 mm to about 1.2 mm, about 1.1 mm to about 1.3 mm, about 1.1 mm to about 1.4 mm, about 1.1 mm to about 1.5 mm, about 1.1 mm to about 1.6 mm, about 1.1 mm to about 1.7 mm, about 1.1 mm to about 1.8 mm, about 1.1 mm to about 1.9 mm, about 1.1 mm to about 2.0 mm, about 1.1 mm to about 2.1 mm, about 1.1 mm to about 2.2 mm, about 1.1 mm to about 2.3 mm, about 1.1 mm to about 2.4 mm, about 1.1 mm to about 2.5 mm, about 1.1 mm to about 2.6 mm, about 1.1 mm to about 2.7 mm, about 1.1 mm to about 2.8 mm, about 1.1 mm to about 2.9 mm, about 1.1 mm to about 3.0 mm, about 1.1 mm to about 3.2 mm, about 1.1 mm to about 3.4 mm, about 1.1 mm to about 3.6 mm, about 1.1 mm to about 3.8 mm, about 1.1 mm to about 4.0 mm, about 1.1 mm to about 4.2 mm, about 1.1 mm to about 4.4 mm, about 1.1 mm to about 4.6 mm, about 1.1 mm to about 4.8 mm, about 1.1 mm to about 5.0 mm, about 1.2 mm to about 1.3 mm, about 1.2 mm to about 1.4 mm, about 1.2 mm to about 1.5 mm, about 1.2 mm to about 1.6 mm, about 1.2 mm to about 1.7 mm, about 1.2 mm to about 1.8 mm, about 1.2 mm to about 1.9 mm, about 1.2 mm to about 2.0 mm, about 1.2 mm to about 2.1 mm, about 1.2 mm to about 2.2 mm, about 1.2 mm to about 2.3 mm, about 1.2 mm to about 2.4 mm, about 1.2 mm to about 2.5 mm, about 1.2 mm to about 2.6 mm, about 1.2 mm to about 2.7 mm, about 1.2 mm to about 2.8 mm, about 1.2 mm to about 2.9 mm, about 1.2 mm to about 3.0 mm, about 1.2 mm to about 3.2 mm, about 1.2 mm to about 3.4 mm, about 1.2 mm to about 3.6 mm, about 1.2 mm to about 3.8 mm, about 1.2 mm to about 4.0 mm, about 1.2 mm to about 4.2 mm, about 1.2 mm to about 4.4 mm, about 1.2 mm to about 4.6 mm, about 1.2 mm to about 4.8 mm, about 1.2 mm to about 5.0 mm, about 1.3 mm to about 1.4 mm, about 1.3 mm to about 1.5 mm, about 1.3 mm to about 1.6 mm, about 1.3 mm to about 1.7 mm, about 1.3 mm to about 1.8 mm, about 1.3 mm to about 1.9 mm, about 1.3 mm to about 2.0 mm, about 1.3 mm to about 2.1 mm, about 1.3 mm to about 2.2 mm, about 1.3 mm to about 2.3 mm, about 1.3 mm to about 2.4 mm, about 1.3 mm to about 2.5 mm, about 1.3 mm to about 2.6 mm, about 1.3 mm to about 2.7 mm, about 1.3 mm to about 2.8 mm, about 1.3 mm to about 2.9 mm, about 1.3 mm to about 3.0 mm, about 1.3 mm to about 3.2 mm, about 1.3 mm to about 3.4 mm, about 1.3 mm to about 3.6 mm, about 1.3 mm to about 3.8 mm, about 1.3 mm to about 4.0 mm, about 1.3 mm to about 4.2 mm, about 1.3 mm to about 4.4 mm, about 1.3 mm to about 4.6 mm, about 1.3 mm to about 4.8 mm, about 1.3 mm to about 5.0 mm, about 1.4 mm to about 1.5 mm, about 1.4 mm to about 1.6 mm, about 1.4 mm to about 1.7 mm, about 1.4 mm to about 1.8 mm, about 1.4 mm to about 1.9 mm, about 1.4 mm to about 2.0 mm, about 1.4 mm to about 2.1 mm, about 1.4 mm to about 2.2 mm, about 1.4 mm to about 2.3 mm, about 1.4 mm to about 2.4 mm, about 1.4 mm to about 2.5 mm, about 1.4 mm to about 2.6 mm, about 1.4 mm to about 2.7 mm, about 1.4 mm to about 2.8 mm, about 1.4 mm to about 2.9 mm, about 1.4 mm to about 3.0 mm, about 1.4 mm to about 3.2 mm, about 1.4 mm to about 3.4 mm, about 1.4 mm to about 3.6 mm, about 1.4 mm to about 3.8 mm, about 1.4 mm to about 4.0 mm, about 1.4 mm to about 4.2 mm, about 1.4 mm to about 4.4 mm, about 1.4 mm to about 4.6 mm, about 1.4 mm to about 4.8 mm, about 1.4 mm to about 5.0 mm, about 1.5 mm to about 1.6 mm, about 1.5 mm to about 1.7 mm, about 1.5 mm to about 1.8 mm, about 1.5 mm to about 1.9 mm, about 1.5 mm to about 2.0 mm, about 1.5 mm to about 2.1 mm, about 1.5 mm to about 2.2 mm, about 1.5 mm to about 2.3 mm, about 1.5 mm to about 2.4 mm, about 1.5 mm to about 2.5 mm, about 1.5 mm to about 2.6 mm, about 1.5 mm to about 2.7 mm, about 1.5 mm to about 2.8 mm, about 1.5 mm to about 2.9 mm, about 1.5 mm to about 3.0 mm, about 1.5 mm to about 3.2 mm, about 1.5 mm to about 3.4 mm, about 1.5 mm to about 3.6 mm, about 1.5 mm to about 3.8 mm, about 1.5 mm to about 4.0 mm, about 1.5 mm to about 4.2 mm, about 1.5 mm to about 4.4 mm, about 1.5 mm to about 4.6 mm, about 1.5 mm to about 4.8 mm, about 1.5 mm to about 5.0 mm, about 1.6 mm to about 1.7 mm, about 1.6 mm to about 1.8 mm, about 1.6 mm to about 1.9 mm, about 1.6 mm to about 2.0 mm, about 1.6 mm to about 2.1 mm, about 1.6 mm to about 2.2 mm, about 1.6 mm to about 2.3 mm, about 1.6 mm to about 2.4 mm, about 1.6 mm to about 2.5 mm, about 1.6 mm to about 2.6 mm, about 1.6 mm to about 2.7 mm, about 1.6 mm to about 2.8 mm, about 1.6 mm to about 2.9 mm, about 1.6 mm to about 3.0 mm, about 1.6 mm to about 3.2 mm, about 1.6 mm to about 3.4 mm, about 1.6 mm to about 3.6 mm, about 1.6 mm to about 3.8 mm, about 1.6 mm to about 4.0 mm, about 1.6 mm to about 4.2 mm, about 1.6 mm to about 4.4 mm, about 1.6 mm to about 4.6 mm, about 1.6 mm to about 4.8 mm, about 1.6 mm to about 5.0 mm, about 1.7 mm to about 1.8 mm, about 1.7 mm to about 1.9 mm, about 1.7 mm to about 2.0 mm, about 1.7 mm to about 2.1 mm, about 1.7 mm to about 2.2 mm, about 1.7 mm to about 2.3 mm, about 1.7 mm to about 2.4 mm, about 1.7 mm to about 2.5 mm, about 1.7 mm to about 2.6 mm, about 1.7 mm to about 2.7 mm, about 1.7 mm to about 2.8 mm, about 1.7 mm to about 2.9 mm, about 1.7 mm to about 3.0 mm, about 1.7 mm to about 3.2 mm, about 1.7 mm to about 3.4 mm, about 1.7 mm to about 3.6 mm, about 1.7 mm to about 3.8 mm, about 1.7 mm to about 4.0 mm, about 1.7 mm to about 4.2 mm, about 1.7 mm to about 4.4 mm, about 1.7 mm to about 4.6 mm, about 1.7 mm to about 4.8 mm, about 1.7 mm to about 5.0 mm, about 1.8 mm to about 1.9 mm, about 1.8 mm to about 2.0 mm, about 1.8 mm to about 2.1 mm, about 1.8 mm to about 2.2 mm, about 1.8 mm to about 2.3 mm, about 1.8 mm to about 2.4 mm, about 1.8 mm to about 2.5 mm, about 1.8 mm to about 2.6 mm, about 1.8 mm to about 2.7 mm, about 1.8 mm to about 2.8 mm, about 1.8 mm to about 2.9 mm, about 1.8 mm to about 3.0 mm, about 1.8 mm to about 3.2 mm, about 1.8 mm to about 3.4 mm, about 1.8 mm to about 3.6 mm, about 1.8 mm to about 3.8 mm, about 1.8 mm to about 4.0 mm, about 1.8 mm to about 4.2 mm, about 1.8 mm to about 4.4 mm, about 1.8 mm to about 4.6 mm, about 1.8 mm to about 4.8 mm, about 1.8 mm to about 5.0 mm, about 1.9 mm to about 2.0 mm, about 1.9 mm to about 2.1 mm, about 1.9 mm to about 2.2 mm, about 1.9 mm to about 2.3 mm, about 1.9 mm to about 2.4 mm, about 1.9 mm to about 2.5 mm, about 1.9 mm to about 2.6 mm, about 1.9 mm to about 2.7 mm, about 1.9 mm to about 2.8 mm, about 1.9 mm to about 2.9 mm, about 1.9 mm to about 3.0 mm, about 1.9 mm to about 3.2 mm, about 1.9 mm to about 3.4 mm, about 1.9 mm to about 3.6 mm, about 1.9 mm to about 3.8 mm, about 1.9 mm to about 4.0 mm, about 1.9 mm to about 4.2 mm, about 1.9 mm to about 4.4 mm, about 1.9 mm to about 4.6 mm, about 1.9 mm to about 4.8 mm, about 1.9 mm to about 5.0 mm, about 2.0 mm to about 2.1 mm, about 2.0 mm to about 2.2 mm, about 2.0 mm to about 2.3 mm, about 2.0 mm to about 2.4 mm, about 2.0 mm to about 2.5 mm, about 2.0 mm to about 2.6 mm, about 2.0 mm to about 2.7 mm, about 2.0 mm to about 2.8 mm, about 2.0 mm to about 2.9 mm, about 2.0 mm to about 3.0 mm, about 2.0 mm to about 3.2 mm, about 2.0 mm to about 3.4 mm, about 2.0 mm to about 3.6 mm, about 2.0 mm to about 3.8 mm, about 2.0 mm to about 4.0 mm, about 2.0 mm to about 4.2 mm, about 2.0 mm to about 4.4 mm, about 2.0 mm to about 4.6 mm, about 2.0 mm to about 4.8 mm, about 2.0 mm to about 5.0 mm, about 2.1 mm to about 2.2 mm, about 2.1 mm to about 2.3 mm, about 2.1 mm to about 2.4 mm, about 2.1 mm to about 2.5 mm, about 2.1 mm to about 2.6 mm, about 2.1 mm to about 2.7 mm, about 2.1 mm to about 2.8 mm, about 2.1 mm to about 2.9 mm, about 2.1 mm to about 3.0 mm, about 2.1 mm to about 3.2 mm, about 2.1 mm to about 3.4 mm, about 2.1 mm to about 3.6 mm, about 2.1 mm to about 3.8 mm, about 2.1 mm to about 4.0 mm, about 2.1 mm to about 4.2 mm, about 2.1 mm to about 4.4 mm, about 2.1 mm to about 4.6 mm, about 2.1 mm to about 4.8 mm, about 2.1 mm to about 5.0 mm, about 2.2 mm to about 2.3 mm, about 2.2 mm to about 2.4 mm, about 2.2 mm to about 2.5 mm, about 2.2 mm to about 2.6 mm, about 2.2 mm to about 2.7 mm, about 2.2 mm to about 2.8 mm, about 2.2 mm to about 2.9 mm, about 2.2 mm to about 3.0 mm, about 2.2 mm to about 3.2 mm, about 2.2 mm to about 3.4 mm, about 2.2 mm to about 3.6 mm, about 2.2 mm to about 3.8 mm, about 2.2 mm to about 4.0 mm, about 2.2 mm to about 4.2 mm, about 2.2 mm to about 4.4 mm, about 2.2 mm to about 4.6 mm, about 2.2 mm to about 4.8 mm, about 2.2 mm to about 5.0 mm, about 2.3 mm to about 2.4 mm, about 2.3 mm to about 2.5 mm, about 2.3 mm to about 2.6 mm, about 2.3 mm to about 2.7 mm, about 2.3 mm to about 2.8 mm, about 2.3 mm to about 2.9 mm, about 2.3 mm to about 3.0 mm, about 2.3 mm to about 3.2 mm, about 2.3 mm to about 3.4 mm, about 2.3 mm to about 3.6 mm, about 2.3 mm to about 3.8 mm, about 2.3 mm to about 4.0 mm, about 2.3 mm to about 4.2 mm, about 2.3 mm to about 4.4 mm, about 2.3 mm to about 4.6 mm, about 2.3 mm to about 4.8 mm, about 2.3 mm to about 5.0 mm, about 2.4 mm to about 2.5 mm, about 2.4 mm to about 2.6 mm, about 2.4 mm to about 2.7 mm, about 2.4 mm to about 2.8 mm, about 2.4 mm to about 2.9 mm, about 2.4 mm to about 3.0 mm, about 2.4 mm to about 3.2 mm, about 2.4 mm to about 3.4 mm, about 2.4 mm to about 3.6 mm, about 2.4 mm to about 3.8 mm, about 2.4 mm to about 4.0 mm, about 2.4 mm to about 4.2 mm, about 2.4 mm to about 4.4 mm, about 2.4 mm to about 4.6 mm, about 2.4 mm to about 4.8 mm, about 2.4 mm to about 5.0 mm, about 2.5 mm to about 2.6 mm, about 2.5 mm to about 2.7 mm, about 2.5 mm to about 2.8 mm, about 2.5 mm to about 2.9 mm, about 2.5 mm to about 3.0 mm, about 2.5 mm to about 3.2 mm, about 2.5 mm to about 3.4 mm, about 2.5 mm to about 3.6 mm, about 2.5 mm to about 3.8 mm, about 2.5 mm to about 4.0 mm, about 2.5 mm to about 4.2 mm, about 2.5 mm to about 4.4 mm, about 2.5 mm to about 4.6 mm, about 2.5 mm to about 4.8 mm, about 2.5 mm to about 5.0 mm, about 2.6 mm to about 2.7 mm, about 2.6 mm to about 2.8 mm, about 2.6 mm to about 2.9 mm, about 2.6 mm to about 3.0 mm, about 2.6 mm to about 3.2 mm, about 2.6 mm to about 3.4 mm, about 2.6 mm to about 3.6 mm, about 2.6 mm to about 3.8 mm, about 2.6 mm to about 4.0 mm, about 2.6 mm to about 4.2 mm, about 2.6 mm to about 4.4 mm, about 2.6 mm to about 4.6 mm, about 2.6 mm to about 4.8 mm, about 2.6 mm to about 5.0 mm, about 2.7 mm to about 2.8 mm, about 2.7 mm to about 2.9 mm, about 2.7 mm to about 3.0 mm, about 2.7 mm to about 3.2 mm, about 2.7 mm to about 3.4 mm, about 2.7 mm to about 3.6 mm, about 2.7 mm to about 3.8 mm, about 2.7 mm to about 4.0 mm, about 2.7 mm to about 4.2 mm, about 2.7 mm to about 4.4 mm, about 2.7 mm to about 4.6 mm, about 2.7 mm to about 4.8 mm, about 2.7 mm to about 5.0 mm, about 2.8 mm to about 2.9 mm, about 2.8 mm to about 3.0 mm, about 2.8 mm to about 3.2 mm, about 2.8 mm to about 3.4 mm, about 2.8 mm to about 3.6 mm, about 2.8 mm to about 3.8 mm, about 2.8 mm to about 4.0 mm, about 2.8 mm to about 4.2 mm, about 2.8 mm to about 4.4 mm, about 2.8 mm to about 4.6 mm, about 2.8 mm to about 4.8 mm, about 2.8 mm to about 5.0 mm, about 2.9 mm to about 3.0 mm, about 2.9 mm to about 3.2 mm, about 2.9 mm to about 3.4 mm, about 2.9 mm to about 3.6 mm, about 2.9 mm to about 3.8 mm, about 2.9 mm to about 4.0 mm, about 2.9 mm to about 4.2 mm, about 2.9 mm to about 4.4 mm, about 2.9 mm to about 4.6 mm, about 2.9 mm to about 4.8 mm, about 2.9 mm to about 5.0 mm, about 3.0 mm to about 3.2 mm, about 3.0 mm to about 3.4 mm, about 3.0 mm to about 3.6 mm, about 3.0 mm to about 3.8 mm, about 3.0 mm to about 4.0 mm, about 3.0 mm to about 4.2 mm, about 3.0 mm to about 4.4 mm, about 3.0 mm to about 4.6 mm, about 3.0 mm to about 4.8 mm, about 3.0 mm to about 5.0 mm, about 3.2 mm to about 3.4 mm, about 3.2 mm to about 3.6 mm, about 3.2 mm to about 3.8 mm, about 3.2 mm to about 4.0 mm, about 3.2 mm to about 4.2 mm, about 3.2 mm to about 4.4 mm, about 3.2 mm to about 4.6 mm, about 3.2 mm to about 4.8 mm, about 3.2 mm to about 5.0 mm, about 3.4 mm to about 3.6 mm, about 3.4 mm to about 3.8 mm, about 3.4 mm to about 4.0 mm, about 3.4 mm to about 4.2 mm, about 3.4 mm to about 4.4 mm, about 3.4 mm to about 4.6 mm, about 3.4 mm to about 4.8 mm, about 3.4 mm to about 5.0 mm, about 3.6 mm to about 3.8 mm, about 3.6 mm to about 4.0 mm, about 3.6 mm to about 4.2 mm, about 3.6 mm to about 4.4 mm, about 3.6 mm to about 4.6 mm, about 3.6 mm to about 4.8 mm, about 3.6 mm to about 5.0 mm, about 3.8 mm to about 4.0 mm, about 3.8 mm to about 4.2 mm, about 3.8 mm to about 4.4 mm, about 3.8 mm to about 4.6 mm, about 3.8 mm to about 4.8 mm, about 3.8 mm to about 5.0 mm, about 4.0 mm to about 4.2 mm, about 4.0 mm to about 4.4 mm, about 4.0 mm to about 4.6 mm, about 4.0 mm to about 4.8 mm, about 4.0 mm to about 5.0 mm, about 4.2 mm to about 4.4 mm, about 4.2 mm to about 4.6 mm, about 4.2 mm to about 4.8 mm, about 4.2 mm to about 5.0 mm, about 4.4 mm to about 4.6 mm, about 4.4 mm to about 4.8 mm, about 4.4 mm to about 5.0 mm, about 4.6 mm to about 4.8 mm, about 4.6 mm to about 5.0 mm, or about 4.8 mm to about 5.0 mm.

Fundamentally, it will be appreciated that the primary lumen 60 is configured or sized and shaped to accommodate an endoscope or like instrument now known or later developed and both the primary lumen 60 and the secondary lumen 70 are configured or sized and shaped to accommodate foreign material to be retrieved from a patient's G.I. tract, such as a food impaction or foreign object, again, more about which is said below regarding the use illustrated in FIGS. 8A-8J. Those skilled in the art will appreciate that a variety of configurations and sizes of such lumens and walls beyond those shown and described and dimensionally characterized herein may be employed according to aspects of the present specification to suit particular clinical contexts, both in terms of treatment and the endoscope or other equipment to be used, such that the foregoing dimensional call-outs are to be understood as illustrative and non-limiting.

Any such overtube device 20 as shown and described herein may be single-use or multi-use and sold, supplied, or used "packaged clean" or "sterile" depending on the clinical context and applicable regulations in place at the time, noting that the device 20 itself is never intended to enter the anatomy but devices passing therethrough will. The design and materials of construction of the device 20 contemplated herein, in whole or in part, do or can accommodate any such indications for use according to aspects of the present invention without departing from its spirit and scope.

Figure 8A:
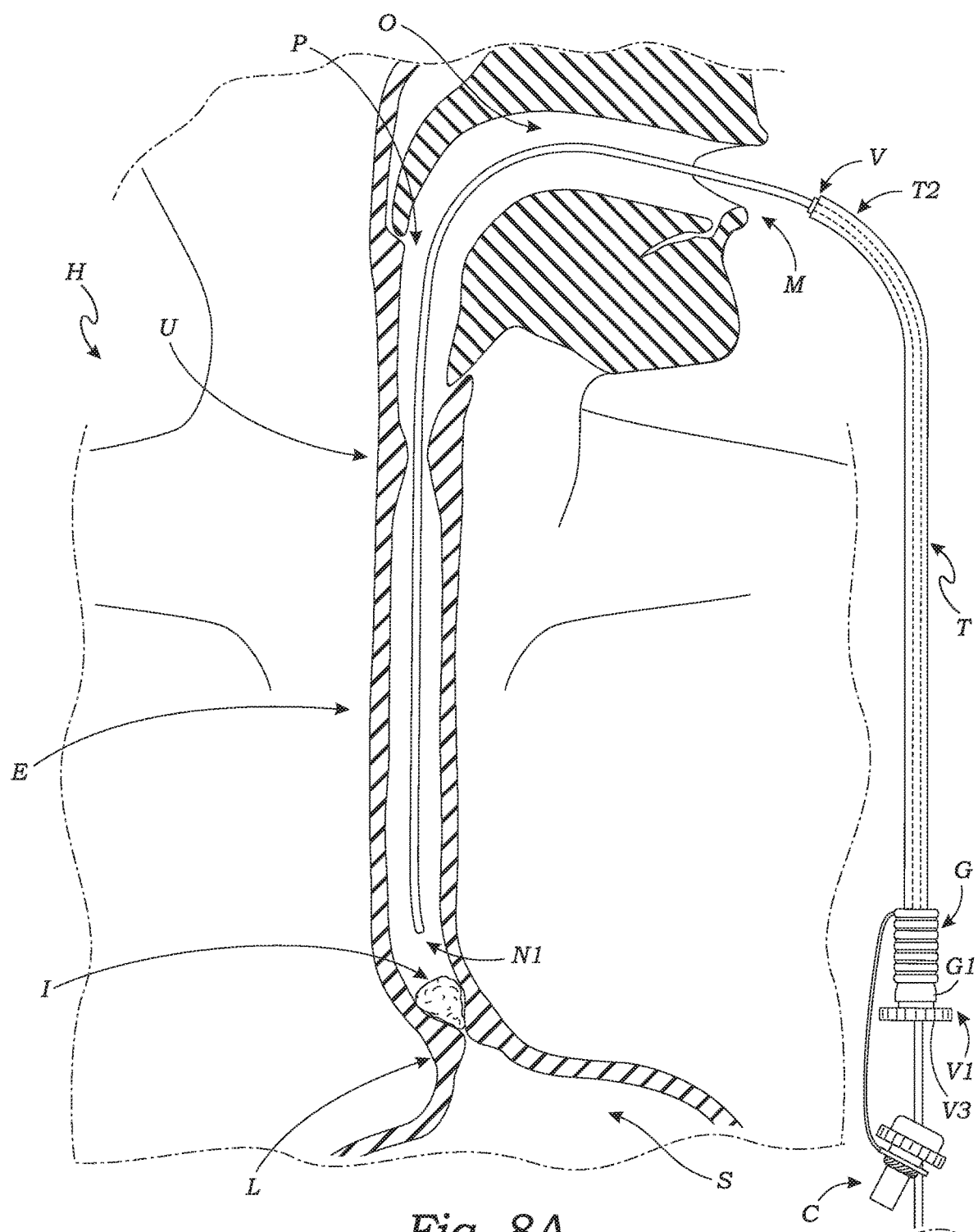
FIG. 8A illustrates the prior art insertion of an endoscope through an overtube assembly to a first location within the esophagus.
Figure 8B:
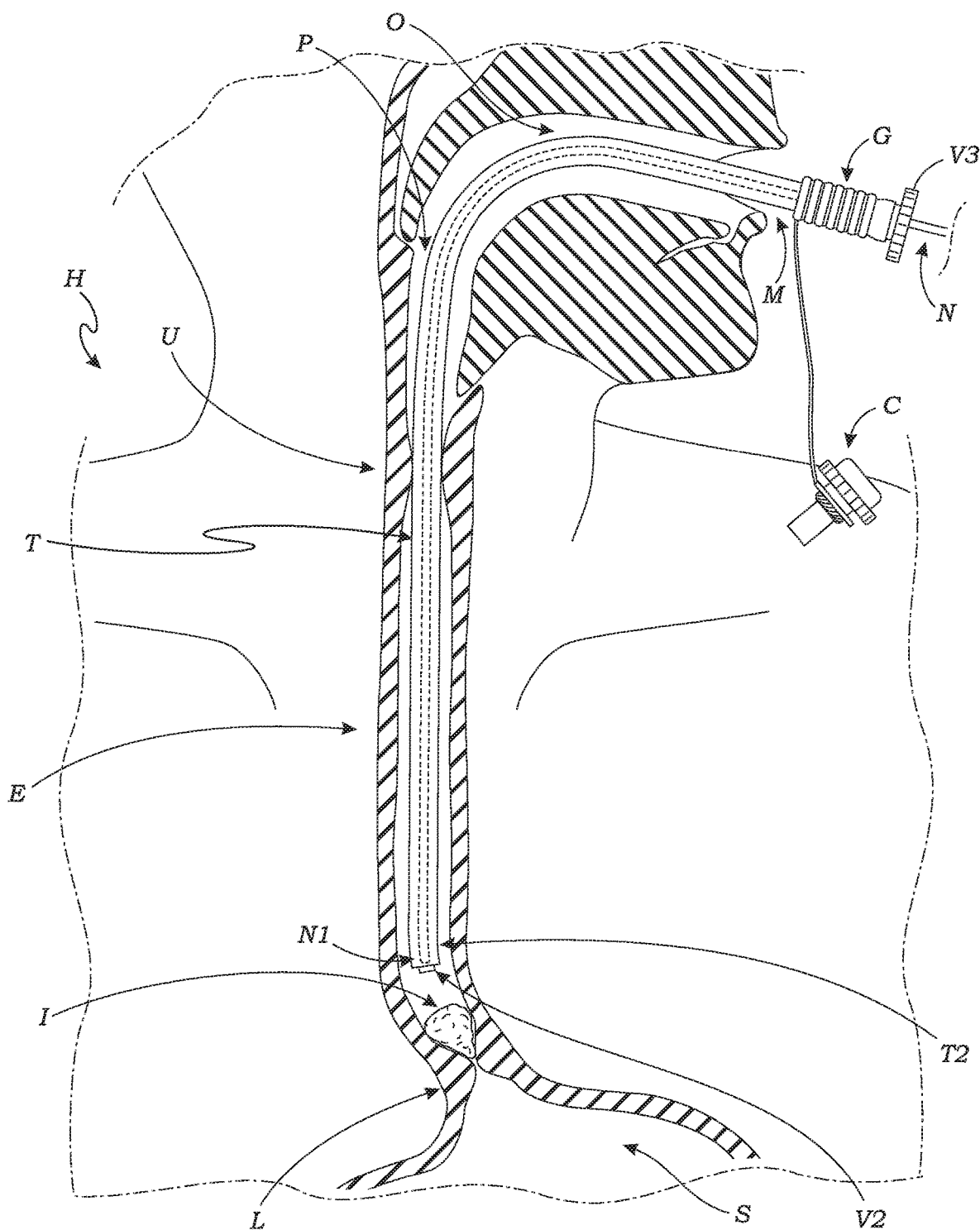
FIG. 8B illustrates the prior art insertion of the overtube assembly over the endoscope to the first location within the esophagus.
Figure 8C:
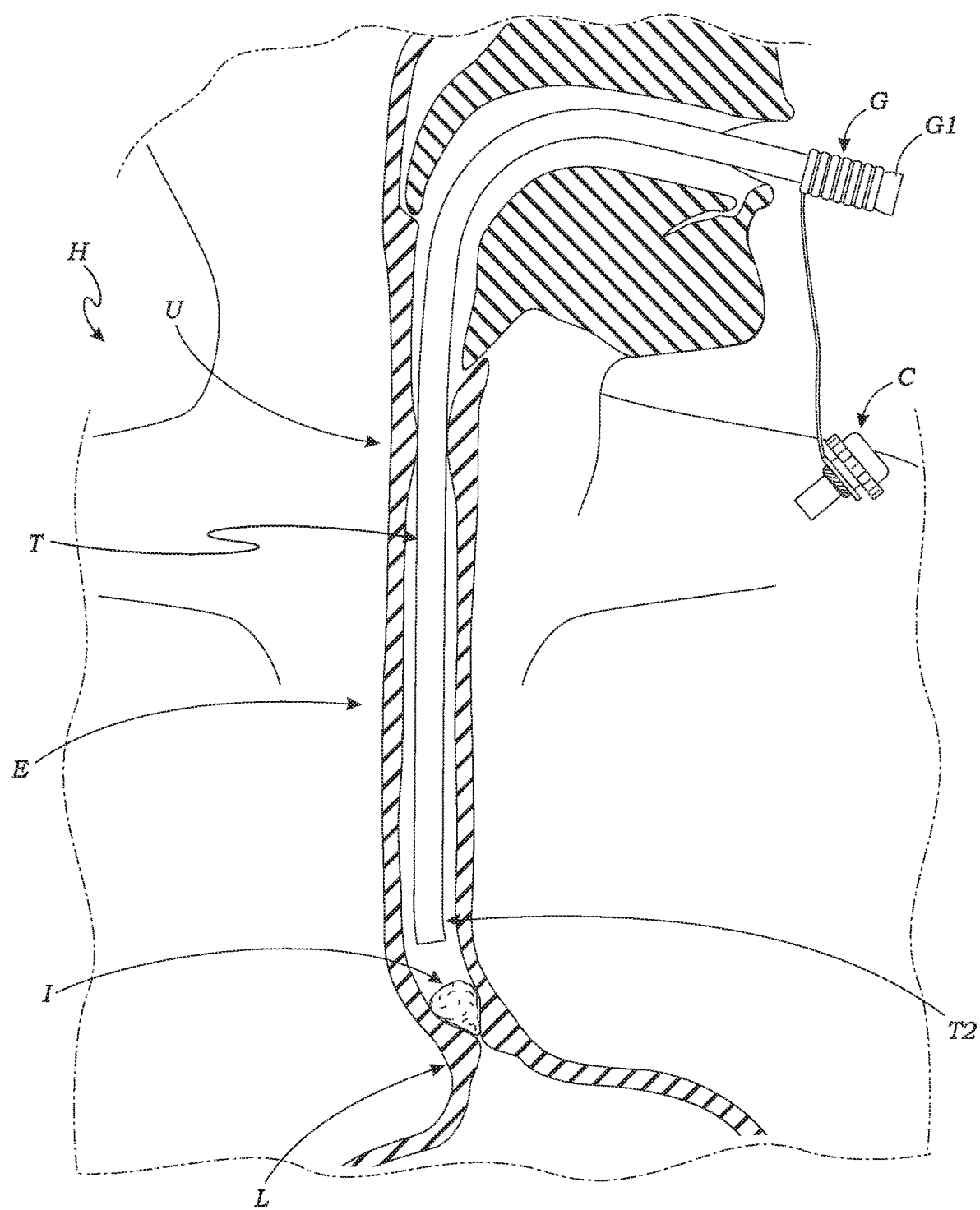
FIG. 8C illustrates the prior art insertion of the overtube still at the first location within the esophagus now with the endoscope and an inner tube of the overtube assembly removed.

Turning now to FIGS. 8A-8J, there are shown schematic illustrations of the exemplary device 20 of FIGS. 3 and 4 in use in conjunction with an overtube T, as through a series of steps as might be performed by a clinician in inserting the overtube T within the esophagus E at various locations and in various modes of operation. As a threshold matter, it is noted that schematically represented is again the GUARDUS® overtube T having a grip portion G at its proximal end having an overtube cap T tethered thereto, here nominally of the "esophageal" configuration with a nominal length of 25 cm, though once again such drawings not being taken to scale and, more generally, any overtube or other such device now known or later developed may be employed in conjunction with an overtube device 20 according to aspects of the present invention without departing from its spirit and scope. As illustrated, the overtube T is employed with a conventional endoscope N having a nominal diameter of 10 mm and length of 50 cm. In FIGS. 8A-8C there is shown a general three-step process for placing the overtube T within the esophagus E in a manner generally known and practiced in the art, hence the "Prior Art" label on these three figures. As a preliminary step of preparing the exemplary overtube T for insertion, not illustrated, an inner tube V is slidably inserted within the main (outer) overtube T and secured in place by engaging an inner tube cap V3 located at the proximal end V1 of the inner tube V with the proximal grip portion G of the overtube T, as through a threaded engagement specifically with the grip connector G1, it being appreciated that the inner tube cap V3 may be formed with an external thread (not shown) configured to engage the internal thread G2 (FIG. 5) of the overtube grip portion G in much the same way that the overtube cap C engages the grip G. The inner tube V is sized and configured, and selected accordingly along with the overtube T and its cap C, to accommodate a particular size (diameter) endoscope, such that the distal end V2 of the inner tube V protrudes just beyond the distal end T2 of the overtube T when the inner tube V is fully seated within the overtube T, thereby providing a somewhat net fit about the outside of the scope N and a stepped or tapered leading edge from the O.D. of the scope N to the O.D. of the overtube T. Sterile or biocompatible lubricant may be applied to any such components before inserting one into the other or any of them within the anatomy. Back to the three-step process for inserting the overtube T, first, with reference to FIG. 8A, with the overtube T prepped with the inner tube V as above-described, the endoscope N is slidably inserted into the proximal end V1 of the inner tube V and advanced therethrough until the entire overtube T is located substantially proximally on or along the endoscope N. The endoscope N is then intubated by being passed through the mouth M and into the esophagus E of the patient H as by inserting the scope N, and particularly its distal tip N1, into the oral cavity O and following the hard palate down past the pharynx P and through the upper esophageal sphincter U in a manner generally known in the art for passing an endoscope or other such device into the esophagus E or stomach S. As shown, the endoscope N is inserted until its distal tip N1 has passed through the upper esophageal sphincter U and down through the esophagus E to a location just above a food impaction I at the lower esophageal sphincter L. Of course, it will be appreciated that the depth of the insertion of the endoscope N will essentially be dictated by the location of the food impaction I or other G.I. issue, such that the presently illustrated use is merely exemplary and non-limiting. Second, as illustrated in FIG. 8B, with the scope N positioned as shown in FIG. 8A, the overtube T is advanced along the endoscope N, serving much like a guidewire, and through the upper esophageal sphincter U and into the esophagus E, down to the location of the endoscope tip N1, basically rendering the overtube and inner tube distal ends T2, V2 adjacent to the endoscope distal tip N1. Third, as shown in FIG. 8C, with the overtube T so positioned within the esophagus E just above the illustrated food impaction I, the endoscope N and inner tube V are simply removed, as by disconnecting the inner tube cap V3 from the overtube grip portion G and slidably withdrawing the inner tube V and the scope N together, again, leaving the overtube T in place within the anatomy essentially just where it was.

Figure 8D:
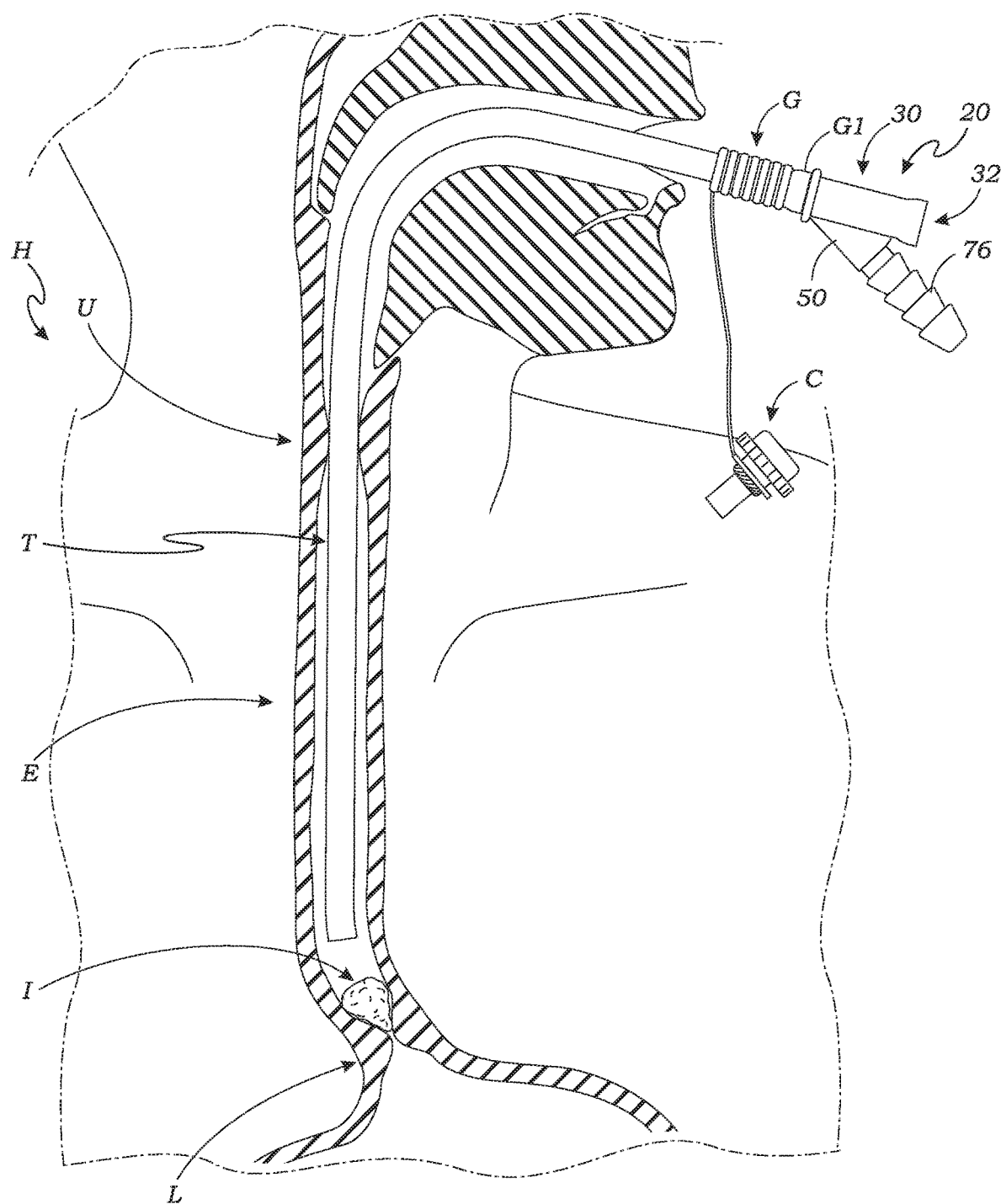
FIG. 8D illustrates attachment of an exemplary overtube device as shown in FIGS. 3 and 4 on a grip portion formed at the proximal end of the overtube.
Figure 8E:
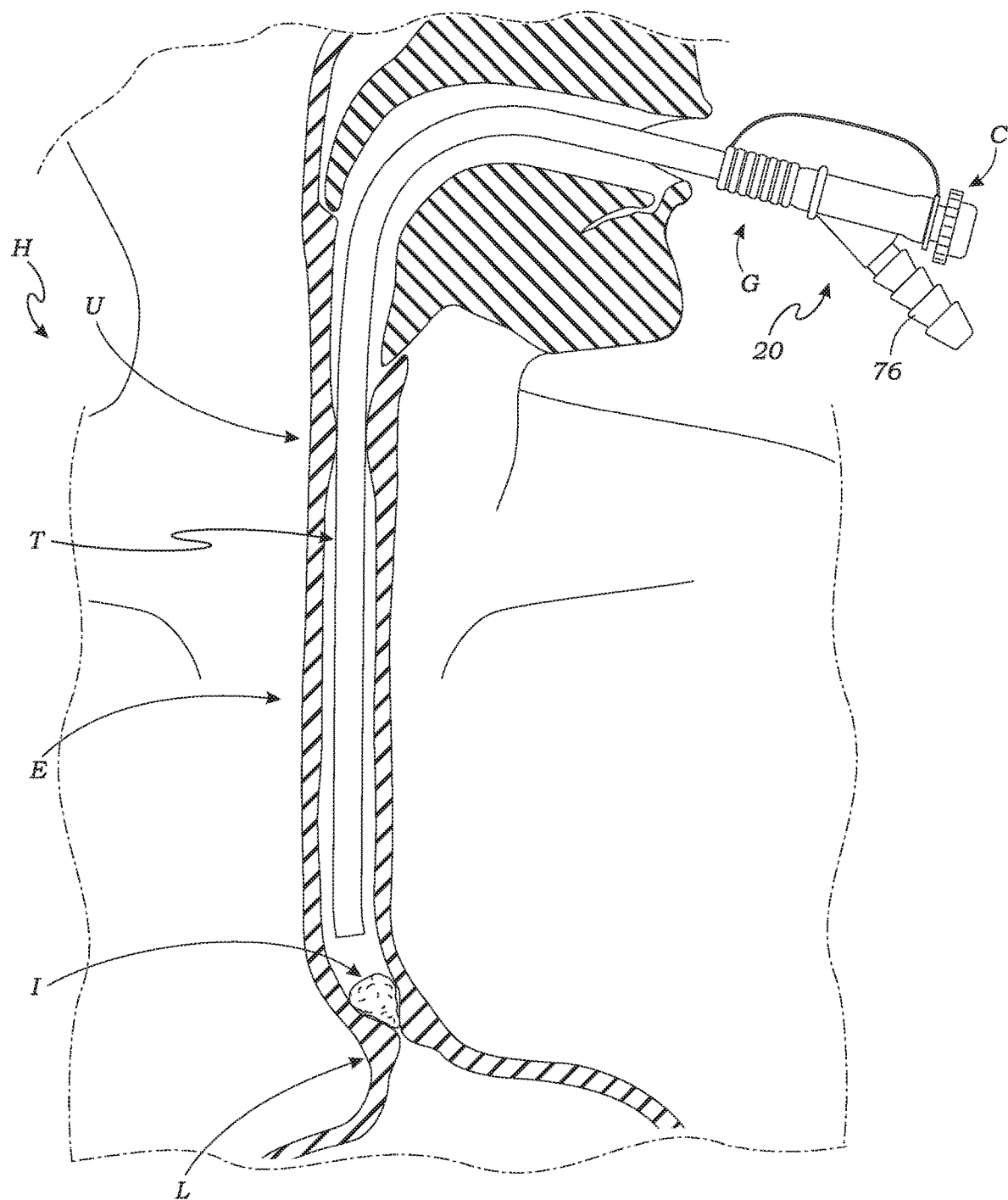
FIG. 8E illustrates attachment of a tethered overtube cap of the grip portion of the overtube on the proximal end of the overtube device.
Figure 8F:
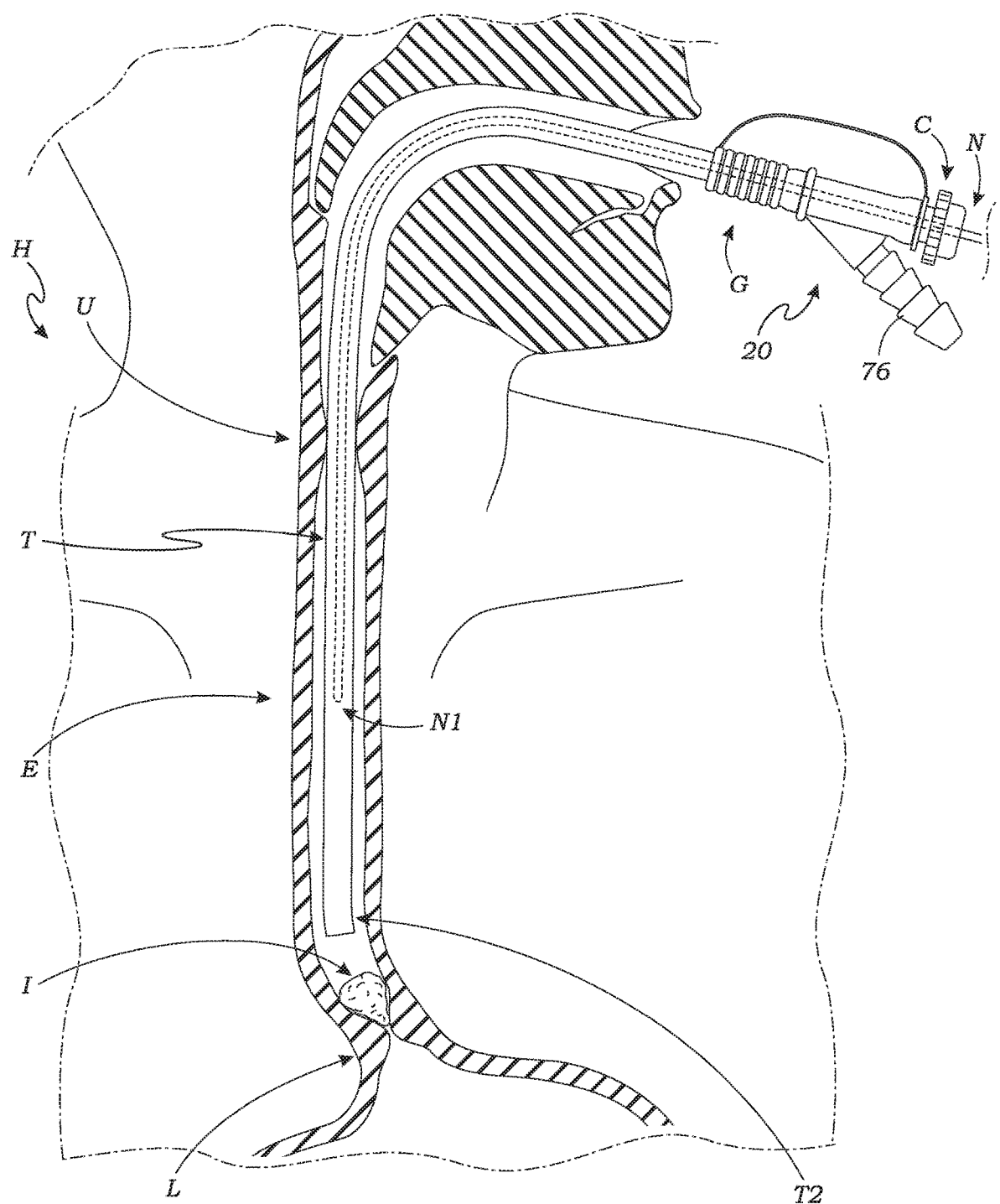
FIG. 8F illustrates re-insertion of the endoscope through the overtube cap and the overtube device and into the overtube down to a second location within the esophagus proximal of the first location.

Referring next to FIG. 8D, with the overtube T within the anatomy as above-described in connection with FIGS. 8A-8C, the overtube device 20 is then installed on the overtube T to effectively convert it into a suction or foreign material retrieval device. Specifically, as shown, and will be further appreciated with reference to FIGS. 5-7 discussed above, the distal portion 44 of the overtube device 20 is inserted within the connector G1 of the proximal grip portion G of the overtube T. Again, in the illustrated embodiment, this is accomplished by engaging the external thread 46 with the internal thread G2 of the grip portion G, though it will be appreciated that any other temporary engagement means now known or later developed for selectively joining the distal end 24 of the device 20 with the proximal end of an overtube T may be employed without departing from the spirit and scope of the invention. The proximal opening 32 of the device 20 remains open, as does the barb fitting 76 associated with the suction port 50. Next, as shown in FIG. 8E, the overtube cap C that is tethered to and has to this point been hanging freely from the grip portion G of the overtube T may be engaged with the proximal end 22 of the device 20. Specifically, as above-described, the external thread C3 of the tethered overtube cap C is engaged with the internal thread 36 formed within the proximal opening 32 at the proximal portion 42 of the device 20, though once more, other means of temporary engagement now known or later developed may be employed. Once so installed on the proximal end T1 of the overtube T and with the overtube cap C installed thereon, such that the device 20 is effectively installed between the overtube grip G and cap C that otherwise would be installed together, the device 20 is in position to facilitate applying suction to the overtube T. First, optionally but preferably, though ultimately depending on the clinical indications, as shown in FIG. 8F, the endoscope N may be reinserted now through the overtube cap C and then the device 20, through the primary lumen 60 (FIGS. 2, 4, and 7) and on down the overtube T. As illustrated, the scope N can be advanced to an intermediate point within the overtube T some distance proximal of its distal end T2, or here with the distal tip N1 at a location between the upper and lower esophageal sphincters U, L, so as to provide at least visualization to the distal end T2 of the overtube T and the food impaction I beyond, without necessarily being too close to the distal end T2 so as to potentially interfere with the suction or retrieval event. However, those skilled in the art will once again appreciate that the endoscope N can ultimately be advanced to any location deemed clinically advisable, and specifically may be advanced to and beyond the distal end T2 of the overtube T such as for improved visualization of the food impaction I or other foreign body as well as the surrounding anatomy. A distally advanced scope N may also then deploy a tool, for example, to break up the food impaction I or to attempt to retrieve some other foreign object, whether with vacuum assistance or not, noting that at this point in the description or sequence of illustrated steps the suction system 80 (FIGS. 8G-8J) has not yet been connected to the device 20, though it could have and, fundamentally, those skilled in the art will appreciate that such manipulation and use of the endoscope N can be accomplished before, during, or after the suction system 80 is connected and/or operated, it following that many of the described steps can be carried out in an order other than here described. By way of example and not limitation, the suction system 80 could have already been connected to the device 20, at least prior to installation of the overtube cap C on the device 20, or perhaps even prior to connecting the device 20 to the overtube T.

Figure 8G:
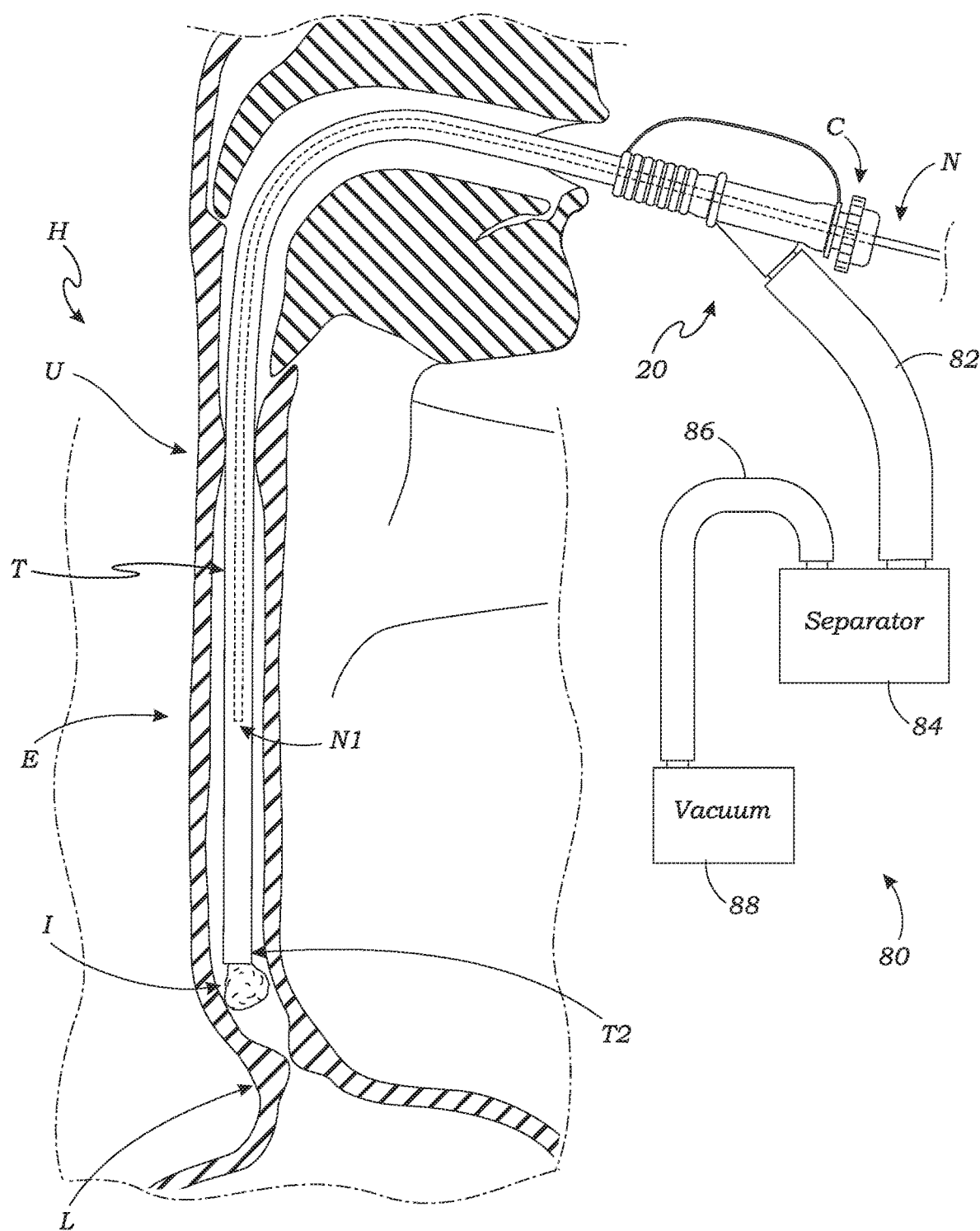
FIG. 8G illustrates attachment of a suction system to a suction port of the overtube device and suction then applied through the overtube device to the overtube so as to pull a food impaction into the distal end of the overtube.

Turning now to FIG. 8G, an exemplary suction system 80 to be employed in conjunction with the overtube device 20 according to aspects of the present invention is shown schematically as generally comprising a separator 84 and a vacuum source 88. A first suction line 82 connects the separator 84 to the barb fitting 76 and thereby to the suction port 50 of the device 20. Preferably, the first suction line 82 would have an inside diameter at least as large as that of the secondary lumen 70, and potentially the primary lumen 60 and the overtube T itself as well, which follows at least with respect to the secondary lumen 70 since the first suction line 82 is pushed over the barb fitting 76 in the exemplary embodiment. In this way, any food impaction I or other foreign material that can travel up the overtube T and through the device 20 under suction would also be able to pass through the first suction line 82 and into the separator 84, more about which is said below in connection with FIGS. 8I and 8J. A second suction line 86 connects or leads from the separator 84 to the vacuum source 88. As shown, the second suction line 86 may be relatively smaller than the first suction line 82, since any solid or semi-solid materials and even liquids would be entrained within the separator 84 and only air or other gas would then pass out of the separator 84 to the vacuum source 88 through the second suction line 86. Relatedly, as also illustrated schematically, both the first and second suction lines 82, 86 connect at the top of the separator 84, so as to effectuate gravity separation of solids and liquids into the bottom or basin of the separator 84. The volume of the separator 84 can vary widely depending on the clinical context and other factors, though it would preferably be at least approximately 1 cup or about 0.2 quart or 230 cm$^3$. Those skilled in the art will appreciate that any other such means of separation now known or later developed, including but not limited to filtration and centrifuge, may be employed in the present invention, and the suction system 80, specifically, without departing from its spirit and scope. With continued reference to the suction system 80 depicted in FIG. 8G, those skilled in the art will further appreciate that the vacuum source 88 may be any device now known or later developed capable of creating suction or vacuum or a negative pressure, including but not limited to a portable or stand-alone vacuum pump or other such unit and a relatively larger, permanently installed facility- or area-wide vacuum source as accessed through a wall connection, such as a standard ¼" connection/line (not shown). Any such vacuum source 88 may be capable of producing suction or negative/vacuum pressure of up to approximately 29 in Hg or 14 psi.

Figure 8H:
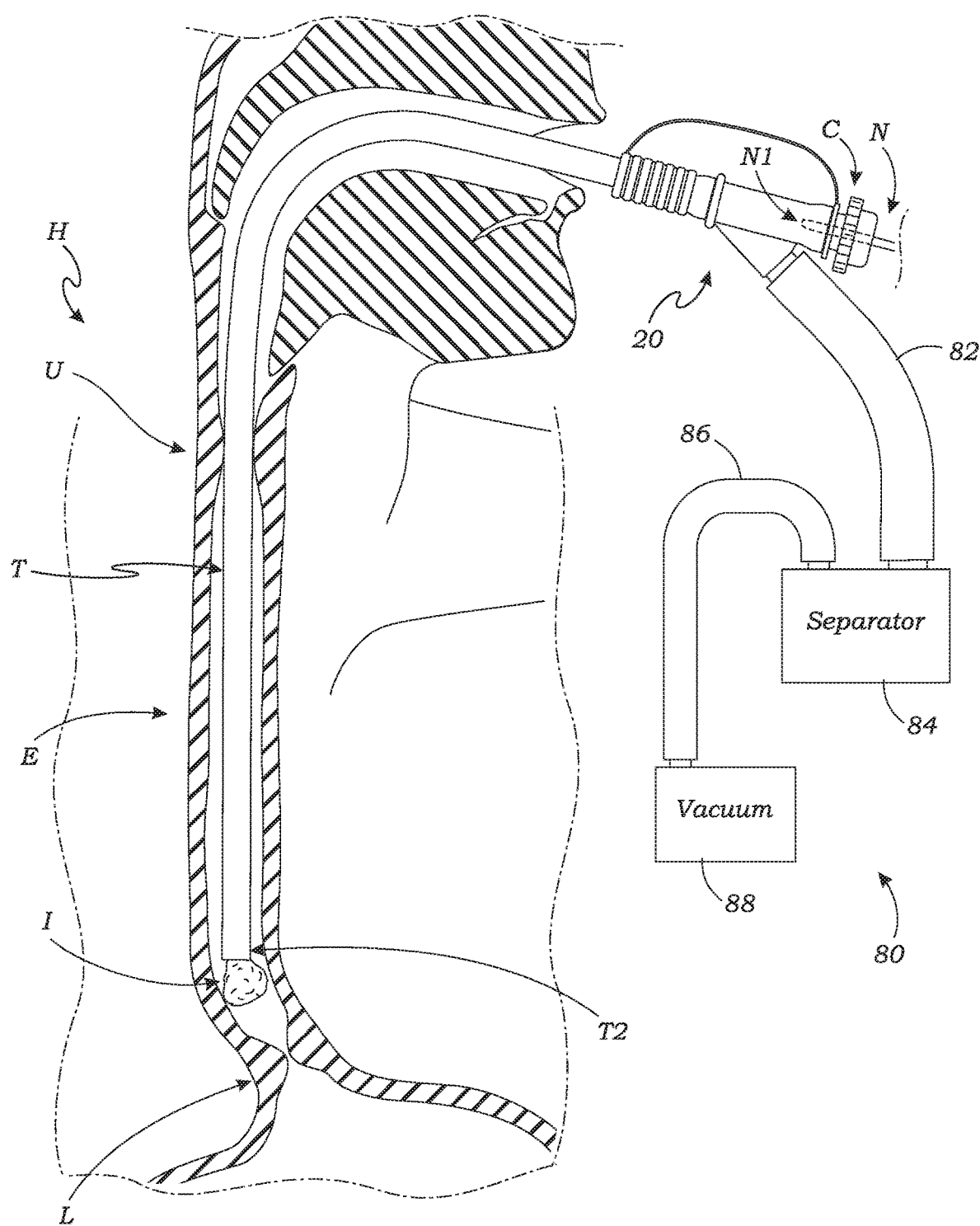
FIG. 8H illustrates continued suction applied to the overtube via the suction system acting through the overtube device, now with the endoscope withdrawn from the esophagus to the proximal end of the overtube device.
Figure 8I:
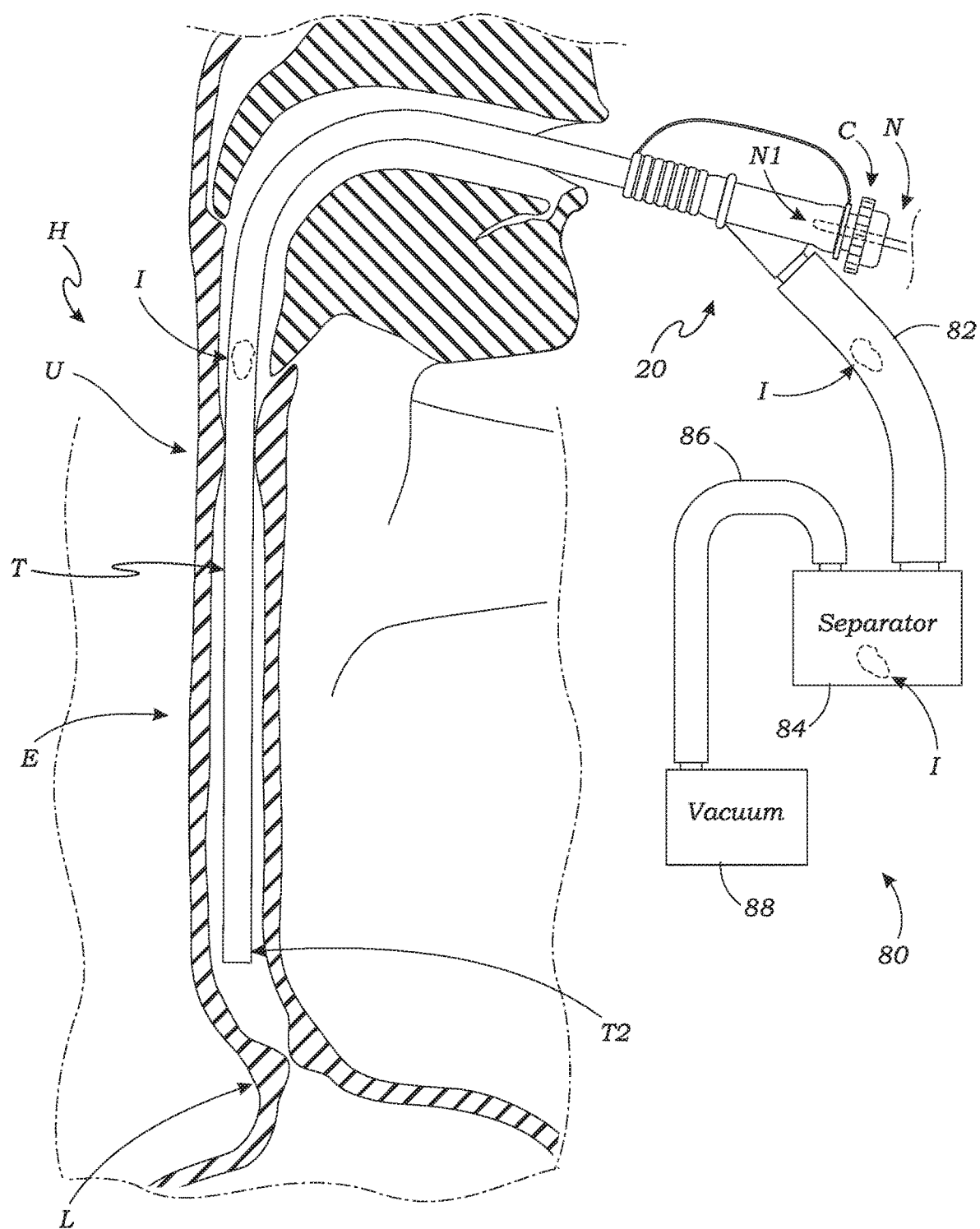
FIG. 8I illustrates continued suction applied to the overtube via the suction system acting through the overtube device, now with the food impaction breaking up and moving through the overtube and overtube device and into the suction system.
Figure 8J:
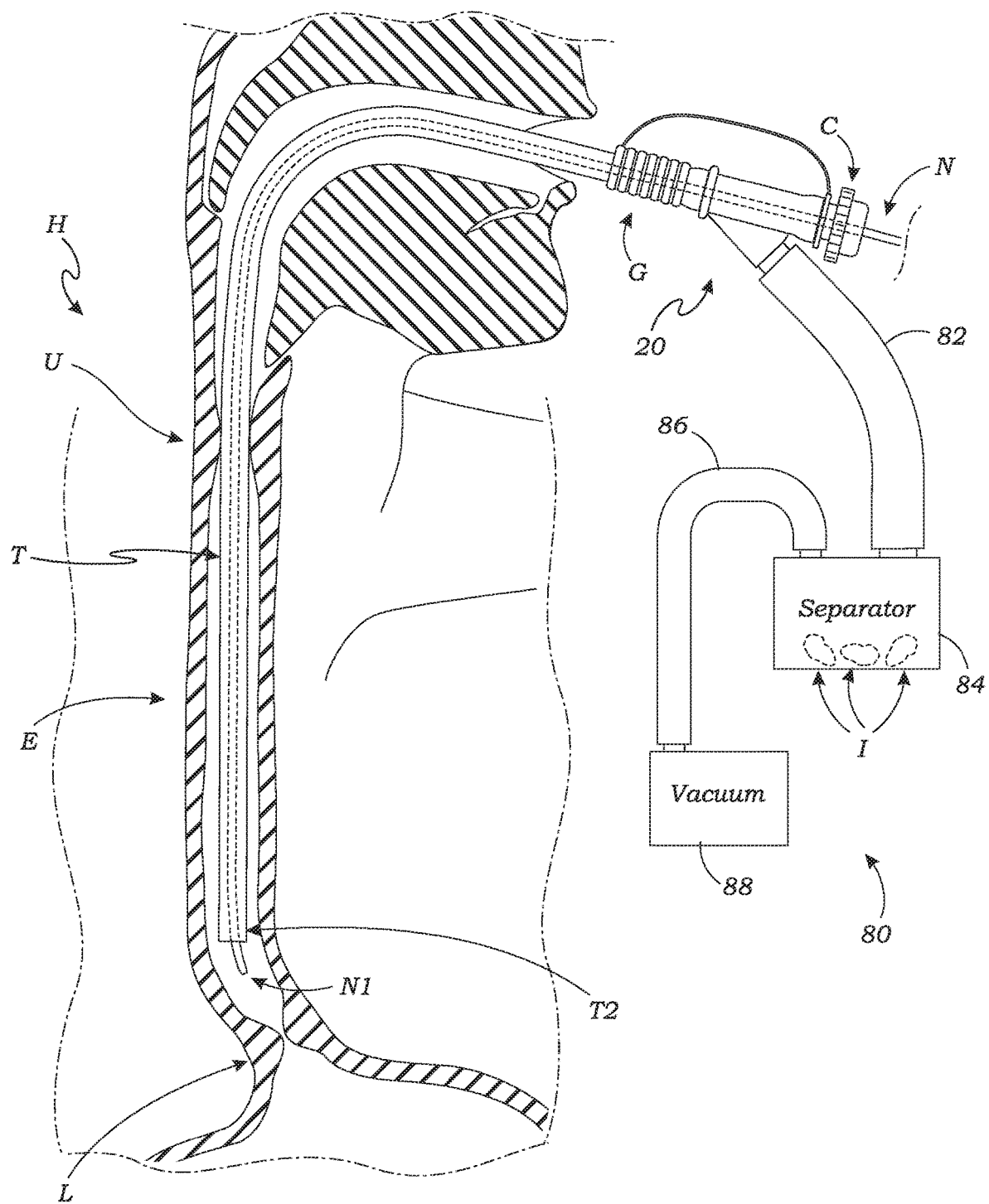
FIG. 8J illustrates all of the food impaction now in the suction system and the endoscope re-advanced through the overtube device and overtube to the first location within the esophagus.

With the exemplary suction system 80 so configured and installed in conjunction with the device 20, as again by connecting the first suction line 82 to the barb fitting 76 of the suction port 50 of the device 20 and ultimately to the vacuum source 88 through the separator 84, with continued reference to FIG. 8G, it will be appreciated that once the vacuum source 88 is "turned on" or operated, a suction or vacuum pressure would then be applied throughout, or again through the device 20 and the connected overtube T down to its distal end T2. Accordingly, as illustrated schematically, the food impaction I is sucked into the distal end T2 of the overtube T. At this point, as illustrated, the endoscope N is still advanced within the overtube T for visualization of what is happening at its distal end T2. Then, as continued suction is applied, while the food impaction I may remain at the distal end T2 of the overtube T as shown in FIG. 8H or may begin to break up and move to an intermediate location within the overtube T, the endoscope N may be withdrawn, either to some more proximal position or, as shown, out of the overtube T altogether such that its distal tip N1 is still within the overtube cap C and within the device 20 at a location proximal of the suction port 50 so as to not interfere with the continued migration or retrieval of the food impaction I or other such material under substantially continuous suction. In this manner, it will be appreciated that while not at all blocking any part of the flow path out of the overtube T and through the device 20, the endoscope N may still visualize any such retrieved materials passing through the device 20 into the suction system 80. Those skilled in the art will also appreciate that the use of suction and the use of an endoscope itself to retrieve foreign material are not mutually exclusive; for example, the endoscope N may be advanced distally and deploy a tool to facilitate removal with suction or vacuum assistance, such as a tool to grasp the foreign material or a tool to dissect or cut up the foreign material, as may be the case with more solid and/or relatively larger foreign materials, whereas suction alone may be sufficient and/or preferable for the typical semi-solid food impaction I. Any and all such possibilities are within the realm of clinical application employing a device 20 in accordance with aspects of the present invention in conjunction with an overtube T or the like. Turning briefly to FIG. 8I, there is shown the food impaction I now broken up, again, whether due to the vacuum alone or also based on the temporary deployment of the scope N, the dispensation of a chemical or biological additive, or any other such technique now known or later developed. As illustrated just for example, the food impaction I is in three discrete parts, one still within the overtube T at an intermediate location, one within the first suction line 82 between the suction port 50 of the device 20 and the separator 84, and one already in the separator 84. Finally, as shown in FIG. 8J, all three portions of the food impaction I are now in the separator 84 and the endoscope N has been advanced again through the device 20 and the overtube T, here such that the distal tip N1 of the scope N is advanced out of the distal end T2 of the overtube T so as to visualize the area where the food impaction I was, such as to confirm that all has been removed and to examine the anatomy for any signs of trauma or other G.I. complication or condition. It will be appreciated that the visualization of the food impaction I, its removal, and post-removal endoscopic inspection are all achieved effectively and efficiently through essentially a single intubation event, namely, passage of the endoscope N into the anatomy followed by the overtube T as above-described in connection with FIGS. 8A-8C, made possible by the new and novel overtube device 20 according to aspects of the present invention that essentially converts the overtube T to a suction and foreign body retrieval tool, thereby serving the two-fold purpose of protecting the anatomy while removing the foreign material. Again, those skilled in the art will appreciate that other forms of the device 20, in part, again, depending on the configuration of the related overtube T and scope N with which the device 20 is to be used, are possible without departing from the spirit and scope of the invention. By way of further example and not limitation, it will be appreciated that a "purpose-built" overtube device can be constructed essentially by incorporating the device 20 or something similar permanently into the overtube T at its proximal end T1, such as by modifying the grip portion G accordingly to have the device 20 integral therewith or even replacing the grip portion G entirely with a device 20 according to aspects of the present invention permanently installed on the overtube T, with the overtube cap C then simply tethered to the device 20 rather than the grip portion G. Or, put another way, the grip portion G would effectively be reconfigured to include a suction port according to aspects of the present invention, or a port of sufficient size and selectively connectable to a vacuum source for applying suction to the main lumen of the overtube T for food impaction I or other foreign body removal. As a further example, rather than a separately tethered overtube cap C, the relevant structure, including any seal or wiper gasket C5 or the like, may be formed integrally with the device 20 at its proximal end, with any overtube cap C tethered to the grip portion G of an overtube T, where such overtube is "off the shelf" in that configuration, simply not being needed or employed when the overtube device 20 is instead connected to the proximal end of the overtube T.

In any of the foregoing embodiments or other related embodiments, it will be appreciated that any other tools or techniques now known or later developed for addressing particularly a food impaction, such as means by which the impaction is sectioned into smaller portions, softened, etc., may be employed in combination with an overtube device according to aspects of the present invention.

EXAMPLES

The following non-limiting examples are provided for illustrative purposes only in order to facilitate a more complete understanding of the disclosed subject matter. These examples should not be construed to limit any of the embodiments described in the present specification, including those pertaining to an overtube device, kits comprising an overtube device, and/or methods and uses of such an overtube device.

Example 1

Esophageal Stricture and Food Impaction

This example demonstrates the use of an overtube device according to aspects of the present invention in the non-surgical removal of a food impaction caused by esophageal stricture.

A 61-year-old female presented with difficulty swallowing and reflux and regurgitation symptoms. Through a complete medical work-up and health history it was determined that the patient had for years been treated for cirrhosis of the liver with the scarring in the liver cutting down on blood flow in the liver and so leading to increased blood flow through the veins of the esophagus, resulting in esophageal varices. The clinician concluded pre-endoscopy that the treatment of the varices had likely led to esophageal stricture, or narrowing of the esophagus, which was likely the cause of the patient's present symptoms. The patient was prepped and sedated, and the clinician selected a standard adult endoscope having a nominal 10 mm outside diameter and a corresponding overtube having a nominal length of 25 cm for use in the procedure along with an appropriately sized proximal overtube device for selective attachment to the grip portion of the overtube in order to then apply suction to the overtube while still allowing for endoscopic visualization, which approach the clinician felt was likely sufficient assessment and to retrieve any food impaction in one pass. With the patient under sedation, the clinician first lubricated both the endoscope and the overtube, which included a slidably engaged inner tube, and then passed the endoscope therethrough. With the overtube remaining proximally located outside the anatomy, the clinician intubated the scope into the esophagus as by passing through the oral cavity and following the hard palate into and through the pharynx and then into the esophagus through the upper esophageal sphincter, advancing the scope distally just beyond the upper esophageal sphincter with its tip positioned above the food impaction that appeared originate at an intermediate location within the esophagus but had risen to a level just below the upper esophageal sphincter, explaining the patient's reflux and regurgitation symptoms. Next, the overtube was passed into the esophagus over the gastroscope, using the scope like a guidewire, until its distal end was at approximately the same location as the tip of the scope, or just into the esophagus beneath or distal of the upper esophageal sphincter, and then the scope and the inner tube of the overtube were together removed, leaving only the overtube in position. The clinician then attached the distal end of the overtube device to the proximal grip portion of the overtube and secured the overtube or insufflation cap on the opposite distal end of the overtube device. The endoscope was then reintroduced into the overtube by passing it through the overtube cap and the overtube device for visualization of the distal end of the overtube and the food impaction just beyond. Next, a vacuum pump was connected to the suction port of the overtube device, as by connecting a suction line from the vacuum pump to a separator and from the separator to the device's suction port. Then applying continuous vacuum of 150 mm Hg pressure to the overtube through the suction port of the overtube device, the clinician was able to begin suctioning the food impaction into the distal end of the overtube. Under continued suction pressure and with the scope being successively withdrawn, the food impaction was pulled up through the overtube. Eventually, the scope was withdrawn to the point where its distal tip was just inside the overtube device and cap so as to not block the device's suction port, such that under further continued vacuum the food impaction passed through the overtube device and into the separator. Temporarily turning the vacuum supply off, the endoscope was re-advanced to the distal end of the overtube, at which point the clinician could reassess. Finding that more food impaction remained, under endoscopic visualization, the overtube was advanced further distally into the esophagus, to a point just above the remaining food impaction, the scope was withdrawn into the overtube and suction reapplied as before, with the scope being withdrawn as the remaining food impaction was suctioned into the overtube under continuous vacuum and eventually into the separator. Once more, the vacuum supply was turned off and the scope re-advanced to the distal end of the overtube and beyond, the clinician this time confirming that most all of the food impaction had been removed and so now also getting a good look at the suspected esophageal stricture. Dilation was prescribed and administered to expand the esophagus in the affected area, and the patient experienced immediate and sustained relief with relatively minimal post-procedure discomfort. With a single intubation and only two suction events, all under the required visualization, the clinician was ultimately able to remove substantially all of the food impaction, or approximately two-thirds cup of semi-digested food material, and clear the esophagus, thereby also gaining complete visualization of the esophageal stricture and immediately prescribing and administering therapeutic dilation, thus providing a convenient and comprehensive treatment of the patient.

Example 2

Meat Bolus

This example demonstrates the use of an overtube device according to aspects of the present invention in the non-surgical removal of meat bolus from a patient's esophagus.

A 52-year-old male presented with diffuse chest pain or pressure, throat pain and difficulty swallowing, and a sensation of choking. Upon a complete medical work-up and examination, including a health history indicating no prior instances of trouble with ingestion and review with the patient indicating a recent meal including steak and that the symptoms began soon thereafter, the clinician concluded likely food impaction within the esophagus in the form of meat (steak) bolus and prepped the patient for endoscopy. Accordingly, the clinician selected a standard adult gastroscope having a nominal 10 mm outside diameter and a corresponding overtube having a nominal length of 50 cm for use in the procedure along with an appropriately sized proximal overtube device for selective attachment to the grip portion of the overtube in order to then apply suction to the overtube while still allowing for endoscopic visualization, which approach the clinician felt was likely sufficient to retrieve the meat bolus in one pass. With the patient under sedation, the clinician first lubricated both the gastroscope and the overtube, which included a slidably engaged inner tube, and then passed the gastroscope therethrough. With the overtube remaining proximally located outside the anatomy, the clinician intubated the scope into the esophagus as by passing through the oral cavity and following the hard palate into and through the pharynx and then into the esophagus through the upper esophageal sphincter, advancing the scope distally until its tip was positioned just above the meat bolus that appeared to be lodged on or in the lower esophageal sphincter. Next, the overtube was passed into the esophagus over the gastroscope, using the scope like a guidewire, until its distal end was at approximately the same location as the tip of the scope, and then the scope and the inner tube of the overtube were together removed, leaving only the overtube in position. The clinician then attached the distal end of the overtube device to the proximal grip portion of the overtube and secured the overtube cap on the opposite distal end of the overtube device. The gastroscope was then reintroduced into the overtube by passing it through the overtube cap and the overtube device for visualization of the distal end of the overtube and the meat bolus just beyond. Next, the hospital's vacuum system was connected to the suction port of the overtube device, as by connecting a suction line from a separator to the device's suction port, which separator is itself connected to the wall vacuum port in the operating room. Then applying continuous vacuum of 200 mm Hg pressure to the overtube through the suction port of the overtube device, the clinician was able to pull the bolus into the distal end of the overtube. Determining, as through continued endoscopic visualization, that the bolus was slightly too large to effectively suction all the way through the overtube and overtube device as a single, solid mass, under continued suction pressure, the clinician introduced an endoscopic cutting or dissection tool through a channel of the scope and proceeded to carefully cut or dissect the meat bolus into smaller parts, some of which sluffed off and were suctioned past the scope. Having completed a sufficient number of dissections or partitions of the bolus, the endoscopic cutting tool was withdrawn into the scope and the scope itself successively withdrawn, with the meat bolus then pulled up through the overtube, somewhat following the gastroscope. At this point, the scope was withdrawn to the point where its distal tip was just inside the overtube device and cap so as to not block the device's suction port, such that under still continued vacuum the meat bolus passed piecemeal through the overtube device and into the separator. At that point the vacuum supply was turned off and the gastroscope reintroduced through the overtube and out its distal end so that the clinician could get a good look at the area of the lower esophageal sphincter and confirm that the meat bolus had been fully removed and that there was no indication of injury to the anatomy or any anatomical condition that could have caused the impaction or that otherwise might require treatment. Post-procedure, the patient presented with no complications and indicated only minor throat soreness.

1. An embodiment of the present overtube attachment device is configured for selective engagement to an overtube and a suction system, the overtube attachment device further configured for selective receipt therethrough of an endoscope, the overtube device comprising: a body having an endoscope opening formed at a proximal end and an overtube opening formed at a distal end, the endoscope opening and the overtube opening being in fluid communication; a primary lumen formed through the body to interconnect the endoscope opening and the overtube opening; and a secondary lumen formed in the body so as to intersect and be in fluid communication with the primary lumen through a suction opening; wherein, in an operational configuration, the overtube is engaged with the overtube opening, the endoscope is received through the endoscope opening, and the suction system is engaged to the suction opening.

2. The overtube attachment device according to embodiment 1, wherein, in the operational configuration, an overtube cap is engaged to the endoscope opening, the endoscope is received into the endoscope opening through the overtube cap.

3. The overtube attachment device according to embodiment 1, wherein one of an internal thread or a barb fitting is formed at the suction opening.

4. The overtube attachment device according to embodiment 1, wherein one of a primary lumen inside diameter is substantially equal to a secondary lumen inside diameter or the primary lumen inside diameter is greater than the overtube inside diameter.

5. The overtube attachment device according to embodiment 4, wherein the primary lumen inside diameter is between 9 mm and 40 mm.

6. The overtube attachment device according embodiment 1, wherein intersection of the secondary lumen with the primary lumen is at an acute angle.

7. The overtube attachment device according embodiment 1, wherein the body is annular.

8. The overtube attachment device according to embodiment 1, wherein the body comprises a body wall having a wall thickness that is not constant from the proximal end to the distal end.

9. The overtube attachment device according to embodiment 8, wherein the body wall tapers toward the distal opening.

10. The overtube attachment device according to embodiment 1, wherein an external thread is formed on the distal portion configured for engagement with a grip portion internal thread formed within a grip portion connector of the overtube.

11. The overtube attachment device according to embodiment 1, wherein, in the operational configuration, a separator is connected to the suction opening as part of the suction system.

12. The overtube attachment device according to embodiment 1, wherein the primary lumen and the secondary lumen are substantially annular.

13. The overtube attachment device according to embodiment 1, wherein the secondary lumen is annular with an inside diameter between 5 mm and 40 mm.

14. The overtube attachment device according to embodiment 1, wherein the primary lumen is between 15 mm and 200 mm in length.

15. The overtube attachment device according to embodiment 1, wherein the secondary lumen is between 15 mm and 200 mm in length.

16. The overtube attachment device according to embodiment 1, wherein the body is between 15 mm and 200 mm in length.

17. An embodiment of the present overtube attachment device configured for selective engagement to an overtube having an overtube cap and a suction system, the overtube attachment device further configured for selective receipt therethrough of an endoscope, the overtube device comprising: a body having an endoscope opening formed at a proximal end and an overtube opening formed at a distal end, the endoscope port and the overtube port being in fluid communication; a primary lumen formed through the body to interconnect the endoscope port and the overtube port; and a secondary lumen formed in the body so as to intersect and be in fluid communication with the primary lumen through a suction opening; wherein, in an operational configuration, the overtube is engaged with the overtube port, the suction system is engaged to the suction port, and the overtube cap is engaged to the endoscope opening, the endoscope is received into the endoscope opening through the overtube cap.

18. The overtube attachment device according to embodiment 17, wherein one of an internal thread or a barb fitting is formed at the suction opening.

19. The overtube attachment device according to embodiment 17, wherein one of a primary lumen inside diameter is substantially equal to a secondary lumen inside diameter or the primary lumen inside diameter is greater than the overtube inside diameter.

20. The overtube attachment device according to embodiment 17, wherein, in the operational configuration, a separator is connected to the suction opening as part of the suction system.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular apparatus, methodology, configuration, size, shape, material of construction, protocol, etc., described herein, but may include any such technology now known or later developed without departing from the spirit and scope of the specification. As such, various modifications or changes to or alternative configurations of the disclosed subject matter can be made in accordance with the teachings herein without departing from the spirit and scope of the present specification. Lastly, the terminology used herein is for the purpose of describing particular embodiments only, and is not intended to limit the scope of the present invention. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. An overtube attachment device configured for selective engagement with each of an overtube and a suction system, the overtube attachment device further configured for selective receipt therethrough of an endoscope, the overtube attachment device comprising:
   a body having a proximal opening formed at a proximal end and a distal opening formed at a distal end, the distal opening configured for removable engagement with the overtube;
   a primary lumen formed through the body and interconnecting the proximal opening with the distal opening, the primary lumen sized and shaped for allowing the endoscope to be slidably moved therethrough while also being sized and shaped for allowing an esophageal food impaction to be retrieved from an esophagus of a patient and slidably moved through the primary lumen, the primary lumen having an inside diameter of between 14 mm and 40 mm; and
   a secondary lumen formed in the body so as to intersect and be in fluid communication with the primary lumen through a suction port provided by the secondary lumen and configured for removable engagement with the suction system, the secondary lumen being sized and shaped for allowing the food impaction to be retrieved from the patient's esophagus and slidably moved through the secondary lumen via the suction port;
   whereby, in an operational configuration, the overtube attachment device allows the endoscope to slidably move through each of the proximal opening and the overtube via the primary lumen and, upon the endoscope being withdrawn to a location behind the secondary lumen, further allows the suction system to retrieve the food impaction from the patient's esophagus via the overtube and divert the food impaction through the secondary lumen and out the suction port, thereby subsequently leaving the primary lumen unobstructed by the food impaction.

2. The overtube attachment device according to claim 1, further comprising an overtube cap removably engagable with the proximal opening and configured for receiving the endoscope therethrough as the endoscope is inserted into the proximal opening in the operational configuration.

3. The overtube attachment device according to claim 1, wherein one of an internal thread or a barb fitting is formed at the suction port.

4. The overtube attachment device according to claim 1, wherein one of the primary lumen inside diameter is substantially equal to a secondary lumen inside diameter or the primary lumen inside diameter is greater than an overtube inside diameter.

5. The overtube attachment device according claim 1, wherein intersection of the secondary lumen with the primary lumen is at an acute angle.

6. The overtube attachment device according to claim 1, wherein the body is annular.

7. The overtube attachment device according to claim 1, wherein the body comprises a body wall having a wall thickness that is not constant from the proximal end to the distal end.

8. The overtube attachment device according to claim 7, wherein the body wall tapers toward the distal end.

9. The overtube attachment device according to claim 1, wherein an external thread is formed on a distal portion of the distal end of the body configured for engagement with a grip portion internal thread formed within a grip portion connector of the overtube.

10. The overtube attachment device according to claim 1, wherein, in the operational configuration, a separator is connected to the suction port as part of the suction system.

11. The overtube attachment device according to claim 1, wherein the primary lumen and the secondary lumen are substantially annular.

12. The overtube attachment device according to claim 1, wherein the secondary lumen is annular with an inside diameter between 14 mm and 40 mm.

13. The overtube attachment device according to claim 1, wherein the primary lumen is between 15 mm and 200 mm in length.

14. The overtube attachment device according to claim 1, wherein the secondary lumen is between 15 mm and 200 mm in length.

15. The overtube attachment device according claim 1, wherein the body is between 15 mm and 200 mm in length.

16. An overtube attachment device configured for selective engagement with an overtube, the overtube attachment device further configured for selective receipt therethrough of an endoscope, the overtube attachment device comprising:
   a body having a proximal opening formed at a proximal end and a distal opening formed at a distal end, the distal opening configured for removable engagement with the overtube;
   a primary lumen formed through the body and interconnecting the proximal opening with the distal opening, the primary lumen sized and shaped for allowing the endoscope to be slidably moved therethrough while also being sized and shaped for allowing an esophageal food impaction to be retrieved from an esophagus of a patient and slidably moved through the primary lumen, the primary lumen having an inside diameter of between 14 mm and 40 mm
a secondary lumen formed in the body so as to intersect and be in fluid communication with the primary lumen through a suction port provided by the secondary lumen, the secondary lumen being sized and shaped for allowing the food impaction to be retrieved from the patient's esophagus and slidably moved through the secondary lumen via the suction port; and
a suction system comprising:
 a vacuum pump in fluid communication with the suction port of the secondary lumen; and
 a separator positioned inline between the vacuum pump and the suction port, the separator configured for retaining the food impaction;
whereby, in an operational configuration, the overtube attachment device allows the endoscope to slidably move through each of the proximal opening and the overtube via the primary lumen and, upon the endoscope being withdrawn to a location behind the secondary lumen, the suction system is able to retrieve the food impaction from the patient's esophagus via the overtube and divert the food impaction through the secondary lumen, out the suction port and into the separator, thereby subsequently leaving the primary lumen unobstructed by the food impaction.

17. The overtube attachment device according to claim 16, wherein one of an internal thread or a barb fitting is formed at the suction opening.

18. The overtube attachment device according to claim 16, wherein one of the primary lumen inside diameter is substantially equal to a secondary lumen inside diameter or the primary lumen inside diameter is greater than an overtube inside diameter.

19. A method for retrieving and removing an esophageal food impaction from an esophagus of a patient using the overtube attachment device of claim 16, the method comprising the steps of:
 engaging the distal opening of the overtube attachment device with the overtube;
 engaging the suction port of the overtube attachment device with the suction system;
 inserting at least a portion of the overtube a distance into the esophagus of the patient;
 inserting the endoscope through the proximal opening of the overtube attachment device, and selectively moving the endoscope through the primary lumen as well as a distance through the overtube to locate the food impaction within the patient's esophagus;
 retracting the endoscope a distance so as not to obstruct the secondary lumen of the overtube attachment device;
 applying suction to the overtube using the vacuum pump of the suction system to retrieve the food impaction from the patient's esophagus via the overtube and divert the food impaction through the secondary lumen, out the suction port and into the separator, thereby subsequently leaving the primary lumen unobstructed by the food impaction; and
 moving the endoscope a distance through the overtube again to confirm that the food impaction has been completely removed from the patient's esophagus;
 whereby, the steps of locating the food impaction, removing the food impaction, and confirming the complete removal of the food impaction are all achieved through a single intubation event.

\* \* \* \* \*